(12) United States Patent
Ho et al.

(10) Patent No.: US 11,555,037 B2
(45) Date of Patent: *Jan. 17, 2023

(54) PURINE DIONES AS WNT PATHWAY MODULATORS

(71) Applicant: Agency for Science, Technology and Research, Singapore (SG)

(72) Inventors: Soo Yei Ho, Singapore (SG); Stephanie Eliane Blanchard, Singapore (SG); Athisayamani Jeyaraj Duraiswamy, Singapore (SG); Jenefer Alam, Singapore (SG); Vikrant Arun Adsool, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 17/100,474

(22) Filed: Nov. 20, 2020

(65) Prior Publication Data

US 2021/0155623 A1 May 27, 2021

Related U.S. Application Data

(60) Continuation of application No. 16/716,268, filed on Dec. 16, 2019, now Pat. No. 10,844,063, which is a division of application No. 15/899,675, filed on Feb. 20, 2018, now Pat. No. 10,526,335, which is a continuation of application No. 14/893,172, filed as application No. PCT/SG2014/000217 on May 19, 2014, now Pat. No. 9,926,320.

(30) Foreign Application Priority Data

May 23, 2013 (GB) .................................... 1309333

(51) Int. Cl.
C07D 473/06 (2006.01)
A61K 31/522 (2006.01)
A61K 31/5377 (2006.01)
C07D 473/08 (2006.01)

(52) U.S. Cl.
CPC .......... C07D 473/06 (2013.01); A61K 31/522 (2013.01); A61K 31/5377 (2013.01); C07D 473/08 (2013.01)

(58) Field of Classification Search
CPC ... C07D 473/06; C07D 473/08; A61K 31/522
See application file for complete search history.

(56) References Cited

U.S. PATENT DOCUMENTS

| | | | |
|---|---|---|---|
| 6,620,828 B2 | 9/2003 | Chu et al. | |
| 7,671,061 B2 | 3/2010 | Moran et al. | |
| 8,178,542 B2 | 5/2012 | Moran et al. | |
| 8,362,025 B2 | 1/2013 | Ng et al. | |
| 8,377,970 B2 | 2/2013 | Muthuppalaniappan et al. | |
| 8,389,529 B2 | 3/2013 | Moran et al. | |
| 8,541,423 B2 | 9/2013 | Moran et al. | |
| 8,546,396 B2 | 10/2013 | Cheng et al. | |
| 8,592,398 B2 | 11/2013 | Kumar et al. | |
| 8,642,660 B2 | 2/2014 | Goldfarb | |
| 8,697,887 B2 | 4/2014 | Hood et al. | |
| 8,921,364 B2 | 12/2014 | Muthuppalaniappan et al. | |
| 8,993,612 B2 | 3/2015 | Muthuppalaniappan et al. | |
| 9,006,207 B2 | 4/2015 | Ng et al. | |
| 9,181,235 B2 | 11/2015 | Cheng et al. | |
| 9,186,360 B2 | 11/2015 | Khairatkar-Joshi et al. | |
| 9,193,729 B2 | 11/2015 | Metcalf et al. | |
| 9,926,320 B2 * | 3/2018 | Ho | A61K 31/5377 |

(Continued)

FOREIGN PATENT DOCUMENTS

WO WO-2007/073505 6/2007
WO WO-2009/140519 11/2009

(Continued)

OTHER PUBLICATIONS

Australian Examination Report No. 2, dated Mar. 31, 2017, 7 pages.
Chemical Abstracts Service Registry No. (CAS RN) 1099861-81-0 for 8-chloro-N-[4-(2-chloroyphenyl)-2-thiazolyl]-1,2,3,6-tetrahdro-1,3-dimethyl-2,6-dioxo-7H-purine-7-acetamide, STN Entry date Feb. 3, 2009.
Chemical Abstracts Service Registry No. (CAS RN) 1316979-73-3 for 7H-Purine-7-butanamide, N-[6-(1 H-benzimidazol-1-yl)-3-pyridinyl]-1,2,3,6-tetrahydro-1,3-dimetyyl-2, 6-dioxo, STN Entry date Aug. 14, 2011.
Chemical Abstracts Service Registry No. (CAS RN) 1321376-19-5, STN Entry date Aug. 22, 2011.
Chemical Abstracts Service Registry No. (CAS RN) 1385094-68-7 for N-[4-(4-fluorophenyl)-2-thiazolyl]-1,2,3,6-tetrahydro-α,1,3-trimethyl-2,6-dioxo-7H-purine-7-acetamide, STN Entry Date Aug. 1, 2012.

(Continued)

*Primary Examiner* — Pancham Bakshi
(74) *Attorney, Agent, or Firm* — Foley & Lardner LLP

(57) ABSTRACT

The invention relates to the use of compounds of general structure (I) in modulation of the Wnt pathway

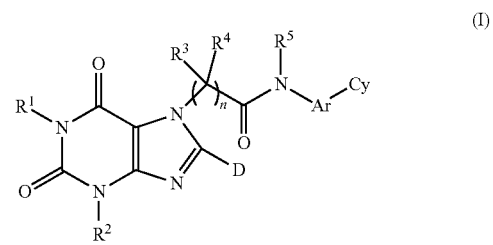

wherein $R^1$, $R^2$, $R^3$, $R^4$ and $R^5$ are each, independently, H or an alkyl group; D is selected from the group consisting of H, halogen, alkyl, cycloalkyl, aryl, and dialkylamino, each (other than H and halogen) being optionally substituted; Ar is an aryl or heteroaryl group, optionally substituted; Cy is an aryl, heteroaryl or a saturated ring containing at least one heteroatom, each being optionally substituted; and n is an integer from 1 to 3.

18 Claims, 4 Drawing Sheets

(56) References Cited

U.S. PATENT DOCUMENTS

| | | | |
|---|---|---|---|
| 10,472,360 B2 | 11/2019 | Ho et al. | |
| 10,526,335 B2* | 1/2020 | Ho | A61P 35/02 |
| 10,844,063 B2 | 11/2020 | Ho et al. | |
| 2009/0143377 A1* | 6/2009 | Ng | A61P 29/00 |
| | | | 514/263.21 |
| 2009/0163545 A1 | 6/2009 | Goldfarb | |
| 2011/0053882 A1* | 3/2011 | Yu | A61K 31/52 |
| | | | 514/43 |
| 2012/0046305 A1 | 2/2012 | Moran et al. | |
| 2012/0108614 A1 | 5/2012 | Chong | |
| 2012/0157411 A1 | 6/2012 | Kumar et al. | |
| 2012/0316136 A1 | 12/2012 | Khairatkar-Joshi et al. | |
| 2013/0165427 A1 | 6/2013 | Chong | |
| 2013/0303524 A1 | 11/2013 | Bersot et al. | |
| 2014/0221401 A1 | 8/2014 | Moran et al. | |
| 2015/0166526 A1 | 6/2015 | Muthuppalaniappan et al. | |
| 2015/0291588 A1 | 10/2015 | Muthuppalaniappan et al. | |
| 2016/0090386 A1 | 3/2016 | Ho et al. | |
| 2017/0334912 A1 | 11/2017 | Ho et al. | |
| 2018/0170932 A1 | 6/2018 | Ho et al. | |

FOREIGN PATENT DOCUMENTS

| | | |
|---|---|---|
| WO | WO-2010/036821 | 4/2010 |
| WO | WO-2010/075353 | 7/2010 |
| WO | WO-2011/042798 | 4/2011 |
| WO | WO-00/75120 | 12/2012 |
| WO | WO-2013/014597 | 1/2013 |
| WO | WO-2013/023102 | 2/2013 |

OTHER PUBLICATIONS

Chemical Abstracts Service Registry No. (CAS RN) 877949-70-7 for 1,2,3,6-tetrahydro-1,3-dimethyl-2,6-dioxo-N-[4-(2-thiazolyl)phenyl]-7H-purine-7-butanamide, STN Entry date Mar. 24, 2006.

Chemical Abstracts Service Registry No. (CAS RN) 916030-47-2 for 1,2,3,6-tetrahydro-1,3-dimethyl-2,6-dioxo-N-[4-[4-(phenylmethyl)-1-piperazinyl]phenyl]-7H-purine-7-acetamide, STN Entry date Dec. 20, 2006.

Chemical Abstracts Service Registry No. (CAS RN) 938974-62-0 for 2-[[1-oxo-2-(1,2,3,6-tetrahydro-1,3-dimethyl-2,6-dioxo-7H-purin-7-yl)propyl]amino]-5-phenyl-3-thiophenecarboxylic acid ethyl ester, STN Entry Date Jun. 25, 2007.

European Search Report dated Sep. 21, 2016 in European application No. 14801575 (9 pages).

International Preliminary Report on Patentability dated Sep. 1, 2015 in International application No. PCT/SG2014/000217.

International Search Report dated Aug. 21, 2014 in International application No. PCT/SG2014/000217.

Zhan et al., "Wnt signaling in cancer," Oncogene, vol. 36, pp. 1461-1473 (2017) Published online Sep. 2016.

Office Action dated Feb. 12, 2019 in U.S. Appl. No. 15/899,675 (US 2018-0170932).

* cited by examiner

PURINE DIONES AS WNT PATHWAY MODULATORS

CROSS-REFERENCE TO RELATED APPLICATIONS

This application is a continuation of U.S. patent application Ser. No. 16/716,268, filed Dec. 16, 2019, (now U.S. Pat. No. 10,844,063), which is a divisional of U.S. patent application Ser. No. 15/899,675, filed Feb. 20, 2018 (now U.S. Pat. No. 10,526,335), which is a continuation of U.S. patent application Ser. No. 14/893,172, filed Nov. 23, 2015 (now U.S. Pat. No. 9,926,320), which is the U.S. national stage of International Application No. PCT/SG2014/000217 filed May 19, 2014, and claims priority to Great Britain Patent Application No. 1309333.1 filed May 23, 2013.

FIELD

The invention relates to Wnt pathway modulators, processes for making them and methods for using them.

BACKGROUND

The present application claims priority from application GB1309333.1, filed on 23 May 2013, the entire contents of which are incorporated herein by cross-reference.

Wnt proteins are secreted glycoproteins acting as growth factors that regulate various cellular functions, including proliferation, differentiation, death, migration, and polarity, by activating multiple intracellular signalling cascades, including the β-catenin-dependent and—independent pathways. There are 19 Wnt members that have been found in humans and mice, and they exhibit unique expression patterns and distinct functions during development. In humans and mice, the 10 members of the Frizzled (Fz) family comprise a series of seven-pass transmembrane receptors that have been identified as Wnt receptors. In addition to Fz proteins, single-pass transmembrane proteins, such as low-density lipoprotein receptor-related protein 5 (LRP5), LRP6, receptor tyrosine kinase (RTK)-like orphan receptor 1 (Ror1), Ror2, and receptor-like tyrosine kinase (Ryk), have been shown to function as co-receptors for Wnt signalling. Therefore, it has been assumed traditionally that the binding of different Wnts to their specific receptors selectively triggers different outcomes via distinct intracellular pathways.

In the absence of Wnt signalling, β-catenin is bound and phosphorylated by a "destruction complex" containing the adenomatous polyposis coli (APC) and Axin proteins, as well as glycogen synthase kinase 3 (GSK3) and casein kinase I (CKI). Phosphorylated β-catenin is bound by the F box protein Slimb/β-TrCP and polyubiquitinated, leading to proteosomal degradation. In addition, the complex acts to prevent nuclear localization of β-catenin. Upon Wnt binding to Frizzled (Fz) and low-density lipoprotein-related proteins 5 and 6 (LRP5/6), GSK3, Axin, and other destruction complex components are recruited to the receptor complex. The function of the destruction complex is inhibited, and unphosphorylated β-catenin accumulates in the cytoplasm and eventually translocates to the nucleus. There, it associates with TCF proteins, converting TCF from a repressor into an activator of Wnt-responsive gene transcription.

Deregulation of components of Wnt/β-catenin signalling is implicated in a wide spectrum of diseases including degenerative diseases, metabolic diseases, and a number of cancers such as cervical, colon, breast, bladder, head and neck, gastric, lung, ovarian, prostate, thyroid, non-small-cell lung, as well as chronic lymphocytic leukemia, mesothelioma, melanoma, pancreatic adenocarcinoma, basal cell carcinoma, osteosarcoma, hepatocellular carcinoma, Wilm's tumor and medulloblastoma. Wnt signalling plays a role both during development, and within stem cell niches in adults. This is best established in skin, hematopoietic stem cells, mammary gland and in intestinal proliferation. For example, high level expression of DKK1, an inhibitor of Wnt signalling, blocks normal stem cell proliferation in mouse intestines, suggesting there is an essential role for Wnt signalling in maintenance of stem cells in the digestive tract. The role of Wnt in self renewal and expansion of stem cells has also been demonstrated for embryonic and neural stem cells, suggesting that Wnt signalling may be a general requirement of stem cell maintenance.

Inhibition of Wnt signalling, e.g., by overexpression of axin or an extracellular Wnt-binding protein, sFRP, reduces hematopoietic stem cell (HSC) growth in vitro and the ability to reconstitute HSCs in vivo. Notably, while overexpression of activated β-catenin can expand HSC populations in culture for extended periods, two groups have reported that β-catenin is not required for HSC survival and serial transplantation, supporting the proposal that there is more to Wnt signalling than stabilization of β-catenin in stem cell survival. Diverse Wnts can regulate stem cell proliferation: Wnts 1, 5a, and 10b are able to stimulate expansion of HSC populations and Wnt5a acts synergistically with stem cell factor (SCF) to expand and promote self-renewal of HSCs. The demonstration of a role for Wnt5a in HSC self-renewal and its ability to synergize with stem cell factor is particularly interesting because Wnt5a often acts in a β-catenin independent manner. While Wnt signalling is critical for stem cell maintenance, it may therefore be via signalling pathways distinct from or in parallel to the β-catenin pathway.

Wnt/β-catenin signalling pathway is essential to embryonic development in general and organ morphogenesis, so it is not surprising that dysregulation of this pathway in adult has been linked to fibroblast biology and fibrosis. It has been demonstrated that Wnt/β-catenin signalling play a role in severe fibrotic diseases, such as pulmonary fibrosis, liver fibrosis, skin fibrosis and renal fibrosis.

Dysregulation of Wnt/β-catenin signalling contributes also to the development of diabetic retinopathy by inducing retinal inflammation, vascular leakage, and neovascularization. The binding of Wnt proteins to plasma membrane receptors on mesenchymal cells induces the differentiation of these cells into the osteoblast lineage and thereby supports bone formation. Wnts are also key signalling proteins in joint remodeling processes. Active Wnt signalling contributes to osteophyte formation and might have an essential role in the anabolic pattern of joint remodeling that is observed in ankylosing spondylitis and osteoarthritis. In contrast, blockade of Wnt signalling facilitates bone erosion and contributes to catabolic joint remodeling, a process that is observed in rheumatoid arthritis.

There is therefore a need for compounds that modulate or inhibit Wnt activity so as to treat diseases associated with Wnt activity.

SUMMARY OF INVENTION

In a first aspect of the invention there is provided a compound of structure (I) for use in, or when used in, modulating Wnt activity,

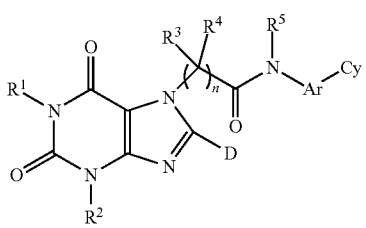

wherein:

R¹, R², R³, R⁴ and R⁵ are each, independently, H or an alkyl group;

D is selected from the group consisting of H, halogen, alkyl, cycloalkyl, aryl, and dialkylamino, each (other than H and halogen) being optionally substituted;

Ar is an aryl or heteroaryl group, each being optionally substituted;

Cy is an aryl, heteroaryl or a saturated ring containing at least one heteroatom, each being optionally substituted; and n is an integer from 1 to 3.

In some embodiments, if n=1 and one of R³ and R⁴ is methyl and the other is H, the stereochemistry of the compound is as shown in partial structure (II)

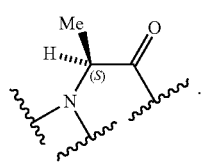

In some particular embodiments, n=1 and one of R³ and R⁴ is methyl and the other is H and the stereochemistry of the compound is as shown in partial structure (II).

Any one or more of the following groups a) to e), and/or any one or more individual compounds within any one or more of said groups, optionally all thereof, may be excluded from the scope of the first aspect. Notwithstanding any such exclusions, the compounds referred to hereinafter as compound 5 and compound 86 may be explicitly included within the scope of the first aspect.

a) Any one or more of the compounds described in WO2010/036821 A1;

b) Any one or more compounds of the formula shown below,

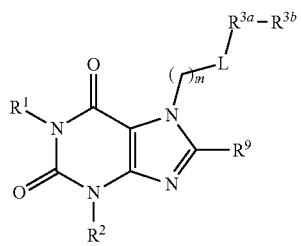

wherein, $R^1$ and $R^2$ are each independently $C_1$-$C_6$ alkyl, $C_2$-$C_6$ alkenyl, or $C_2$-$C_6$ alkynyl, each of which is optionally substituted with 1-4 $R^5$; L is $NR^6SO_2$, $SO_2NR^6$, $OC(O)NR^6$, $NR^6C(O)O$, $NR^6C(O)NR^6$, $NR^6C(O)$, $C(O)NR^6$, O, C(O), S, S(O), $S(O)_2$, $NR_6$, or $CH_2$, each of $R^{3a}$ and $R^{3b}$ is independently cyclyl, heterocyclyl, aryl, heteroaryl, each of which is optionally substituted with 1-4 $R^7$; each $R^5$ is independently halo, hydroxyl, alkoxy, amino, alkylamino, dialkylamino, cyano, nitro, amido (e.g., where the nitrogen of the amide is substituted by an alkyl, or where the nitrogen of the amide together with two carbons to which it is attached, forms a ring), alkylamido, dialkylamido, thioyl, sulfonyl, cyclyl, heterocyclyl, aryl, or heteroaryl; each $R^6$ is independently H, $C_1$-$C_6$ alkyl, $C_1$-$C_6$ alkenyl, hydroxy$C_1$-$C_6$ alkyl, alkoxy$C_1$-$C_6$ alkyl, cyanoalkyl, haloalkyl, arylalkyl, S(O)alkyl, acyl, amino, amidyl, or $S(O)_2H$, aryl, alkoxyaryl; each $R^7$ is independently $C_1$-$C_6$ alkyl, $C_2$-$C_6$ alkenyl, or $C_2$-$C_6$ alkynyl, halo, hydroxyl, alkoxy, oxo, aryl, heteroaryl, cyclyl, heterocyclyl, arylalkyl, heteroarylalkyl, cyclylalkyl, heterocyclylalkyl, aryloxy, arylalkoxy, amino, akylamino, dialkylamino, thioyl, alkylthioyl, sulfonyl, sulfonamidyl, amido (e.g., where the nitrogen of the amide is substituted by an alkyl, or where the nitrogen of the amide together with two carbons to which it is attached, forms a ring), hydroxyl alkoxyl, alkoxy —C(O)OH, —C(O)Oalkyl, urea, sulfonylurea, acyl, nitro, cyano, each of which is optionally substituted with 1-3 $R^8$; each $R^8$ is independently $C_1$-$C_6$ alkyl, $C_2$-$C_6$ alkenyl, or $C_2$-$C_6$ alkynyl, aryl, heteroaryl, cyclyl, halo, hydroxyl, alkoxy, oxo, aryloxy, amino, akylamino, dialkylamino, C(O)OH, —C(O)Oalkyl, thioyl, sulfonyl, sulfonamidyl, amido (e.g., where the nitrogen of the amide is substituted by an alkyl, or where the nitrogen of the amide together with two carbons to which it is attached, forms a ring), urea, sulfonylurea, acyl, nitro, cyano, cyclyl, heterocyclyl, aryl, or heteroaryl; $R^9$ is H, $C_1$-$C_6$ alkyl, $C_2$-$C_6$ alkenyl, or $C_2$-$C_6$ alkynyl, halo, $C_1$-$C_6$ haloalkyl, hydroxyl, alkoxy, aryloxy, arylalkoxy, amino, akylamino, dialkylamino, thioyl, alkylthioyl, sulfonyl, sulfonamidyl, amido, urea, sulfonylurea, acyl, nitro, cyano, each of which is optionally substituted with 1-3 $R^8$; m is 1, 2, 3, 4, 5, or 6.

c) Any one or more compounds of structure I wherein R¹ and R² are both methyl, D, R³, R⁴ and R⁵ are all H, n is 1 and Ar-Cy is 4-phenylthiazole-2-yl, 4-(4-bromophenyl)thiazole-2-yl, 2- or 4-(N-morpholinyl)phenyl, 4-(N-piperidinyl)phenyl, 1-phenyl-3-methylpyrazole-5-yl, 4-(3,4-dimethylphenyl)thiazole-2-yl, 4-(4-ethylphenyl)thiazole-2-yl, 4-(2,4,6-trimethylphenyl)thiazole-2-yl, 4-(4-n-propylphenyl)thiazole-2-yl, 4-(4-chorophenyl)-5-methylthiazole-2-yl, 4-phenylphenyl, 2-(N-pyrrolidinyl)phenyl, 4-(N-azacycloheptyl)phenyl, 4-(4-bromophenyl)-5-trifluoromethylpyrimidine-2-yl, 4-(2,4-dimethylphenyl)thiazole-2-yl, 4-(3,4-dimethoxylphenyl)thiazole-2-yl, 4-(2-fluorophenyl)thiazole-2-yl, 4-(3,4-difluorophenyl)-5-methylthiazole-2-yl, 4-(4-methoxy-1-naphthyl)thiazole-2-yl, 4-(3-chloro-4-methoxyphenyl)thiazole-2-yl, 4-(4-ethoxyphenyl)-5-methylthiazole-2-yl, 4-(2-acetamido-4-fluorophenyl)thiazole-2-yl, 4-(3-fluoro-4-methoxyphenyl)thiazole-2-yl, 4-(4-bromophenyl)-5-methylthiazole-2-yl, 4-(4-(2-methoxyethyl)phenyl)thiazole-2-yl, 4-(4-methyl-3-nitrophenyl)thiazole-2-yl, 4-phenyl-5-(1-methyl-imidazole-2-yl) thiazole-2-yl, 4-(4-(difluromethoxy)phenyl)-5-methylthiazole-2-yl, 4-(2,5-diethoxyphenyl)thiazole-2-yl, 4-(4-fluoromethylphenyl)-5-methylthiazole-2-yl, 4-phenyl-5-acetylthiazole-2-yl, 4-(3-chloro-4-fluorophenyl)thiazole-2-yl, 4-(3-fluorophenyl)thiazole-2-yl, 4-(3-methoxyphenyl) thiazole-2-yl, 4-(2-ethoxyphenyl)thiazole-2-yl, 4-(3-chlorophenyl)thiazole-2-yl, 4-(2-methoxyphenyl)thiazole-2-yl, 4-(2-bromophenyl)thiazole-2-yl, 4-(4-diethylaminophenyl)thiazole-2-yl, 4-(2-chlorophenyl) thiazole-2-yl, 4-(4-methoxyphenyl)thiazole-2-yl, 4-(3-bromophenyl)thiazole-2-yl, 4-(4-isopropoxyphenyl) thiazole-2-yl, 4-(2,3,4-trichlorophenyl)thiazole-2-yl, 4-(3-chloro-4-ethoxyphenyl)thiazole-2-yl, 4-(4-chloro-3- fluorophenyl)thiazole-2-yl, 4-(3-ethoxyphenyl)thiazole-2-yl, 4-(2, 4-dimethoxyphenyl)thiazole-2-yl, 4-(2, 4-dimethylphenyl)thiazole-2-yl, 4-(4-ethylphenyl)thiazole-2-yl, 4-(2-methylphenyl)thiazole-2-yl, 4-(2-bromo-5-ethoxyphenyl)thiazole-2-yl, 4-(5-bromo-2-chloro-4-ethoxyphenyl)thiazole-2-yl, 4-(2-chloro-4-ethoxyphenyl)thiazole-2-yl, 4-(3-pyridyl)thiazole-2-yl, 4-(4-(2-hydroxyethoxy)phenyl)thiazole-2-yl, 4-(3-(2-hydroxyethoxy)phenyl)thiazole-2-yl, 4-(2,6-dichlorophenyl)thiazole-2-yl, 4-(3-methylphenyl)thiazole-2-yl, 4,5-bis(4-methylphenyl)oxazole-2-yl, 4,5-diphenyloxazole-2-yl, 4-(4-pyridyl)thiazole-2-yl, 4-(2-(2-hydroxyethoxy)phenyl)thiazole-2-yl, 4-(3,4-dichlorophenyl)-5-methylthiazole-2-yl, 4-(2,4,6-trichlorophenyl)thiazole-2-yl, 4-(4-ethoxyphenyl)-5-phenylthiazole-2-yl, 4-(4-chloro-3-ethoxyphenyl)thiazole-2-yl, 4-(3,4,5-trichlorophenyl)thiazole-2-yl, 5-(4-pyridyl)1,3,4-thiadiazole-2-yl, 4-(3-bromo-6-(2-hydroxyethoxy)phenyl)thiazole-2-yl, 3-(benzoxazole-2-yl)-2-methylphenyl, 4-(3,4-dichlorophenyl)-5-ethylthiazole-2-yl, 4-((3-trifluoromethyl)phenyl)thiazole-2-yl, 4-(2,3-dichlorophenyl)-5-phenylthiazole-2-yl, 4-(2,3-dichlorophenyl)-5-(4-methylphenyl)thiazole-2-yl, 1-phenyl-3-(4-methylphenyl)pyrazole-5-yl, 4,5-bis(3,4-dichlorophenyl)thiazole-2-yl, 5-phenylthiazole-2-yl, 4-(4-(trifluoromethyl)phenyl)thiazole-2-yl, 4-(4-(methylsulfinyl)phenyl)thiazole-2-yl, 4-(4-chlorophenyl)oxazole-2-yl, 4-((4-trifluoromethoxy)phenyl)thiazole-2-yl, 3-(4-chlorophenyl)pyrazole-5-yl, 3-(4-chlorophenyl)1,3,4-oxadiazole-5-yl, 3-phenylpyrazole-5-yl, 5-(4-methylphenyl)thiazole-2-yl, 4-(4-chlorophenyl)-5-ethylthiazole-2-yl, 4-(4-nitrophenyl)thiazole-2-yl, 4-(4-aminophenyl)thiazole-2-yl, 4-(4-ethoxyphenyl)-5-methyloxazole-2-yl, 4-(4-dimethylamino-3-fluorophenyl)thiazole-2-yl, 3-(thiophene-2-yl)pyrazole-5-yl, 3-(furan-2-yl)pyrazole-5-yl, 4-(4-chlorophenyl)-5-fluorothiazole-2-yl, 2-(pyrrole-N-yl)phenyl, 2-(indole-2-yl)phenyl, 4-(2-hydroxybenzimidazole-5-yl)thiazole-2-yl, 2-(4-chlorophenyl)-4-pyridyl, 3-(4-chlorophenyl)phenyl, 4-(3-chloro-4-dimethylaminophenyl)thiazole-2-yl, 4-(4-ethoxyphenyl)thiazole-2-yl, 5-(4-chlorophenyl)-3-pyridyl, 4-(3, 4-dichlorophenyl)-5-isopropylthiazole-2-yl, 4-(4-dimethylamino-2-fluorophenyl)thiazole-2-yl, 4-(4-(tetrahydropyrrole-N-yl)-3-bromophenyl)thiazole-2-yl, 4-(4-fluoro-3-(morpholine-N-yl)phenyl)thiazole-2-yl, 5-(4-chlorophenyl)pyrazole-2-yl, 4-(2,4,5-trichlorophenyl)thiazole-2-yl, 4-(4-diethylaminophenyl)thiazole-2-yl, 4-(2,3-dihydrobenzofuran5-yl)thiazole-2-yl, 2-(3,4-dichlorophenyl)thiazole-4-yl, 3-phenyl-4-(4-ethoxyphenyl)imidazole-2-yl, 4-(piperidine-N-ylphenyl)thiazole-2-yl, 4-(morpholine-N-ylphenyl)thiazole-2-yl, 4-(3-diethylaminophenyl)thiazole-2-yl, 2-(benzothiazole-2-yl)phenyl, 4-(3-ethylpropylaminophenyl)thiazole-2-yl, 4-(3-dimethylaminophenyl)thiazole-2-yl, 4-(4-chlorophenyl)pyridine-2-yl, 3-(4-diethylaminophenyl)phenyl, 4-(4-ethoxyphenyl)imidazole-2-yl, 4-(N-acetyl-2,3-dihydroindole-5-yl)thiazole-2-yl, 4-(3,4-dichlorophenyl)pyrimidine-2-yl, 3-(thiazole-2-yl)phenyl, 4-(quinoline-2-yl)thiazole-2-yl, 4-(benzothiophene-2-yl)thiazole-2-yl, 4-(isoquinoline-3-yl)thiazole-2-yl, 4-(4-dimethylamino-3,5-difluorophenyl)thiazole-2-yl, 4-(3-(pyrrolidine-N-yl)phenyl)thiazole-2-yl, 4-(4-(aminocarbonylamino)phenyl)thiazole-2-yl, 4-(4-chlorophenyl)-5-methoxythiazole-2-yl, 4-(4-diethylsulfonamidophenyl)thiazole-2-yl, 4-(4-dimethylsulfonamidophenyl)thiazole-2-yl, 4-(2,3-dihydro-1,4-benzoxazine-3-one-6-yl)thiazole-2-yl, 4-(3,4-dichlorophenyl)imidazole-2-yl, 4-(4-ethoxyphenyl)oxazole-2-yl, 4-(4-chlorophenyl)oxazole-2-yl, 3-(4-ethylthiazole-2-yl)phenyl, 3-(5-ethylthiazole-2-yl)phenyl, 3-(4-methylthiazole-2-yl)phenyl, 4-(2-chloro-4-diethylaminophenyl)thiazole-2-yl, 4-(2,5-difluoro-4-diethylaminophenyl)thiazole-2-yl, 4-(3-trifluoromethoxyphenyl)thiazole-2-yl, 6-(4-chlorophenyl)pyridine-2-yl, 3-(4-diethylamino-3-fluorophenyl)phenyl, 4-(4-dimethylamino-2,3-difluorophenyl)thiazole-2-yl), 4-(4-(piperidine-N-ylsulfonyl)phenyl)thiazole-2-yl, 4-(N-acetylindole-5-yl)thiazole-2-yl, 1-phenylmethyl-4-(3,4-dichlorophenyl)imidazole-2-yl, 4-(N-ethyl-2,3-dihydroindole-5-yl)thiazole-2-yl, 3-(4-chlorophenyl)1,2,4-thiadiazole-5-yl, 4-(N-acetyl-2,3-dihydroindole-5-yl)thiazole-2-yl, 4-(N-ethylindole-5-yl)thiazole-2-yl, 1-(4-chlorophenyl)1,2,4-triazole-3-yl, 1-phenylpyrazole-4-yl, 4-(N-acetylindole-6-yl)thiazole-2-yl, 1-(4-chlorophenyl)pyrazole-4-yl, 4-(N-methyl-2,3-dihydroindole-5-yl)thiazole-2-yl, 4-(2-chloro-4-dimethylamino-5-fluorophenyl)thiazole-2-yl, 4-(3-(N,N-dimethylsulfonamido)thiazole-2-yl, 4-(3-(N,N-diethylsulfonamido)thiazole-2-yl, 2-(4-chlorophenyl)1,3,5-triazine-6-yl, 4-(4-(N-morpholino)sulfonylphenyl)thiazole-2-yl, 4-(4-(N-pyrrolidino)sulfonylphenyl)thiazole-2-yl, 4-(4-chloro-3-diethylaminophenyl)thiazole-2-yl, 4-(4-chloro-3-trifluoromethylphenyl)thiazole-2-yl, 1-ethyl-4-(3, 4-dichlorophenyl)imidazole-2-yl, 1-methyl-4-(3,4-dichlorophenyl)imidazole-2-yl, 2-(1-naphthyl)-6-pyridyl, 2-(1-(3,4-dichlorophenyl)-6-pyridyl, 4-(4-chlorophenyl)-5-dimethylaminomethylthiazole-2-yl, 4-(3-diethylaminophenyl)thiazole-2-yl, 4-(3-fluoro-4-diethylaminophenyl)-5-ethylthiazole-2-yl, 4-(4-chlorophenyl)-5-(2-dimethylaminoethyl)thiazole-2-yl, 4-(2-fluoro-4-trifluoromethylphenyl)thiazole-2-yl, 4-(3-fluoro-5-trifluoromethylphenyl)thiazole-2-yl, 4-(3-fluoro-4-trifluoromethylphenyl)thiazole-2-yl, 4-(4-fluoro-3-trifluoromethylphenyl)thiazole-2-yl, 4-(3,4-dichlorophenyl)-5-methoxycarbonylmethylthiazole-2-yl, 1,5-dimethyl-4-(3,4-dichlorophenyl)imidazole-2-yl, N-(4-chlorophenyl)pyrrole-3-yl, 4-(3,4-dichlorophenyl)-5-aminocarbonylthiazole-2-yl, 4-(2-ethoxynaphth-6-yl)thiazole-2-yl, 4-(3,4-dichlorophenyl)-5-hydroxycarbonylmethylthiazole-2-yl, 4-(4-diethylamino-2,5-difluorophenyl)-5-methylthiazole-2-yl, 4-(4-(N-pyrrolidino)-3-fluorophenyl)thiazole-3-yl, 4-(4-diethylamino-3-ethoxyphenyl)thiazole-3-yl, 4-(4-diethylamino-2-ethoxyphenyl)thiazole-3-yl, 4-(4-(N-pyrrolidino)-3-trifluoromethylphenyl)thiazole-3-yl, 4-(4-diethylamino-3-trifluoromethylphenyl)thiazole-3-yl, 1-n-butyl-4-(3,4-dichlorophenyl)imidazole-2-yl, 1-(4-chlorophenyl)imidazole-4-yl, 5-(4-chlorophenyl)1,2,4-oxadiazole-3-yl, 4-phenyl-5-(4-ethoxyphenyl)oxazole-2-yl, 2-(2-naphthyl)pyridine-6-yl, 4-(4-methoxycarbonylphenyl)thiazole-2-yl, 4-(3-(methylethylamino)phenyl)-5-methylthiazole-2-yl, 4-(3-diethylamino-4-ethoxyphenyl)thiazole-2-yl, 4-(4-diethylaminophenyl)-5-fluorothiazole-2-yl, 4-(4-(N-ethylpiperazine-N'-yl)-3-trifluoromethylphenyl)thiazole-2-yl, 4-(3-ethoxycarbonylphenyl)thiazole-2-yl, 4-(3,5-difluoro-4-(N-pyrrolidino)phenyl)thiazol-2-yl, 4-(4-chlorophenyl)-5-trifluoromethylthiazole-2-yl, 4-(3-cyano-4-(methylethylamino)phenyl)thiazole-2-yl, 4-(2-ethoxynaphth-5-yl)thiazole-2-yl, 5-(4-chloromethylphenyl)isothiazole-3-yl, 4-(N-methylindole-5-yl)thiazole-2-yl, 4-(3, 4-trichlorophenyl)-5-(2-hydroxyethyl)thiazole-2-yl, 2-(4-chlorophenyl)imidazole-4-yl, 1-(4-chlorophenyl)1,2,3-triazole-4-yl, 4-(4-(N-imidazolyl)phenyl)thiazole-2-yl, 4-(4-(N-tetrazolyl)phenyl)thiazole-2-yl, 4-(4-methoxyphenyl)methylaminophenyl)thiazole-2-yl, 4-(4-(N-pyrrolidinyl)-3,5-difluorophenyl)-5-fluorothiazole-2-yl, 4-(4-(N-morpholino)-3-trifluoromethylphenyl)thiazole-2-yl, 4-(4-(N-piperidinyl)-3-trifluoromethylphenyl)thiazole-2-yl, 4-(4-nitrophenyl)-5-trifluoromethylthiazole-2-yl, 4-(4-dimethylamino-3-trifluoromethylphenyl)-5- trifluoromethylthiazole-2-yl, 4-(3-hydroxycarbonylphenyl)thiazole-2-yl, 4-(4-hydroxycarbonylphenyl)thiazole-2-yl, 4-(2,5-difluoro-4-(N-pyrrolidinyl)phenyl)thiazole-2-yl, 4-(4-diethylamino-3-fluorophenyl)-5-fluorothiazole-2-yl, 4-(4-aminophenyl)-5-trifluoromethylthiazole-2-yl, 4-(4-(N-pyrrolidino)phenyl)thiazole-2-yl, 4-(2,5-difluoro-4-(N-ethylpiperazine-N'-yl)phenyl)thiazole-2-yl, 4-(4-diethylaminophenyl)-5-trifluoromethylthiazole-2-yl, 4-(3,5-difluoro-4-diethylaminophenyl)-5-fluorothiazole-2-yl, 4-(4-(N-morpholinyl)-2,5-difluorophenyl)thiazole-2-yl, 4-(4-(N-piperidinyl)-2,5-difluorophenyl)thiazole-2-yl, 4-(4-(N-pyrazolyl)-3-fluorophenyl)thiazole-2-yl, 4-(4-chlorophenyl)-5-methylthiazole-2-yl,5-methylthiazole-2-ylphenyl, 4-(1-ethoxynaphth-3-yl)thiazole-2-yl, 3-(4-chlorophenyl)isothiazole-5-yl, 4-(benzofuran-5-yl)thiazole-2-yl, 3-(4-chlorophenyl)isoxazole-5-yl, 4-(3-(N-pyrrolidinocarbonyl)phenyl)thiazole-2-yl, 4-(4-dimethylaminophenyl)-5-phenylthiazole-2-yl, 4-(3-(N-morpholinocarbonyl)phenyl)thiazole-2-yl, 4-(4-diethylaminophenyl)-5-trifluoroacetylthiazole-2-yl, 4-(4-diethylamino-3-fluorophenyl)-5-trifluoromethylthiazole-2-yl, 4-(4-ethylamino-3-fluorophenyl)-5-trifluoromethylthiazole-2-yl, 4-(4-diethylamino-3-fluoro-5-trifluoromethylphenyl)-5-trifluoromethylthiazole-2-yl, 4-(4-(2-dimethylaminoethoxy)-3-fluorophenyl)thiazole-2-yl, 4-(4-N-(pyrrolindinyl)phenyl)-5-ethylthiazole-2-yl, 2-(4-(N-pyrrolidinyl)-3-fluorophenyl)pyridine-6-yl, 4-(4-fluoro-3-(N-pyrrolidinyl)phenylthiazole-2-yl, 4-(3-(N-pyrrolidinyl)-4-diethylaminophenyl)thiazole-2-yl, 4-(4-(N-pyrrolyl)phenyl)-5-trifluoromethylthiazole-2-yl, 2-(4-chlorophenyl)thiophene-5-yl, 4-(1-ethoxynaphth-5-yl)thiazole-2-yl, 1-(4-chlorophenyl)pyrazole-3-yl, 4-(4-(N-pyrrolidinyl)-2,5-difluorophenyl)-5-ethylthiazole-2-yl, 4-(4-(N-pyrrolidinyl)-3-trifluoromethylphenyl)-5-methylthiazole-2-yl, 4-(4-(N-piperidinyl)-3-trifluoromethylphenyl)-5-methylthiazole-2-yl, 4-(4-chlorophenyl)-5-n-propylthiazole-2-yl, 4-(4-ethoxy-2-(N-pyrrolidinyl)phenyl)thiazole-2-yl, 4-(4-chloro-2-(N-pyrrolidinyl)phenyl)thiazole-2-yl, 4-(4-(N-pyrrolidinyl)phenyl)-5-fluorothiazole-2-yl, 4-(2-chloropyridine-5-yl)thiazole2-yl, 2-(4-(N-pyrrolidinyl)phenyl)pyridine-6-yl, 4-(4-(N-pyrrolidinyl)-3-fluorophenyl)-5-ethylthiazole-2-yl, 4-(2-chloropyrid-3-yl)thiazole-2-yl, 4-(4-(2-methyl-N-pyrrolidinyl)-3-fluorophenyl)thiazole-2-yl, 4-(4-(N-pyrrolidinyl)-3-trifluoromethylphenyl)-5-methylthiazole-2-yl, 4-(4-diethylamino-2-chlorophenyl)-5-ethylthiazole-2-yl, 5-(4-chlorophenyl)-4-ethylthiazole-2-yl, 4-(3,4-dichlorophenyl)-5-aminothiazole-2-yl, 4-(6-chloroquinoline-3-yl)thiazole-2-yl, 4-(2,4-bis(N-pyrrolidinyl)phenyl)thiazole-2-yl, 4-(4-(2,4-dimethylpyrrolidine-N-yl)phenyl-3-fluorothiazole-2-yl, 4-(thionaphthene-3-yl)thiazole-2-yl, 4-(4-diethylaminophenyl)-5-ethylthiazole-2-yl, 4-(2,6-diethoxy-3-bromophenyl)thiazole-2-yl, 2-thiophene-2-ylphenyl, 2-(pyrrolidone-N-yl)phenyl, 1-phenyl-3-tert-butylpyrazole-5-yl, 4-(4-(1-ethyltetrazolone-4-yl)phenylthiazole-2-yl, 4-(4-diethylaminocarbonylphenyl)-5-phenylthiazole-2-yl, 4-(4-(N-pyrrolidinyl)phenyl)-5-trifluoromethylthiazole-2-yl, 4-(4-pyrimidine-5-ylphenyl)thiazole-2-yl, 4-(4-morpholine-N-yl-3-fluorophenyl)-5-ethylthiazole-2-yl, 4-(4-morpholine-N-yl-3-fluorophenyl)-5-propylthiazole-2-yl, 4-(2-fluoropyridine-4-yl)thiazole-2-yl, 4-(2-fluoropyridine-3-yl)thiazole-2-yl, 4-(4-azacyclohept-N-yl-3-fluorophenyl)thiazole-2-yl, 4-(2-chlororopyridine-4-yl)thiazole-2-yl, 4-(2-methoxypyridine-5-yl)thiazole-2-yl, 4-(3-fluoropyridine-4-yl)thiazole-2-yl, 4-(3,4-dichlorophenyl)-5-nitrothiazole-2-yl, 4-(1-methyl-2,3-dihydroindene-6-yl)thiazole-2-yl, 4-(8-chloroquinoline-3-yl)thiazole-2-yl, 4-(4-pyrrolidine-N-yl-2,3-difluorophenyl)-5-ethylthiazole-2-yl, 4-(2-(pyrrolidine-N-yl)thiazole-4-yl)thiazole-2-yl, 4-(4,5-benzo-2,1,3-oxadiazole-5-yl)thiazole-2-yl, 4-(2-dimethlaminopyridine-5-yl)thiazole-2-yl, 4-(2-fluoropyridine-5-yl)thiazole-2-yl, 4-((4-methylpiperazine-N-yl)pyridine-6-yl)thiazole-2-yl, 4-(3-fluoro-2-methylpyridine-6-yl)thiazole-2-yl, or wherein $R^1$ and $R^2$ are both methyl, D, $R^3$, $R^4$ and $R^5$ are all H, n is 2 and Ar-Cy is 3-(2-methylpyrimidine-4-yl)phenyl or wherein $R^1$ and $R^2$ are both methyl, $R^3$, $R^4$ and $R^5$ are all H, D is trifluoromethyl, n is 2 and Ar-Cy is 4-(4-chlorophenyl)thiazole-2-yl.

d) Any one or more of the compounds described in WO2009/152261 A1;

e) Any one or more compounds of structure I wherein $R^1$ and $R^2$ are both methyl, D, $R^3$, $R^4$ and $R^5$ are all H, n is 1 and Ar-Cy is any one of 4-phenylthiazole-2-yl, 4-(4-bromophenyl)thiazole-2-yl, 2- or 4-(N-morpholinyl)phenyl, 4-(N-piperidinyl)phenyl, 1-phenyl-3-methylpyrazole-5-yl, 4-(3,4-dimethylphenyl)thiazole-2-yl, 4-(4-ethylphenyl)thiazole-2-yl, 4-(2,4,6-trimethylphenyl)thiazole-2-yl, 4-(4-n-propylphenyl)thiazole-2-yl, 4-(4-chlorophenyl)-5-methylthiazole-2-yl, 4-phenylphenyl, 2-(N-pyrrolidinyl)phenyl, 4-(N-azacycloheptyl)phenyl, 4-phenyl-5-ethylthiazole-2-yl, 2- or 4-cyclopentylphenyl, or wherein $R^2$ is methyl, $R^1$, D, $R^3$, $R^4$ and $R^5$ are all H, n is 1 and Ar-Cy is 4-cyclopentylphenyl.

f) Any one or more of the compounds described in WO2007/073505 A1;

g) Any one or more compounds of structure I wherein $R^1$ and $R^2$ are both methyl, D, $R^3$, $R^4$ and $R^5$ are all H, n is 1 and Ar-Cy is any one of 4-phenylthiazole-2-yl, 4-(4-bromophenyl)thiazole-2-yl, 2- or 4-(N-morpholinyl)phenyl, 4-(N-piperidinyl)phenyl, 1-phenyl-3-methylpyrazole-5-yl, 2-(2-benzimidazolyl)phenyl, 4-(3,4-dimethylphenyl)thiazole-2-yl, 4-(4-ethylphenyl)thiazole-2-yl, 4-(2,4,6-trimethylphenyl)thiazole-2-yl, 4-(4-n-propylphenyl)thiazole-2-yl, 4-(4-chlorophenyl)-5-methylthiazole-2-yl, 4-phenylphenyl, 2-(N-pyrrolidinyl)phenyl, 4-(N-azacycloheptyl)phenyl, 4-phenyl-5-ethylthiazole-2-yl, h) Any one or more of the compounds described in WO2009/002933 A1;

i) A compound of structure I wherein $R^1$ and $R^2$ are both methyl, D, $R^3$, $R^4$ and $R^5$ are all H, n is 1 and Ar-Cy is 4-(4-diethylaminophenyl)thiazole-2-yl.

j) Any one or more of the compounds described in WO2009/140519 A1;

k) a compound of the formula shown below, or a salt thereof:

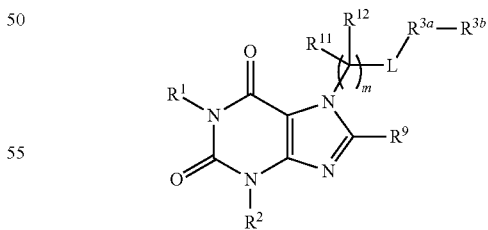

wherein, each of $R^1$ and $R^2$ is independently H, $C_1$-$C_6$ alkyl, $C_2$-$C_6$ alkenyl, or $C_2$-$C_6$ alkynyl, each of which is optionally substituted with 1-4 $R^5$; L is $NR^6SO_2$, $SO_2NR^6$, $OC(O)NR^6$, $NR^6C(O)O$, $NR^6C(O)NR^6$, $NR^6C(O)$, $C(O)NR^6$, O, C(O), S, S(O), $S(O)_2$, $NR_6$, or $CH_2$, each of $R^a$ and R is independently cyclyl, heterocyclyl, aryl, heteroaryl, each of which is optionally substituted with 1-4 $R^7$; each of $R^{11}$ and $R^{12}$ is, independently, H, $C_1$-$C_6$ alkyl, $C_2$-$C_6$ alkenyl, or $C_2$-$C_6$ alkynyl, halo, hydroxyl, alkoxy, amino, akylamino, thiol, alkylthiol, nitro, or cyano, each of which is optionally substituted with 1-2 R; each R is independently halo, hydroxyl, alkoxy, amino, alkylamino, dialkylamino, cyano, nitro, amido, alkylamido, dialkylamido, thioyl, sulfonyl, cyclyl, heterocyclyl, aryl, or heteroaryl; each $R^6$ is independently H, $C_1$-$C_6$ alkyl, $C_1$-$C_6$ alkenyl, hydroxy$C_1$-$C_6$ alkyl, alkoxy$C_1$-$C_6$ alkyl, cyanoalkyl, haloalkyl, arylalkyl, S(O) alkyl, acyl, amino, amidyl, or $S(O)_2H$, aryl, alkoxyaryl; each $R^7$ is independently $C_1$-$C_6$ alkyl, $C_2$-$C_6$ alkenyl, or $C_2$-$C_6$ alkynyl, halo, hydroxyl, alkoxy, oxo, aryl, heteroaryl, cyclyl, heterocyclyl, arylalkyl, heteroarylalkyl, cyclylalkyl, heterocyclylalkyl, aryloxy, arylalkoxy, amino, akylamino, dialkylamino, thioyl, alkylthioyl, sulfonyl, sulfonamidyl, amido, hydroxyl alkoxyl, alkoxy —C(O)OH, —C(O)Oalkyl, urea, sulfonylurea, acyl, nitro, cyano, each of which is optionally substituted with 1-3 R; each $R^8$ is independently $C_1$-$C_6$ alkyl, $C_2$-$C_6$ alkenyl, or $C_2$-$C_6$ alkynyl, aryl, heteroaryl, cyclyl, halo, hydroxyl, alkoxy, oxo, aryloxy, amino, akylamino, dialkylamino, C(O)OH, —C(O)Oalkyl, thioyl, sulfonyl, sulfonamidyl, amido, urea, sulfonylurea, acyl, nitro, cyano, cyclyl, heterocyclyl, aryl, or heteroaryl; $R^9$ is H, $C_1$-$C_6$ alkyl, $C_2$-$C_6$ alkenyl, or $C_2$-$C_6$ alkynyl, halo, $C_1$-$C_6$ haloalkyl, hydroxyl, alkoxy, aryloxy, arylalkoxy, amino, akylamino, dialkylamino, thioyl, alkylthioyl, sulfonyl, sulfonamidyl, amido, urea, sulfonylurea, acyl, nitro, cyano, each of which is optionally substituted with 1-3 $R^8$; and m is 1, 2, 3, 4, 5, or 6.

l) Any one or more compounds of structure I wherein $R^1$ and $R^2$ are both methyl, D, $R^3$, $R^4$ and $R^5$ are all H, n is 1 and Ar-Cy is any one of 4-(4-bromophenyl)-6-trifluoromethylpyrimidine-2-yl, 4-(3,4-dimethoxyphenyl)thiazole-2-yl, 4-(2,4-dimethylphenyl)thiazole-2-yl, 4-(2-fluorophenyl)thiazole-2-yl, 4-(3,4-difluorophenyl)-5-methylthiazole-2-yl, 4-(3,4-methylenedioxyphenyl)thiazole-2-yl, 4-(4-methoxynaphth-1-yl)thiazole-2-yl, 4-(benzo-2-piperidino)thiazole-2-yl, 4-(3-chloro-4-methoxyphenyl)thiazole-2-yl, 4-(4-ethoxyphenyl)-5-methylthiazole-2-yl, 4-(4-methylcarbonylaminophenyl)thiazole-2-yl, 4-(4-bromophenyl)-5-methylthiazole-2-yl, 4-(4-(2-methoxyethyl)phenyl)thiazole-2-yl, 4-(4-methyl-3-nitrophenyl)thiazole-2-yl, 4-(4-t-butylcarbonylaminophenyl)thiazole-2-yl, 4-phenyl-5-(1-methylimidazole-2-yl)thiazole-2-yl, 4-(4-(difluoromethoxy)phenyl)-5-methylthiazole-2-yl, 4-(2,5-diethoxyphenyl)thiazole-2-yl, 4-(4-fluorophenyl)-5-methylthiazole-2-yl, 4-phenyl-5-methylcarbonylthiazole-2-yl, 4-(3-chloro-4-fluorophenyl)thiazole-2-yl, 4-(3-fluorophenyl)thiazole-2-yl, 4-(3-methoxyphenyl)thiazole-2-yl, 4-(2-ethoxyphenyl)thiazole-2-yl, 4-(3-chlorophenyl)thiazole-2-yl, 4-(2-methoxyphenyl)thiazole-2-yl, 4-(2-bromophenyl)thiazole-2-yl, 4-(4-(dimethylamino)phenyl)thiazole-2-yl, 4-(2-chlorophenyl)thiazole-2-yl, 4-(4-methoxyphenyl)thiazole-2-yl, 4-(3-bromophenyl)thiazole-2-yl, 4-(4-methylcarbonylamino-2-fluorophenyl)thiazole-2-yl, 4-(4-isopropoxyphenyl)thiazole-2-yl, 4-(2,3,4-trichlrophenyl)thiazole-2-yl, 4-(3-chloro-4-methoxyphenyl)thiazole-2-yl, 4-(3-fluoro-4-chlorophenyl)thiazole-2-yl, 4-(3-ethoxyphenyl)thiazole-2-yl, 4-(3-nitrophenyl)thiazole-2-yl, 4-(4-phenylphenyl)thiazole-2-yl, 4-(2,4-dimethoxyphenyl)thiazole-2-yl, 4-(2,4-dimethylphenyl)thiazole-2-yl, 4-(4-cyanophenyl)thiazole-2-yl, 4-(4-ethylphenyl)thiazole-2-yl, 4-(2-methylphenyl)thiazole-2-yl, 4-(2-bromo-5-ethoxyphenyl)thiazole-2-yl, 4-(2-chloro-4-ethoxyphenyl)thiazole-2-yl, 4-(2-chloro-4-ethoxy-5-bromophenyl)thiazole-2-yl, 4-(2-pyridyl)thiazole-2-yl, 4-(2-hydroxylethoxy)phenyl)thiazole-2-yl, 4-(3-(2-hydroxylethoxy)phenyl)thiazole-2-yl, 4-(2,6-dichlorophenyl)thiazole-2-yl, 4-(3-methylphenyl)thiazole-2-yl, 4,5-bis(4-methylphenyl)oxazole-2-yl, 4,5-diphenyloxazole-2-yl, 4-(4-pyridyl)thiazole-2-yl, 4-(2-(2-hydroxyethoxy)phenyl)thiazole-2-yl, 4-(3,4-dichlorophenyl)-5-methylthiazole-2-yl, 4-(2,4,6-trichlorophenyl)thiazole-2-yl, 4-(4-ethoxyphenyl)-5-phenylthiazole-2-yl, 4-(4-chloro-3-ethoxyphenyl)thiazole-2-yl, 4-(3,4,5-trichlorophenyl)thiazole-2-yl, 2-(4-pyridyl)1,3,4-thiadiazole-5-yl, 4-(2-(2-hydroxyethoxy)-5-bromophenyl)thiazole-2-yl, 3-(benzoxazole-2-yl)-2-methylphenyl, 4-(2,3-dichlorophenyl)-5-ethylthiazole-2-yl, 4-(3-trifluoromethylphenyl)thiazole-2-yl, 4-(3,4-dichlorophenyl)-5-phenylthiazole-2-yl, 4-(3,4-dichlorophenyl)-5-(4-methylphenyl)thiazole-2-yl, 1-phenyl-3-(4-methylphenyl)pyrazole-5-yl, 3-(4-fluorophenyl)pyrazole-5-yl, 4,5-bis(3,4-dichlorophenyl)thiazole-2-yl, 5-phenylthiazole-2-yl, 5-(4-chlorophenyl)thiazole-2-yl, 4-(4-trifluoromethylphenyl)thiazole-2-yl, 4-(4-methylsulfonylphenyl)thiazole-2-yl, 4,5-bis(2-furyl)thiazole-2-yl, 4-(4-chlorophenyl)oxazole-2-yl, 4-(4-trifluoromethoxyphenyl)thiazole-2-yl, 3-(4-chlorophenyl)pyrazole-2-yl, 2-(4-chlorophenyl)-1,3,4-oxadiazole-5-yl, 3-phenylpyrazole-5-yl, 5-(4-methylphenyl)thiazole-2-yl, 4-(4-chlorophenyl)-5-ethylthiazole-2-yl, 4-(4-nitrophenyl)thiazole-2-yl, 4-(4-aminophenyl)thiazole-2-yl, 4-(4-ethoxylphenyl)-5-methylthiazole-2-yl, 4-(4-diethylamino-3-fluorophenyl)thiazole-2-yl, 3-(thiophene-2-yl)pyrazole-5-yl, 4-(4-chlorophenyl)-5-fluorothiazole-2-yl, 4-(4-chlorophenyl)-5-aminothiazole-2-yl, 2-(pyrrole-N-yl)phenyl, 2-(indole-2-yl)phenyl, 4-(benzimidazoloneyl)thiazole-2-yl, 2-chlorophenylpyrid-4-yl, 3-(4-chlorophenyl)phenyl, 4-(4-diethylamino-3-chlorophenyl)thiazole-2-yl, 5-(4-ethoxyphenyl)thiazole-2-yl, 3-(4-chlorophenyl)-5-pyridyl, 4-(3,4-dichlorophenyl)-5-isopropylthiazole-2-yl, 4-(4-diethylamino-2-fluorophenyl)thiazole-2-yl, 4-(4-(N-pyrrolidinyl)-3-bromophenyl)thiazole-2-yl, 4-(4-fluoro-3-N-morpholinylphenyl)thiazole-2-yl, 2-(4-chlorophenyl)pyrazine-6-yl, 4-(2,4,5-trichlorophenyl)thiazole-2-yl, 5-(4-diethylaminophenyl)thiazole-2-yl, 4-(1-ethoxynaphth-4-yl)thiazole-2-yl, 4-(2,3-dihydrobenzofuran-5-yl)thiazole-2-yl, 2-(3,4-dichlorophenyl)thiazole-4-yl, 4-phenyl-5-(4-ethoxyphenyl)imidazole-2-yl, 4-(4-(N-piperidinyl)phenyl)thiazole-2-yl, 4-(3-diethylaminophenyl)thiazle-2-yl, 2-(benzothiazole-2-yl)phenyl, 4-(3-(N-piperidinyl)phenyl)thiazle-2-yl, 4-(3-dimethylaminophenyl)thiazole-2-yl, 4-(4-chlorophenyl)pyridine-2-yl, 3-(4-diethylaminophenyl)phenyl, 4-(4-ethoxyphenyl)pyrazole-2-yl, 4-(4-ethoxyphenyl)-5-methylpyrazole-2-yl, 4(N-acetyl-2,3-dihydroindole-5-yl)thiazole-2-yl, 4-(3,4-dichlorophenyl)pyrimidine-2-yl, 3-(thiazole-2-yl)phenyl, 4-(quinoline-2-yl)thiazole-2-yl, 4-(4-diethylamino-3,5-difluorophenyl)thiazole-2-yl, 4-(3-(N-pyrrolidinyl)phenyl)thiazole-2-yl, 4-(4-aminocarbonylaminophenyl)thiazole-2-yl, 4-(4-chlorophenyl)-5-methoxylthiazole-2-yl, 4-(4-(diethylaminosulfonyl)phenyl)thiazole-2-yl), 4-(4-(dimethylaminosulfonyl)phenyl)thiazole-2-yl), 4-(dihydrobenzoxazine-3-one-6-yl)thiazole-2-yl, 4-(3,4-dichlorophenyl)imidazole-2-yl, 4-(4-ethoxyphenyl)oxazole-2-yl, 4-(4-chlorophenyl)oxazole-2-yl, 3-(4-ethylthiazole-2-yl)phenyl, 3-(5-ethylthiazole-2-yl)phenyl, 3-(4-methylthiazole-2-yl)phenyl, 4-(4-diethylamino-2-chlorophenyl)thiazole-2-yl, 4-(4-diethylamino-2, 5-difluorophenyl)thiazole-2-yl, 4-(3-trifluoromethoxyphenyl)thiazole-2-yl, 2-(4-chlorophenyl)pyrid-6-yl, 3-(4-diethylamino-3-fluorophenyl)phenyl, 4-(4-diethylamino-2,3-difluorophenyl)thiazole-2-yl, 4-(4-(N-piperidinylsulfonyl)phenyl)thiazole-2-yl, 4-(N-acetylindole-5-yl)thiazole-2-yl, 4-(2-ethoxynaphth-1-yl)thiazole-2-yl, 1-(phenylmethyl)-4-(3,4-diphenyl)imidazole-2-yl, 4-(N-ethyl-2,3-dihydroindole-5-yl)thiazole-2-yl, 3-(4- chlorophenyl)1,2,4-thiadiazole-5-yl, 4-(N-acetyl-2,3-dihydroindole-6-yl)thiazole-2-yl, 4-(N-ethylindole-5-yl)thiazole-2-yl, 3-(4-chlorophenyl)thiophene-5-yl, 1-(4-chlorophenyl)1,2,4-triazole-3-yl, 1-phenylpyrazole-4-yl, 4-(N-acetylindole-6-yl)thiazole-2-yl, 4-N-methyl-2,3-dihydroindole-5-yl)thiazole-2-yl, 4-(4-diethylamino-2-chloro-5-fluorophenyl)thiazole-2-yl, 4-(3-dimethylaminosulfonylphenyl)thiazole-2-yl, 4-(3-methylsulfonylaminophenyl)thiazole-2-yl, 4-(3-diethylaminosulfonylphenyl)thiazole-2-yl, 2-(4-chlorophenyl-1,3,5-triazine-4-yl, 4-(4-(morpholin-N-ylsulfonyl)phenyl)thiazole-2-yl), 4-(4-(N-pyrrolidinosulfonyl)phenylthiazole-2-yl), 4-(4-chloro-3-diethylaminophenyl)thiazole-2-yl, 4-(4-chloro-3-trifluoromethylphenyl)thiazole-2-yl, 1-ethyl-4-(2,3-dichlorophenyl)imidazole-2-yl, 1-methyl-4-(2,3-dichlorophenyl)imidazole-2-yl, 2-(1-naphthyl)5-pyridyl, 2-(3,4-dichlorophenyl)5-pyridyl, 4-(4-chlorophenyl)-5-dimethylaminomethylthiazole-2-yl, 4-(3-diethylaminophenyl)-5-methylthiazole-2-yl, 4-(4-diethylamino-3-fluorophenyl)-5-ethylthiazole-2-yl, 4-(4-chlorophenyl)-5-(2-dimethylaminoethyl)thiazole-2-yl, 4-(4-trifluoromethyl-2-fluorophenyl)thiazole-2-yl, 4-(3-trifluoromethyl-5-fluorophenyl)thiazole-2-yl, 4-(4-trifluoromethyl-3-fluorophenyl)thiazole-2-yl, 4-(3-trifluoromethyl-4-fluorophenyl)thiazole-2-yl, 4-(3,4-dichlorophenyl)-5-methoxycarbonylthiazole-2-yl, 4-(1-bromo-2-ethoxynaphth-6-yl)thiazole-2-yl, 4-(3,4-dichlorophenyl)-5-methoxycarbonylmethylthiazole-2-yl, 1,5-dimethyl-4-(3,4-dichlorophenyl)imidazole-2-yl, N-(4-chlorophenyl)pyrrole-3-yl, 4-(3,4-dichlorophenyl)-5-aminocarbonylthiazole-2-yl, 4-(2-ethoxynaphth-6-yl)thiazole-2-yl, 4-(3,4-dichlorophenyl)-5-hydroxycarbonylmethylthiazole-2-yl, 4-(4-diethylamino-2,5-difluorophenyl)-5-ethylthiazole-2-yl, 4-(4-(N-pyrrolidinyl)-3-fluorophenyl)thiazole-2-yl, 4-(4-diethylamino-3-ethoxyphenyl)thiazole-2-yl, 4-(4-diethylamino-2-ethoxyphenyl)thiazole-2-yl, 4-(4-(N-pyrrolidinyl)-3-(trifluoromethyl)phenyl)thiazole-2-yl, 4-(4-diethylamino-3-trifluoromethylphenyl)thiazole-2-yl, 4-(1-n-butyl-4-(3,4-dichlorophenyl)imidazole-2-yl, 1-(4-chlorophenyl)imidazole-4-yl, 4-(2-indolyl)thiazole-2-yl, 5-(4-chlorophenyl)isoxazole-2-yl, 5-(4-chlorophenyl)1,2,4-oxadiazole-3-yl, 1-ethyl-5-methyl-4-(3,4-dichlorophenyl)imidazole-2-yl, 4-phenyl-5-(4-ethoxyphenyl)oxazole-2-yl, 2-naphthyl-5-pyridyl, 2-(4-chlorophenyl)oxazole-5-yl, 4-(3-methylethylaminophenyl)-5-ethylthiazole-2-yl, 4-(4-ethoxyl-3-diethylaminophenyl)thiazole-2-yl, 4-(4-diethylaminophenyl)-5-fluorothiazole-2-yl, 4-(4-(4-ethylpiperazine-1-yl)-3-trifluoromethylphenyl)thiazole-2-yl, 4-(3-ethoxycarbonylphenyl)thiazole-2-yl, 4-(4-(N-pyrrolidinyl)-3,4-difluorophenyl)thiazole-2-yl, 4-(4-chlorophenyl)-5-trifluoromethylthiazole-2-yl, 4-(4-diethylamino-3-cyanophenyl)thiazole-2-yl, 4-(2-ethoxynaphth-5-yl)thiazole-2-yl, 4-(4-chlorophenyl)isothiazole-3-yl, 4-(N-methylindole-5-yl)thiazole-2-yl, 4-(3,4-dichlorophenyl)-5-(2-hydroxyethyl)thiazole-2-yl, 4-(4-chlorophenyl)thiazole-2-yl in which case D is trifluoromethyl, 1-(4-chlorophenyl)1,2,3-triazole-4-yl, 4-(2H-imidazole-1-yl)phenyl)thiazole-2-yl, 4-(4-tetrazole-5-ylphenyl)thiazole-2-yl, 4-(4-methyl-4-methoxyphenylmethylaminophenyl)thiazole-2-yl, 4-(4-(N-pyrrolidinyl)-3,5-difluorophenyl)-5-fluorothiazole-2-yl, 4-(4-N-morpholinyl-3-trifluoromethylphenyl)thiazole-2-yl, 4-(4-(N-piperidinyl)-3-(trifluoromethyl)phenyl)thiazole-2-yl, 4-(4-nitrophenyl)-5-trifluoromethylphenyl)thiazole-2-yl, 4-(4-diethylamino-3-trifluoromethylphenyl)-5-trifluoromethylthiazole-2-yl, 4-(3-hydroxycarbonylphenyl)thiazole-2-yl, 4-(4-hydroxycarbonylphenyl)thiazole-2-yl, 4-(4-N-pyrrolidinyl-25-difluorophenyl)thiazole-2-yl, 4-(4-diethylamino-3-fluorophenyl)-5-fluorothiazole-2-yl, 4-(4-diethylamino-3-trifluoromethylphenyl)-5-trifluoromethylthiazole-2-yl, 4-(4-aminophenyl)-5-trifluoromethylthiazole-2-yl, 4-(4-(N-pyrrolidinyl)phenyl)thiazole-2-yl, 4-(4-(4-ethylpiperazine-1-yl)phenyl-2,5-difluorophenyl)thiazole-2-yl, 4-(4-diethylaminophenyl)-5-trifluoromethylthiazole-2-yl, 4-(4-diethylamino-3,5-difluorophenyl)-5-fluorothiazole-2-yl, 4-(4-(N-morpholinyl)-2,5-difluorophenyl)thiazole-2-yl, 4-(4-(N-piperidinyl)-2,5-difluorophenyl)thiazole-2-yl, 4-(4-(N-pyrazolyl)-3-fluorophenyl)thiazole-2-yl, 4-(4-chlorophenyl)-5-methylthiazole-2-yl, 3-(5-methylthiazole-2-yl)phenyl, 4-(1-ethoxylnaphth-3-yl)thiazole-2-yl, 5-(4-chlorophenyl)isothiazole-3-yl, 4-(5-benzofuryl)thiazole-2-yl, 3-(4-chlorophenyl)isoxazole-5-yl, 4-(3-N-pyrrolidinylcarbonylphenyl)thiazole-2-yl, 4-(4-diethylaminophenyl)-5-phenylthiazole-2-yl, 4-(3-N-morpholinylcarbonylphenyl)thiazole-2-yl, 4-(4-diethylaminophenyl)-5-trifluoromethylcarbonylthiazole-2-yl, 4-(4-diethylamino-3-fluorophenyl)-5-trifluoromethylthiazole-2-yl, 4-(4-ethylamino-3-fluorophenyl)-5-trifluoromethylthiazole-2-yl, 4-(4-diethylamino-3-fluoro-5-trifluoromethylphenyl)-5-trifluoromethylthiazole-2-yl, 4-(4-(2-dimethylaminoethoxy)-3-fluorophenyl)thiazole-2-yl, 4-(4-(N-pyrrolidinyl)phenyl)-5-ethylthiazole-2-yl, 2-(4-(N-pyrrolidinyl)-3-fluorophenyl)pyridin-5-yl, 4-(4-fluoro-3-9N-pyrrolidinyl0phenyl)thiazole-2-yl, 4-(4-diethylamino-3-(N-pyrrolidinyl)phenyl)thiazole-2-yl, 4-(4-(N-pyrrolyl)phenyl)-5-(trifluoromethyl)thiazole-2-yl, 2-(4-chlorophenyl)thiophene-5-yl, 4-(1-ethoxynaphth-5-yl)thiazole-2-yl, 1-(4-chlorophenyl)pyrazole-3-yl, 4-(4-(N-pyrrolidinyl)-2,5-difluorophenyl)-5-ethylthiazole-2-yl, 4-(4-(N-pyrrolidinyl)-3-trifluoromethylphenyl)-5-methylthiazole-2-yl, 4-(4-(N-piperidinyl)-3-trifluoromethylphenyl)-5-methylthiazole-2-yl, 4-4(4-chlorophenyl)-5-n-propylthiazole-2-yl, 4-(4-ethoxyl-2-(N-pyrrolidinyl)phenyl)thiazole-2-yl, 4-(4-chloro-2-(N-pyrrolidinyl)phenyl)thiazole-2-yl, 4-(4-(N-pyrrolidinyl)phenyl)-5-fluorothiazole-2-yl, 4-(2-chloropyridine-5-yl)thiazole-2-yl, 2-(4-(N-pyrrolidinyl)phenyl)pyridine-5-yl, 4-(4-(N-pyrrolidinyl)-3-fluorophenyl)-5-ethylthiazole-2-yl, 4-(2-chloropyridine-3-yl)thiazole-2-yl, 4-(4-(2-methylpyrrolidine-1-yl)-3-fluorophenyl)thiazole-2-yl, 4-(4-(N-pyrrolidinyl)-3-(trifluoromethyl)phenyl)-5-n-propylthiazole-2-yl, 4-(4-diethylamino-2-chlorophenyl)-5-ethylthiazole-2-yl, 4-ethyl-5(4-chlorophenyl)thiazole-2-yl, 4-4(3,4-dichlorophenyl)-5-aminothiazole-2-yl, 4-(6-chloroquinoline-3-yl)thiazole-2-yl, 4-(2,4-bis(N-pyrrolidinyl)phenyl)thiazole-2-yl, 4-(4-(2,5-dimethylpyrrolidine-1-yl)3-fluorophenyl)thiazole-2-yl, 4-benzothiophene-3-ylthiazole-2-yl, 4-(4-diethylaminophenyl)-5-ethylthiazole-2-yl, 4-(4-methylaminophenyl)thiazole-2-yl, 4-(2,6-diethoxy-3-bromophenyl)thiazole-2-yl, 2-(thiophene-2-yl)phenyl, 2-(pyrrolidone-N-yl)phenyl, 1-phenyl-3-t-butylpyrazole-5-yl, 4-(4-(1-ethyltetrazolone-4-yl)phenyl)thiazole-2-yl, 4-(4-diethylaminocarbonylphenyl)-5-phenylthiazole-2-yl, 4-(4-(N-pyrrolyl)phenyl)-5-(trifluoromethyl)thiazole-2-yl, 4-(pyrimidine-5-yl)thiazole-2-yl, 4-(4-(N-morpholinyl)-3-fluorophenyl)-5-n-propylthiazole-2-yl, 4-(2-fluoropyrine-4-yl)thiazole-2-yl, 4-(2-fluoropyrine-3-yl)thiazole-2-yl, 4-(4-(N-azacycloheptyl)-3-fluorophenyl)thiazole-2-yl, 4-(2-chloropyridine-4-yl)thiazole-2-yl, 4-(2-methoxypyridine-5-yl)thiazole-2-yl, 4-(3-fluoropyrine-4-yl)thiazole-2-yl, 4-(3,4-dichlorophenyl)-5-nitrothiazole-2-yl, 4-(N-methyl-2,3-dihydroindole-6-yl)thiazole-2-yl, 4-(8-chloroquinoline-3-yl)thiazole-2-yl, 4-(4-(N-pyrrolidinyl)-2,3-difluorophenyl)-

5-ethylthiazole-2-yl, 4-(2-(N-pyrrolidinyl)thiazole-4-yl)thiazole-2-yl, 4-(benzofurazan4-yl)thiazole-2-yl, 4-(2-dimethylaminopyridine-5-yl)thiazole-2-yl, 4-(2-fluoropyridine-5-yl)thiazole-2-yl, 4-(2-(4-methylpiperidine-1-yl)pyiridine-6-yl)thiazole-2-yl, 4-(3-fluoro-2-methylpyridine-6-yl)thiazole-2-yl.

m) Any one or more of the compounds described in WO2009/140517 A1;

n) a compound of the formula below or a salt thereof,

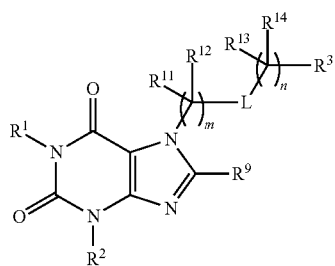

wherein each of $R^1$ and $R^2$ is, independently, H, $C_1$-$C_6$ alkyl, $C_2$-$C_6$ alkenyl, or $C_2$-$C_6$ alkynyl, each of which is optionally substituted with 1-4 $R^5$; L is $NR^6SO_2$, $SO_2NR^6$, $C(O)NR^6$, $NR^6C(O)$, $OC(O)NR^6$, $NR^6C(O)O$, $NR^6C(O)NR^6$, S, S(O), S(O)2, $NR^6$, $CH_2$, O, $C(O)NS(O)2$, $S(O)2NC(O)$, heteroaryl, or cyclyl; R is $C_4$-$C_{14}$ cyclyl, heterocyclyl, aryl, or heteroaryl, each of which is optionally substituted with 1-4 $R^7$; each $R^5$ is independently halo, hydroxyl, alkoxy, thiol, alkylthio, amino, alkylamino, dialkylamino, cyano, nitro, amido, alkylamido, dialkylamido, thioyl, sulfonyl, cyclyl, heterocyclyl, aryl, or heteroaryl; each $R^6$ is independently H, $C_1$-$C_6$ alkyl, $C_2$-$C_6$ alkenyl, $C_2$-$C_6$ alkynyl, aryl, arylalkyl, or acetyl; each $R^7$ is independently $C_1$-$C_6$ alkyl, $C_2$-$C_6$ alkenyl, $C_2$-$C_6$ alkynyl, cyclyl, heterocyclyl, aryl, heteroaryl, halo, hydroxyl, alkoxy, thiol, alkylthio, aryloxy, arylalkoxy, amino, akylamino, dialkylamino, thioyl, alkylthioyl, sulfonyl, sulfonamidyl, amido, urea, sulfonylurea, hydroxyl alkoxyl, alkoxy alkoxyl, acyl, nitro, or cyano, each of which is optionally substituted with 1-3 $R^8$; each $R^8$ is independently $C_1$-$C_6$ alkyl, $C_2$-$C_6$ alkenyl, or $C_2$-$C_6$ alkynyl, halo, hydroxyl, alkoxy, thiol, alkylthio, aryloxy, amino, akylamino, dialkylamino, thioyl, sulfonyl, sulfonamidyl, amido, urea, sulfonylurea acyl, nitro, cyano, cyclyl, heterocyclyl, aryl, or heteroaryl; $R^9$ is independently H, $C_1$-$C_6$ alkyl, $C_2$-$C_6$ alkenyl, or $C_2$-$C_6$ alkynyl, halo, hydro xyl, alkoxy, aryloxy, arylalkoxy, amino, akylamino, dialkylamino, thioyl, alkylthioyl, sulfonyl, sulfonamidyl, amido, urea, sulfonylurea, acyl, nitro, cyano, and is optionally substituted with 1-3 $R^8$; each of $R''$-$R^{14}$ is, independently, H, $C_1$-$C_6$ alkyl, $C_2$-$C_6$ alkenyl, or $C_2$-$C_6$ alkynyl, halo, hydroxyl, alkoxy, amino, akylamino, thiol, alkylthiol, nitro, or cyano, each of which is optionally substituted with 1-2 $R^8$; each of m and n is, independently, 0, 1, 2, 3, 4, 5, or 6.

o) Any one or more, optionally all, of the compounds 7, 13, 17, 27, 28, 39, 42, 43, 44, 58, 65, 71 and 80, and also optionally 83, described hereinafter.

The following particular options may be used in conjunction with the first aspect, either individually or in any suitable combination.

$R^1$ and $R^2$ may, independently, be methyl or ethyl. They may both be methyl. $R^3$ and $R^4$ may both be H. They may both be alkyl, e.g. methyl or ethyl. One of $R^3$ and $R^4$ may be alkyl (e.g. methyl or ethyl) and the other H. $R^5$ may be hydrogen. It may be methyl or may be some other alkyl.

If Ar is a 6-membered ring, it may be 1,4-disubstituted. If Ar is a 5-membered ring it may be 1,3-disubstituted. Ar may be a ring which is not 1,2-disubstituted. In this context, "disubstituted" refers to substitution by Cy and $NR^5$.

Ar may be a disubstituted benzene ring (i.e. a phenylene ring), a disubstituted thiophene ring or a disubstituted nitrogen heterocycle having between 1 and 4 nitrogen atoms. It may be a 6 membered aromatic ring having between 0 and 2 nitrogen atoms. It may be a ring that is not a 2-thiazolyl ring. It may be a pyridazine ring, e.g. a pyridazin-3,6-diyl.

Cy may be a 5 or 6 membered aromatic ring having between 0 and 2 nitrogen atoms, 0 or 1 sulfur atoms and 0 or 1 oxygen atoms. Alternatively it may be piperazine. The piperazine may be substituted on both nitrogen atoms. Cy may contain no chlorine. It may be a group that is not a chlorophenyl group (optionally additionally substituted). In some embodiments compound I has no chlorine.

n may be 1.

D may be H.

The modulating may be inhibiting.

In a particular embodiment, $R^1$ and $R^2$ are both methyl, $R^3$, $R^4$, $R^5$ and D are all H and n is 1. In a specific instance of this embodiment, Ar is a 6-membered ring having 1 or 2 nitrogen atoms and having no substituents other than Cy and the amide nitrogen, these being in a 1,4-relationship on the ring.

The compound may have an $IC_{50}$ against STF3A of less than 10 micromolar, or less than 5 micromolar or less than 1 micromolar, or less than 0.1 micromolar.

The compound may not modulate, or may not inhibit, TRPA1. It may not inhibit TRPA1 at an $IC_{50}$ of <5 micromolar or at an $IC_{50}$ of <10 micromolar.

The first aspect also includes all enantiomers and diastereomers of the compound, as well as salts of the compounds. Suitable salts include pharmaceutically and/or veterinarially acceptable salts, for example the hydrochloride salts. The free bases of the compounds are also encompassed.

In a second aspect of the invention there is provided use of a compound as defined in the first aspect for modulating, optionally inhibiting, Wnt activity and/or porcupine activity. There is also provided a method of modulating, optionally inhibiting, Wnt activity (e.g. Wnt secretion) and/or porcupine activity comprising exposing cells, or a Wnt protein or a Wnt receptor, to a compound as defined in the first aspect. The cells may be cells that over-express Wnt protein. The method may be an in vitro method or it may be an in vivo method. Without wishing to be bound by theory, the inventors hypothesise that the compounds defined in the first aspect inhibit the secretion of Wnt proteins. The compounds of the invention are capable of inhibiting porcupine, which is essential and specific for the palmitoylation of Wnt proteins before secretion. Thus in an embodiment there is provided a method of inhibiting, Wnt secretion in a cell, said method comprising exposing said cell to a compound as defined in the first aspect. In another embodiment there there is provided a method of inhibiting Wnt secretion in a cell which over-expresses Wnt protein, said method comprising exposing said cell to a compound as defined in the first aspect.

In a third aspect of the invention there is provided use of a compound as defined in the first aspect for treatment of a disease or condition associated with Wnt pathway activity. The Wnt pathway activity may be excessive activity. This aspect also includes a method for treating said disease or condition, comprising administering to a subject in need thereof a therapeutically effective amount of the compound.

The subject may be a human or may be a non-human, e.g. a non-human mammal or other non-human animal.

The disease or condition may be selected from the group consisting of cancer, fibrosis, stem cell and diabetic retinopathy. The cancer may be a cancer characterised by abnormal, optionally high, Wnt activity.

In a fourth aspect of the invention there is provided use of a compound as defined in the first aspect for the manufacture of a medicament for the treatment of a disease or condition associated with abnormal, optionally high, Wnt pathway activity. The disease or condition may be selected from the group consisting of cancer, fibrosis, stem cell and diabetic retinopathy, rheumatoid arthritis, psoriasis and myocardial infarction. There is also provided a composition or medicament for the treatment of such a disease or condition, said composition or medicament comprising a compound as defined in the first aspect together with one or more pharmaceutically acceptable carriers, diluents or adjuvants.

The disease or condition may be a cancer, such as cervical, colon, breast, bladder, head and neck, gastric, lung, ovarian, prostate, thyroid, non-small-cell lung, as well as chronic lymphocytic leukemia, mesothelioma, melanoma, pancreatic adenocarcinoma, basal cell carcinoma, osteosarcoma, hepatocellular carcinoma, Wilm's tumour or medulloblastoma. The disease or condition may be a severe fibrotic disease, such as pulmonary fibrosis, liver fibrosis, skin fibrosis or renal fibrosis. It may be a degenerative disease. It may be a metabolic disease such as diabetic retinopathy.

In a fifth aspect of the invention there is provided a compound as defined in the first aspect for use in therapy.

In a sixth aspect of the invention there is provided a pharmaceutical composition comprising a compound according to the first aspect together with one or more pharmaceutically acceptable carriers, diluents or adjuvants.

In a seventh aspect of the invention there is provided an anhydrous form of the free base of 2-(1,3-dimethyl-2,6-dioxo-1,2,3,6-tetrahydro-7H-purin-7-yl)-N-(6-phenylpyridazin-3-yl)acetamide. There is also provided a pharmaceutical composition comprising said anhydrous free base, a method of treating or preventing a proliferative disorder comprising administering a therapeutically effective amount of said anhydrous free base to a subject in need thereof and use of said anhydrous free base either in the treatment of a proliferative disorder or in the manufacture of a medicament for the treatment of a proliferative disorder.

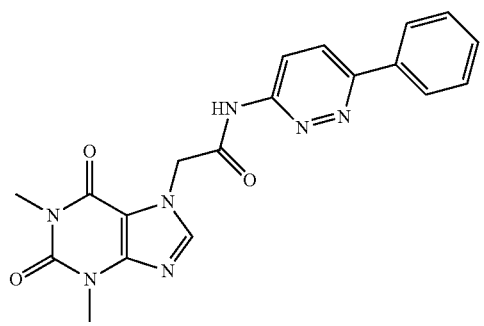

Figure 2:
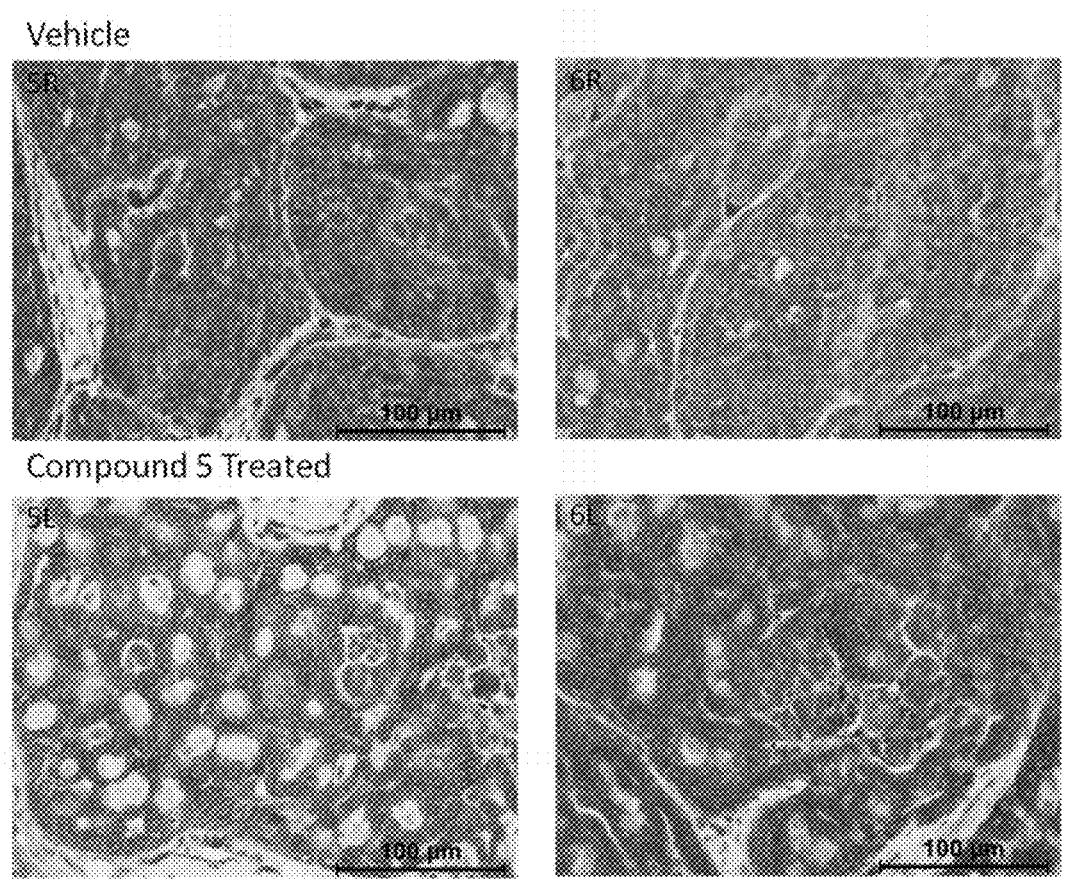

FIG. 2 shows images of tumours treated with Compound 5.

Figure 3A:
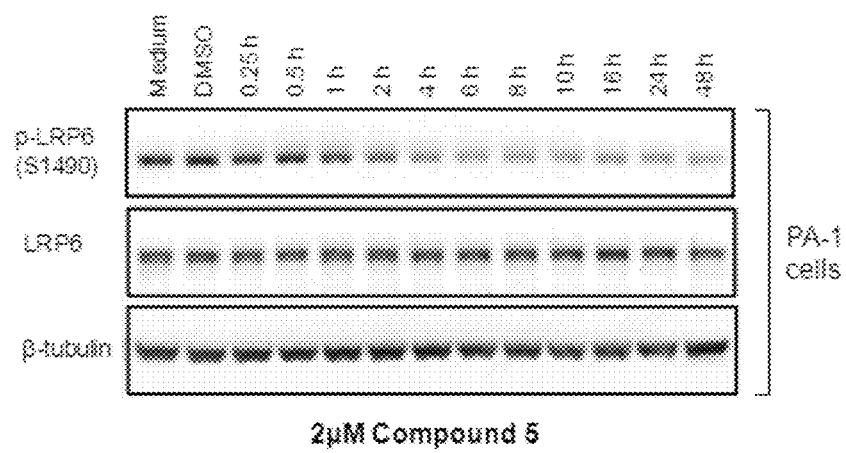
Figure 3B:
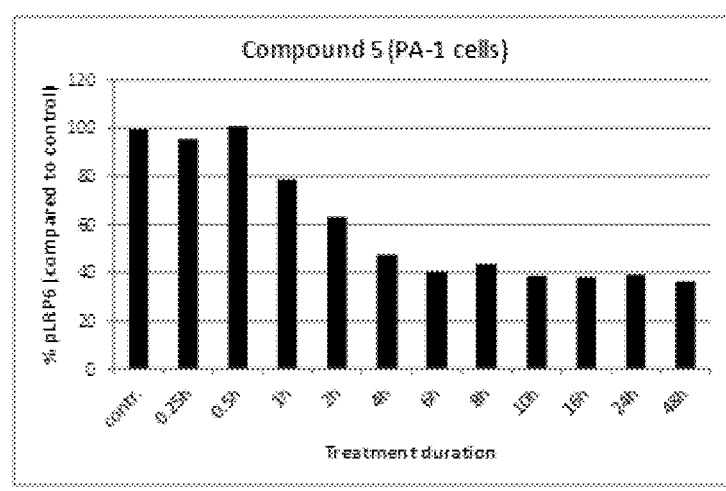

FIGS. 3A-3B show the time-course of p-LRP6 (Ser 1490) inhibition (in vitro) induced by porcupine inhibitors. FIG. 3A is a Western blot analysis of PA-1 teratocarcinoma cells treated with 2 µM of Compound 5, for the time points indicated with antibodies as indicated on the left. As a control, cells treated with either growth medium alone or the vehicle (DMSO) for 48 h were included. FIG. 3B is a densitometric analysis of pLRP6 relative to total LRP6.

Figure 4A:
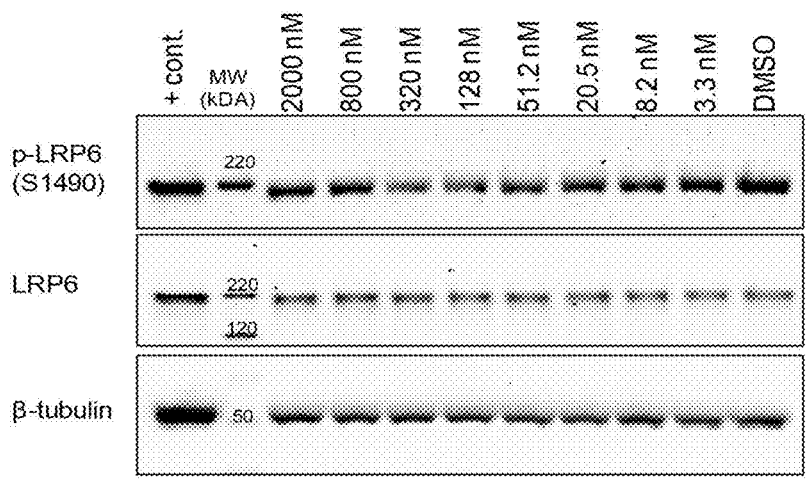
Figure 4B:
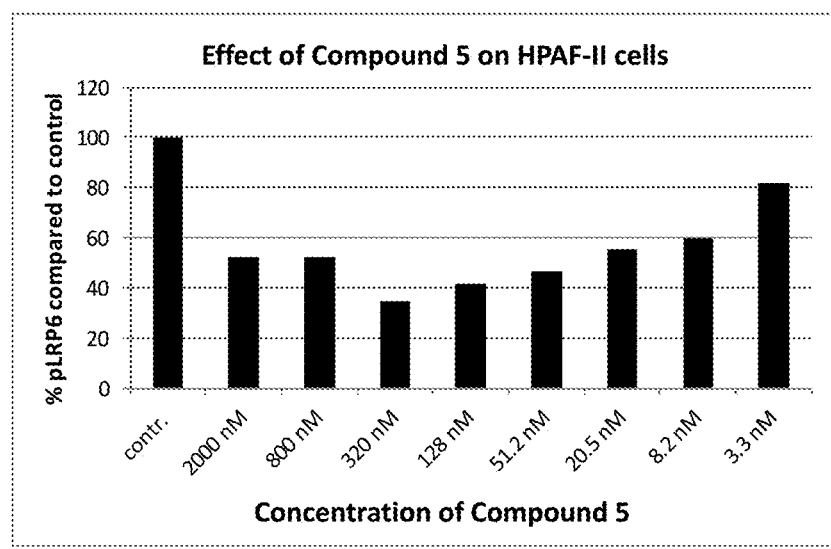

FIGS. 4A-4B show pLRP6 in vitro inhibition-dose titration. FIG. 4A is a Western blot analysis of HPAF-II pancreatic adenocarcinoma cells treated with the indicated doses of Compound 5 for 6 h with antibodies as indicated on the left. The positive controls are a cell lysate of untreated STF3A cells and cells treated with vehicle only (DMSO). FIG. 4B is a densitometric analysis of pLRP6 relative to total LRP6.

DESCRIPTION OF EMBODIMENTS

The invention relates to the preparation and the use of new compounds that modulate Wnt activity, to methods of using the compounds, as a single agent or in combination, for treating or preventing diseases and conditions associated with Wnt pathway activity, in particular having a dysfunction linked to Wnt signalling pathway i.e. cancer, fibrosis, stem cell and diabetic retinopathy. Thus the invention relates to a class of compounds that act as modulators of the Wnt pathway and to pharmaceutical compositions comprising these compounds and to their use for the preparation of a medicament for the treatment of diseases having a dysfunction linked to Wnt signalling pathway where Wnt plays a role in proliferation of cancer via multiple mechanisms, including a key role in stem cell maintenance. Dysfunction of the Wnt pathway is related to conditions including, but not limited to, cancers such as cervical, colon, breast, bladder, head and neck, gastric, lung, ovarian, prostate, thyroid, non-small-cell lung, as well as chronic lymphocytic leukemia, mesothelioma, melanoma, pancreatic adenocarcinoma, basal cell carcinoma, osteosarcoma, hepatocellular carcinoma, Wilm's tumour and medulloblastoma and other diseases with high Wnt expression such as fibrosis (including skin, idiopathic pulmonary, liver, renal interstitial, myocardial, infarct and liver) and diabetic retinopathy. Respiratory conditions, or respiratory tumours, may in certain embodiments not be conditions treated by the present invention.

Many of the compounds of the present invention are 1,3-dimethyl-3,7-dihydro-1H-purine-2,6-diones or 1,3-dimethyl-2,6-dioxo-1,2,3,6-tetrahydropurines and related compounds. The general structure of these is structure (I) as defined earlier. In this definition the following may apply.

Alkyl groups may be linear or may be branched. They may be C1 to C12 or may be more than C12. They may for example be C1 to C6, C1 to C3, C3 to C6 or C6 to C12, e.g. methyl, ethyl, propyl, isopropyl, butyl, isobutyl, tertiary butyl, pentyl, neopentyl, hexyl, octyl, isooctyl, decyl or dodecyl. In certain instances they may contain cyclic structures. Thus they may for example be, or may contain, cyclohexyl, methylcyclohexyl, isopropylcyclopentyl, cyclobutylethyl etc. In certain embodiments they are not cage structures such as adamantyl.

Aryl groups may be homoaromatic. They may be benzenoid. They may be monocyclic, bicyclic or polycyclic (i.e. contain more than 2 rings). They may comprise fused and/or unfused rings. They may, unless otherwise specified, have any suitable substitution pattern, e.g. ortho, meta, para.

Unless specified, they may have any appropriate number of substituents (e.g. a monocyclic aromatic may have from 1 to 5 substituents, a fused bicyclic aromatic may have from 1 to 7 substituents etc.).

Heteroaryl groups may have 1 heteroatom, or may have 2, 3 or 4 heteroatoms or in some cases more than 4. The heteroatom(s) are commonly selected (independently) from N, S and O, however in some instances other heteroatoms may be present. Heteroaryl groups typically have 5 or 6 ring atoms unless they are bicyclic or polycyclic. Unless otherwise specified, they may have any suitable substitution pattern and may have any appropriate number of substituents. Heteroaryl groups may be monocyclic or bicyclic or polycyclic. The fused rings may each be either a heteroaryl ring or a homoaryl ring, provided that at least one is heteroaryl.

Non-aromatic rings may, unless otherwise specified, be carbocyclic or may contain one or more heteroatoms, e.g. 1, 2, 3 or 4 heteroatoms. Each heteroatom may, independently, be N, S or O, or some other heteroatom. The rings may have from 4 to 8 ring atoms, commonly 5 or 6. Suitable examples include piperazinyl and morpholinyl rings. Group Cy in structure (I) may be, in some embodiments, an example of such rings.

The term "optionally substituted" signifies that one or more substituents may be present or there may be no substituents. Substituents may or may not be present on the above groups (alkyl, aryl, heteroaryl, non-aromatic rings). There may be 0, 1, 2, 3 or 4 or more than 4 substituents on a group, as dictated by the structure of the group. Possible substituents include halogens (e.g. fluorine, chlorine or bromine), alkyl groups, alkoxy groups (i.e. O-alkyl, where alkyl is as defined above), aryloxy groups (i.e. O-aryl, where aryl is as defined above), ester, amide or sulfonate ester groups (i.e. $CO_2R$, CONHR, $SO_3R$, where R is alkyl as defined above), however other substituents may additionally or alternatively be present. In cases where substituents are shown, the term "optionally substituted" indicates the possibility of additional substituents that are not shown. Thus for example in structure I, when it is stated that Ar is "optionally substituted", this indicates the possibility of further substituents additional to Cy and $NR^5$, but does not indicate the possibility that either Cy or $NR^5$ might be absent. Thus, for example, in cases where it is stated that Ar is a "disubstituted" aromatic ring, this should be taken to mean that there are only two substituents on the ring, i.e. no additional substituents other than Cy and the amide nitrogen. For example, the 1,4-phenylene group in compound 1 is regarded as "disubstituted".

In structures (I) and (II), n may be 1 to 5. It may be 1 to 3. It may be any one of 1, 2, 3, 4 or 5. Substituent D may be H, halogen, alkyl, cycloalkyl, aryl, or dialkylamino, each (other than H and halogen) being optionally substituted. Examples include hydrogen, chlorine, bromine, methyl, ethyl, propyl, cyclopropyl, phenyl, trifluoromethyl, dimethylamino, N-piperidinyl, N-piperazinyl, N-methyl-N'-piperazinyl etc. In many embodiments, n is 1.

In some cases, the substituents $R^3$ and $R^4$ are the same, and in others they are different. In the event that they are different, they give rise to stereochemistry at the carbon atom to which they are attached. In general the stereochemistry at that carbon (or at each carbon) may be (S) or (R). In the particular example where n is 1 and one of $R^3$ and $R^4$ is H and the other is an alkyl group, a preferred stereochemistry is as shown in structure (II), where Me represents the alkyl group. In cases where the alkyl group is methyl, this stereochemistry is particularly preferred.

Examples of group Ar in structure (I) include 1,4-phenylene, 2,5-pyridinediyl, 3,6-pyridazinediyl, 2,5-pyrazinediyl, 2,5-thiophenediyl, 2,4-thiophenediyl, 2,5-furandiyl, 2,4-furandiyl, etc. Examples of group Cy in structure (I) include phenyl, thiazole-2-yl, thiophene-2-yl, thiophene-3-yl, pyridine-1-yl, pyridine-2-yl, pyridine-3-yl, pyridazine-3-yl, pyridazine-4-yl, pyrimidine-2-yl, pyrimidine-4-yl, pyrimidine-4-yl, N-imidazolyl, 2-, 4- or 5-thiazolyl, 2-, 4- or 5-oxazolyl, N-morpholinyl or N' substituted N-piperazinyl. Suitable substituents on the N' position of the piperazinyl substituent include —C(=O)X, where X is t-butoxy, neopentyl, methyl, phenyl, p-chlorophenyl, benzyl, α,α-difluorobenzyl, chlorobenzyl, fluorobenzyl etc.

In some embodiments, $R^1$ and $R^2$ are the same. They may be both methyl. They may be both ethyl. In the latter case, Ar may be 1,4-phenylene and Cy may be thiophene-3-yl.

In some embodiments D is H. In other embodiments, D is methyl, cyclopropyl, trifluoromethyl, phenyl, dimethylamino, morpholin-N-yl, thiophene-3-yl or bromo. In the event that D is not H (e.g. is methyl, cyclopropyl, trifluoromethyl, phenyl, dimethylamino, morpholin-N-yl, thiophene-3-yl or bromo), Ar may be 1,4-phenylene and Cy may be thiophene-3-yl.

In some embodiments, n is 1 and in others it is 2 or 3. In the event that n is 2 or 3, Ar may be 1,4-phenylene and Cy may be thiophene-3-yl or thiazole-2-yl.

In some embodiments, $R^3$ and $R^4$ are either both H or both methyl. In other embodiments, one is H and the other is methyl or ethyl. In the event that they are not both H, Ar may be 1,4-phenylene. Alternatively, if they are not both H, either Ar is 1,4-phenylene or Cy is phenyl or either is thiazole-2-yl.

In some embodiments $R^5$ is H.

In some embodiments Ar is 1,4-phenylene and Cy is thiophene-3-yl or thiazole-2-yl. In particular embodiments Ar is 1,4-phenylene and Cy is thiophene-3-yl.

In a particular embodiment, $R^1$ and $R^2$ are both Me, D is H, n is 1 and $R^3$ and $R^4$ are both H. In this embodiment, it is preferred that if Ar is 1,4-phenylene, Cy is not thiophene-3-yl. In a variation of this embodiment, either $R^1$ and $R^2$ are not both methyl, or D is not H, or n is not 1, or $R^3$ and $R^4$ are not both H (optionally more than one, and in particular instances all, of these apply) and Ar is 1,4-phenylene and Cy is thiophene-3-yl or thiazole-2-yl (optionally Ar is 1,4-phenylene and Cy is thiophene-3-yl).

In some embodiments, any one or more, optionally all, of compounds 7, 13, 27. 28, 39, 42, 43, 44, 58, 65, 71, 80 and 83 as defined hereinafter may be excluded from the scope of the invention. In some embodiments, any one or more, optionally all, of compounds 8, 12, 55 and 85 may also be excluded.

In some embodiments, Ar and Cy are not both optionally substituted phenyl rings. In some embodiments, at least on of Ar and Cy is heteroaromatic or non-aromatic. In some embodiments at least one of Ar and Cy is heteroaromatic.

In some embodiments, if Ar is 1,4-phenylene or 2,5-pyridyl, Cy has no more than 1 ring nitrogen atom. In other embodiments, if Ar is a 5-membered ring, it is not oxazolediyl. In yet other embodiments, if Ar is a 5-membered ring, it may be thiophenediyl, e.g. thiophene-2,4-diyl. In the context of the present specification, reference to "if A then B" should be taken to indicate the possibilities either that A is not the case or that both A and B are the case. Therefore for example, the statement "if Ar is a 5-membered ring, it may be thiophenediyl" may be taken to mean that either Ar is not a 5-membered ring, or else Ar is a thiophenediyl ring. In such instances, Ar could be for example, a pyridinediyl ring, but could not be a furandiyl ring.

It will be understood that many (although not all) of the limitations set out above in various embodiments may be used together in combination, and the present invention explicitly contemplates such combinations where they are practicable.
Specific (but non-limiting) examples of the compounds of the present invention are set out below:
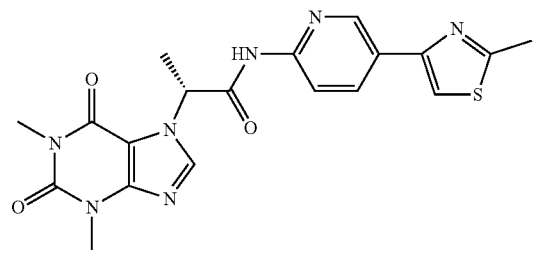
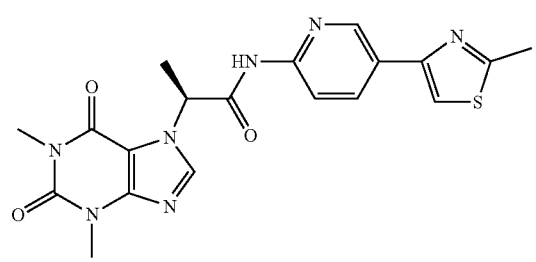
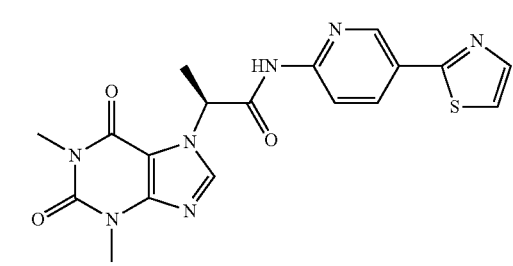
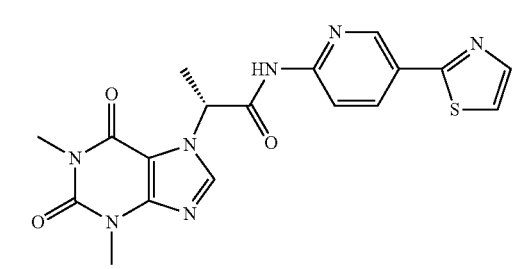
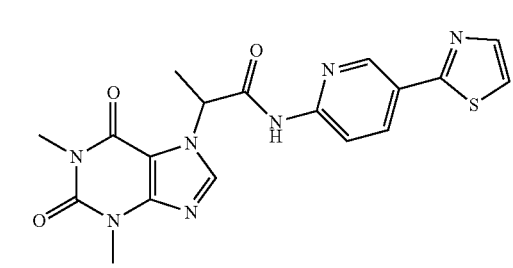
-continued
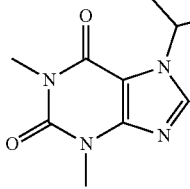
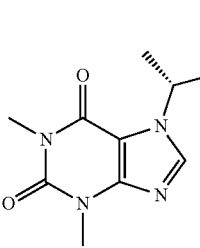
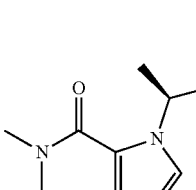
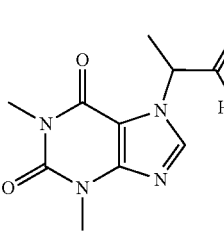
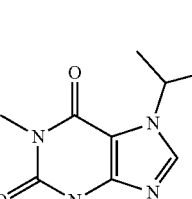
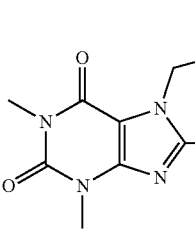

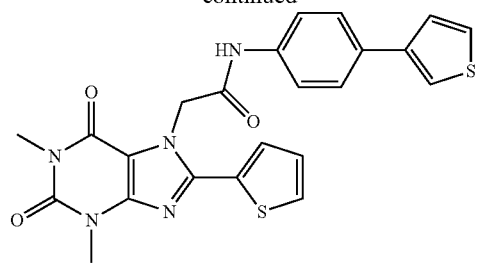
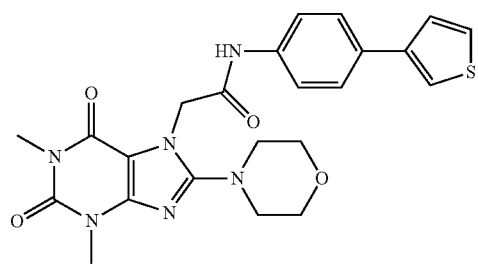
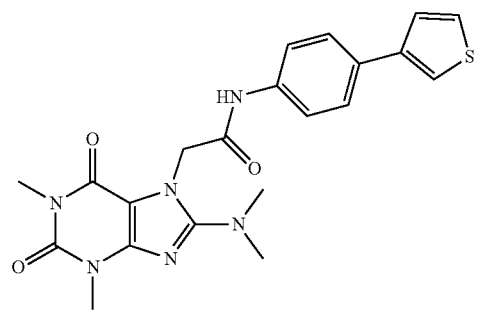
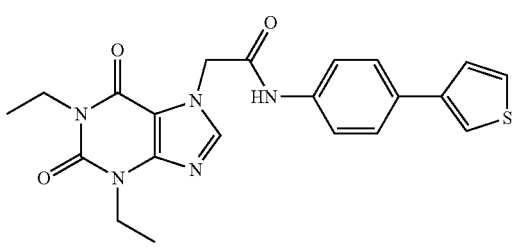
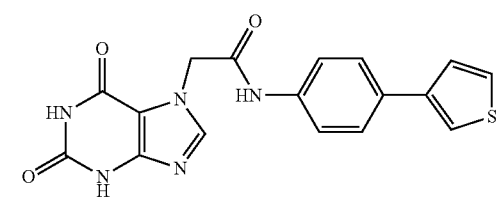
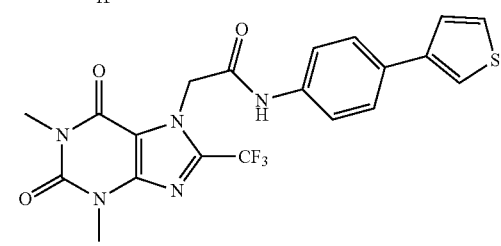
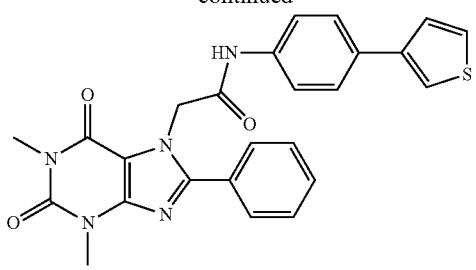
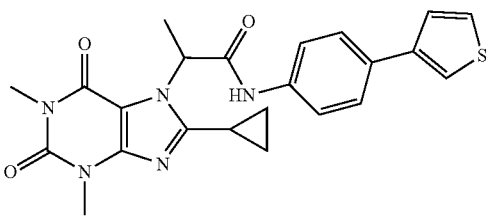
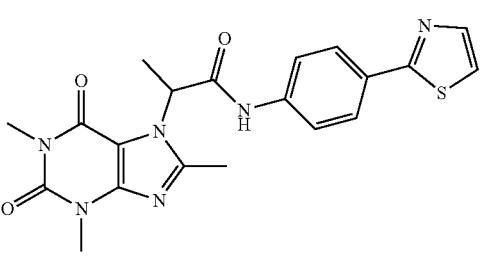
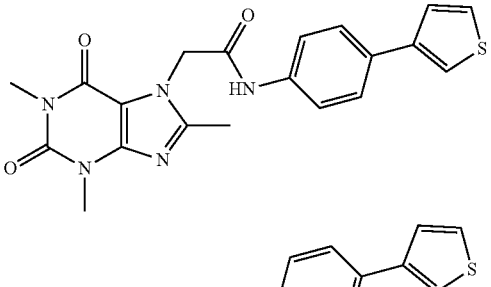
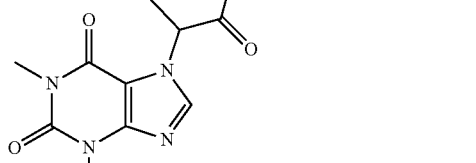
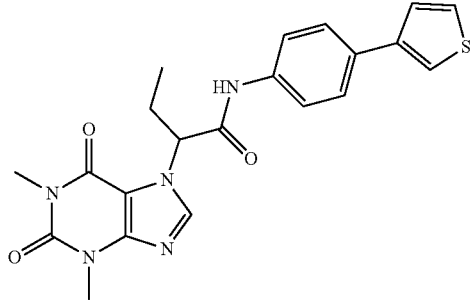

23
-continued
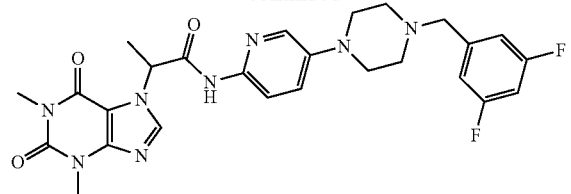
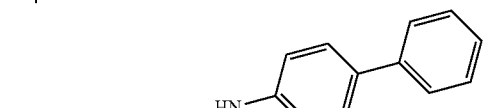
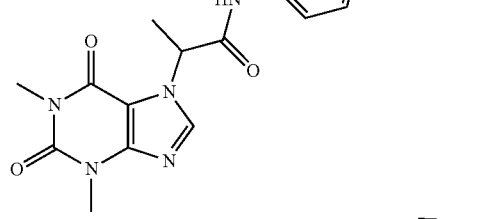
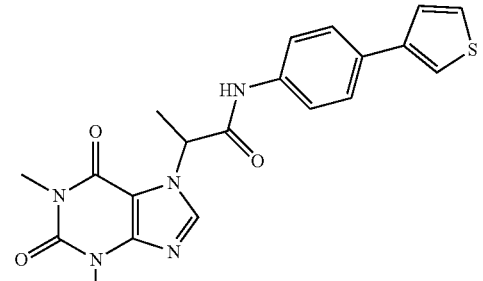
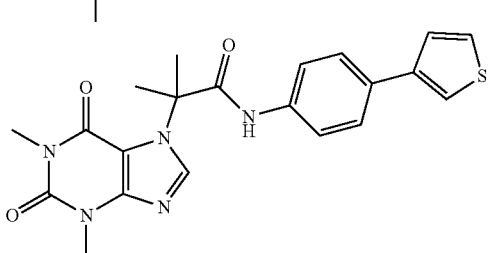
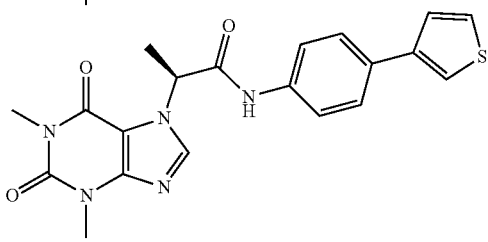
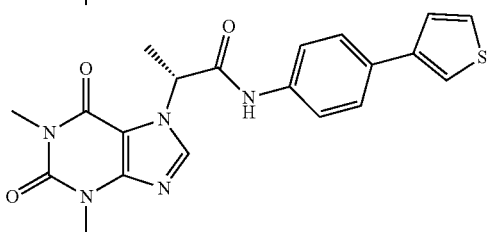
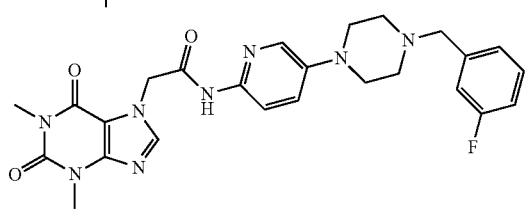
24
-continued
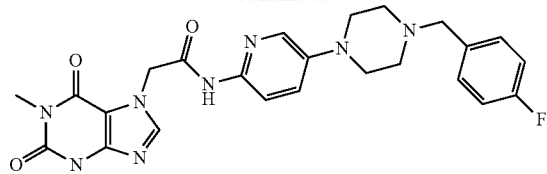
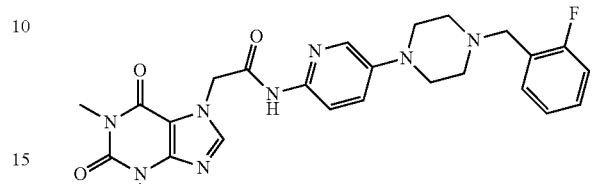
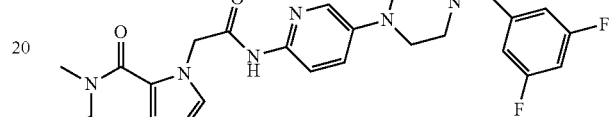
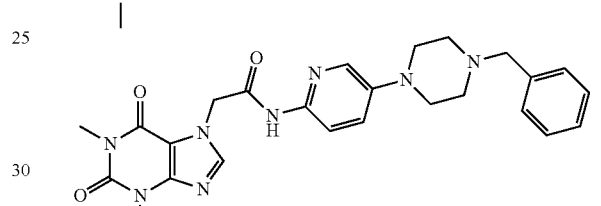
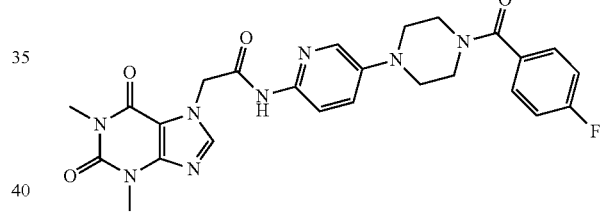
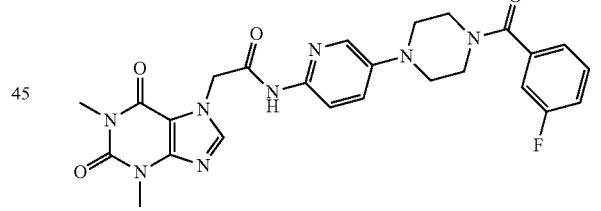
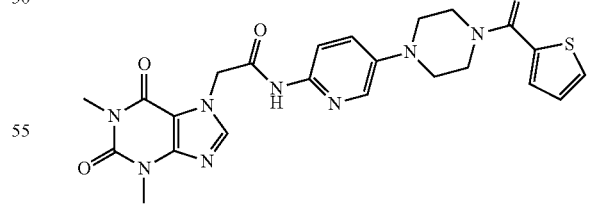
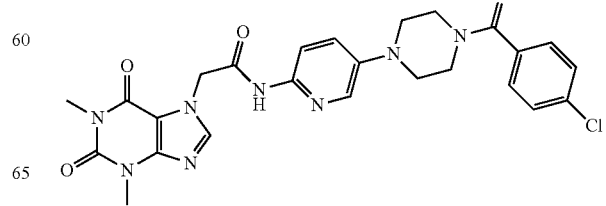

25
-continued
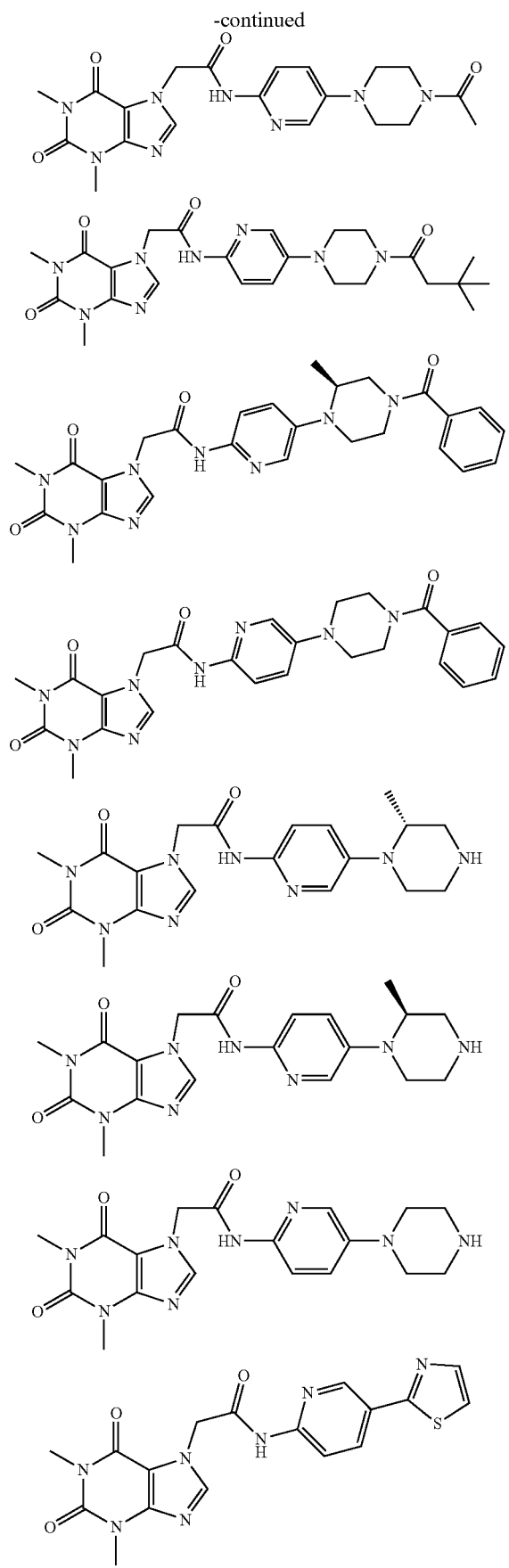
26
-continued
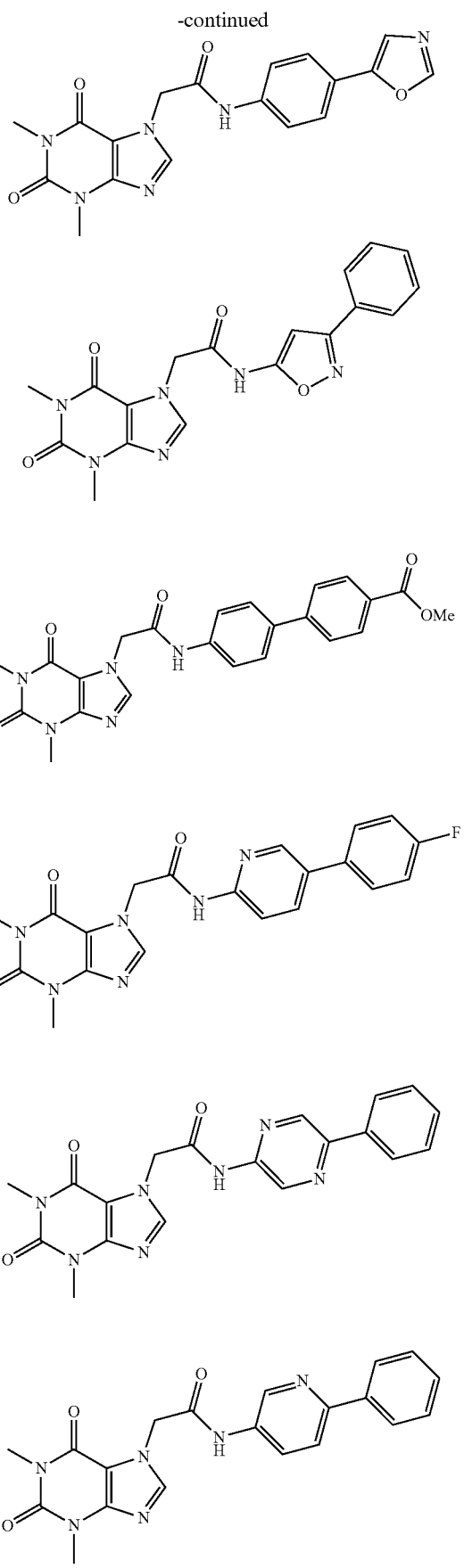

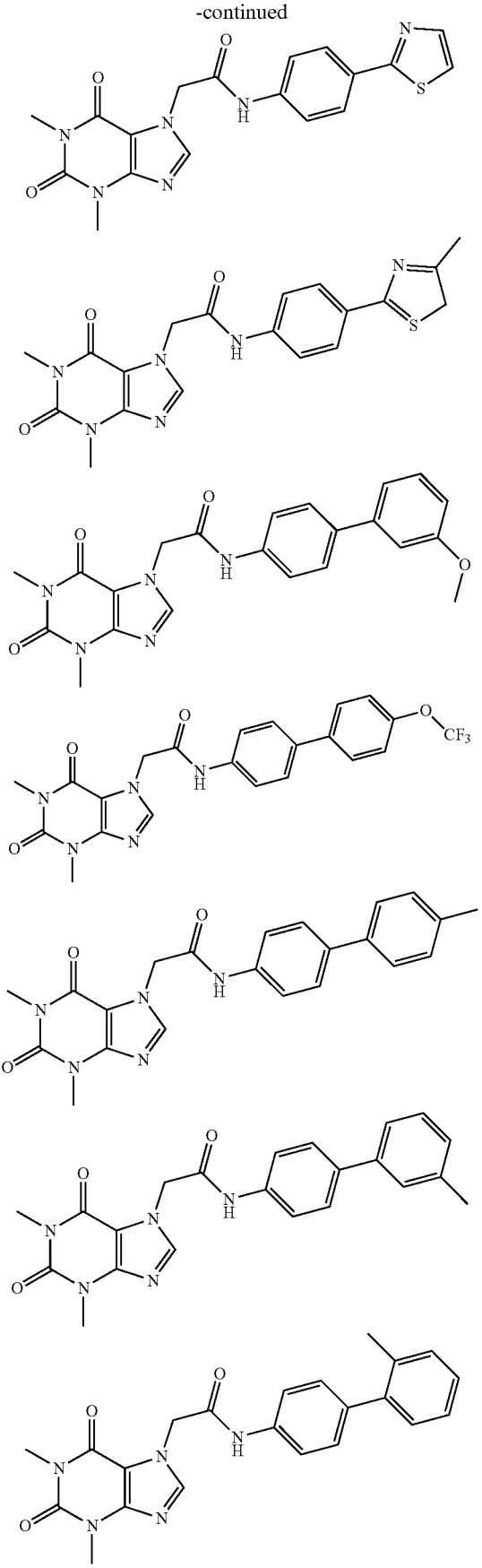
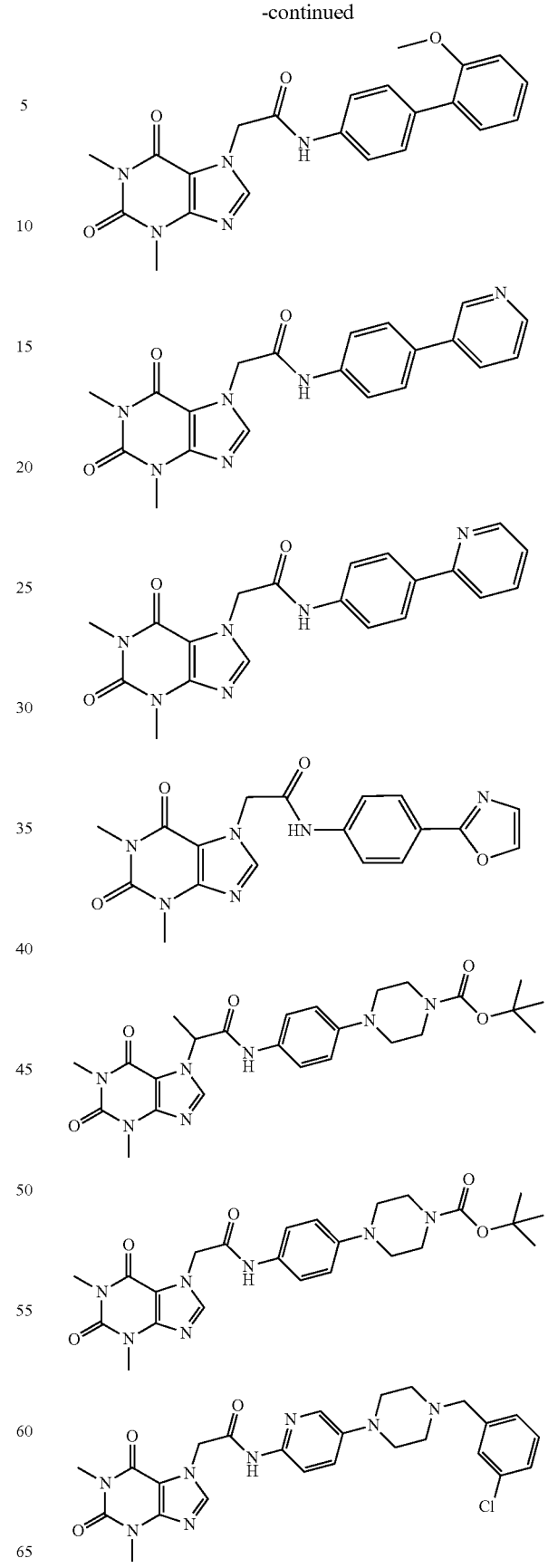

29
-continued
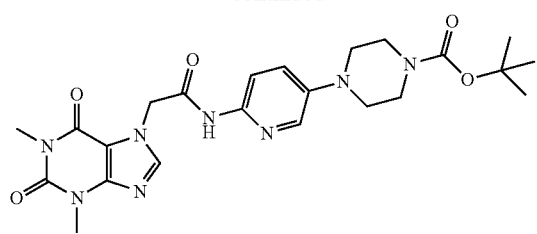
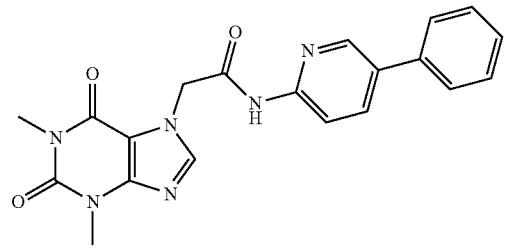
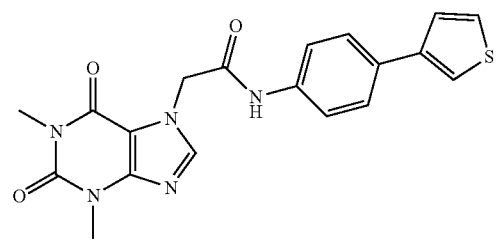
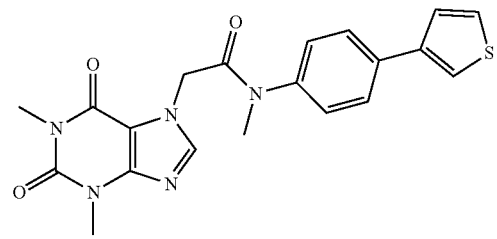
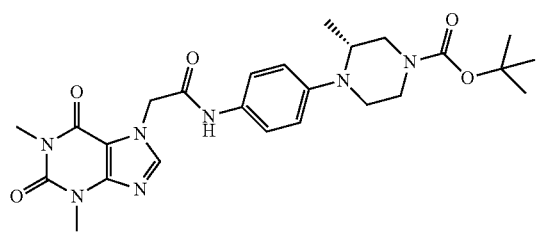
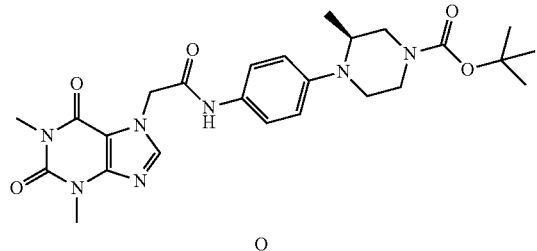
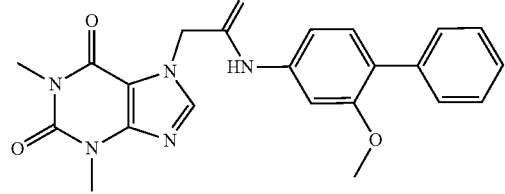
30
-continued
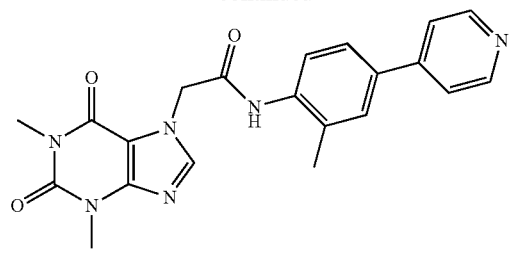
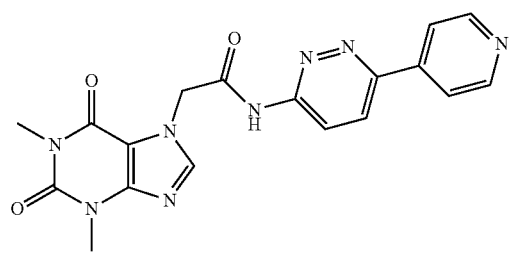
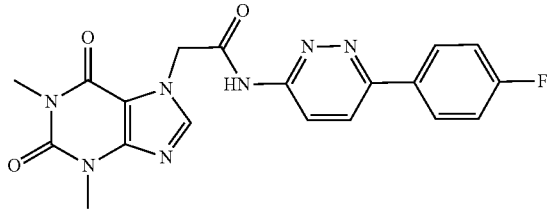
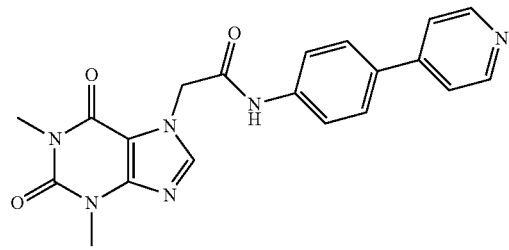
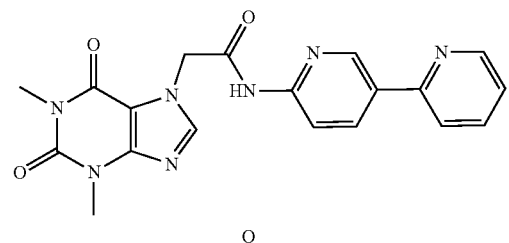
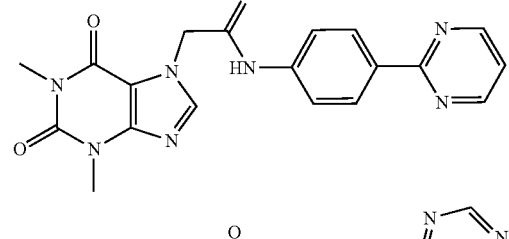
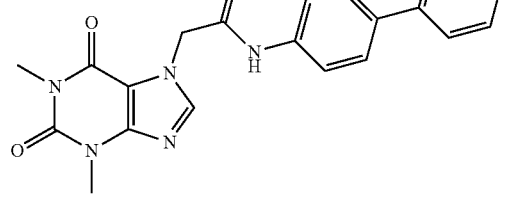

31
-continued
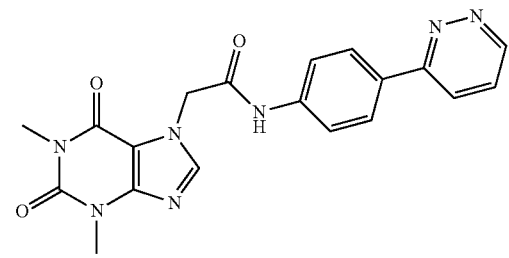
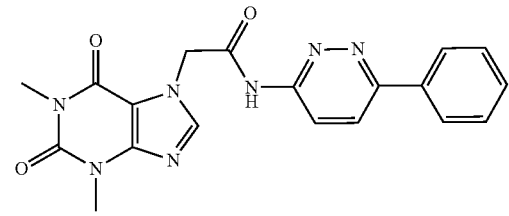
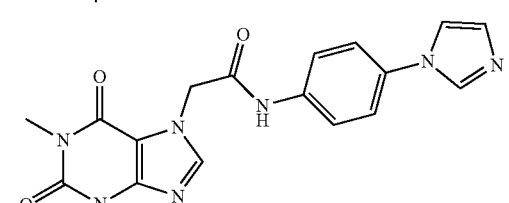
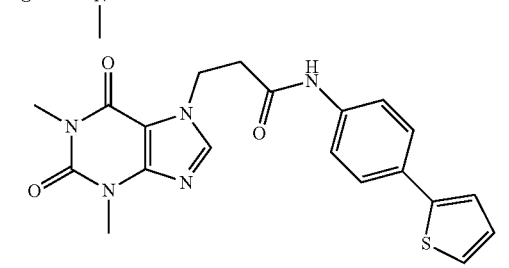
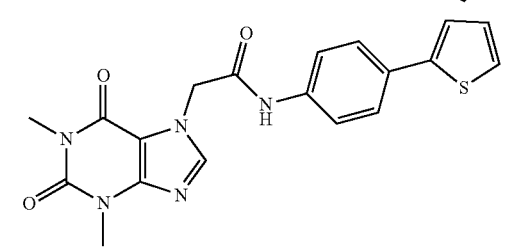
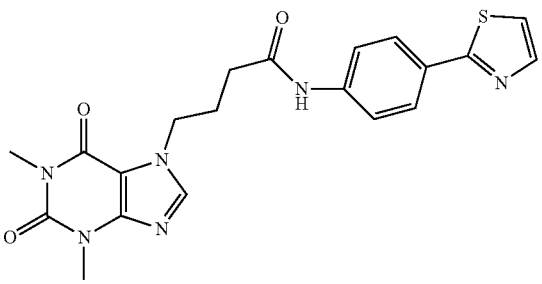
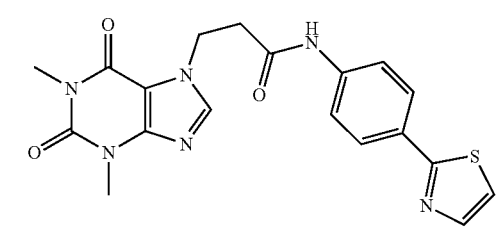
32
-continued
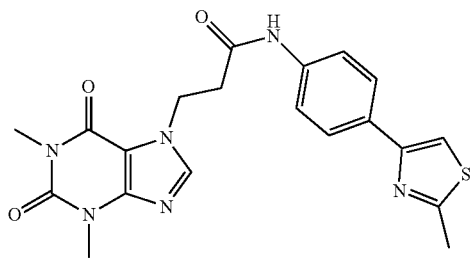
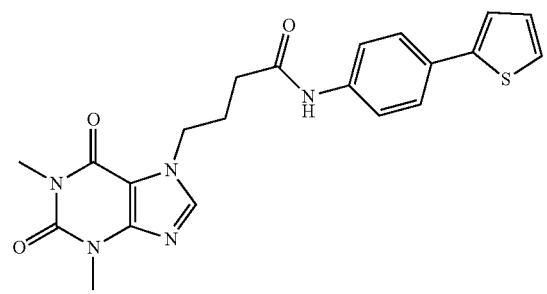
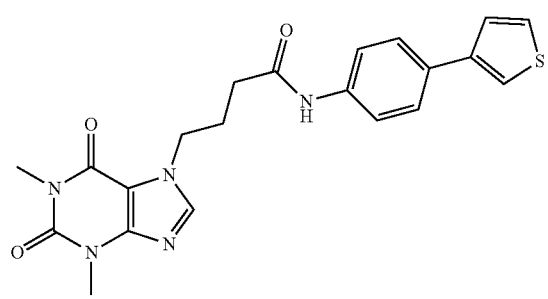
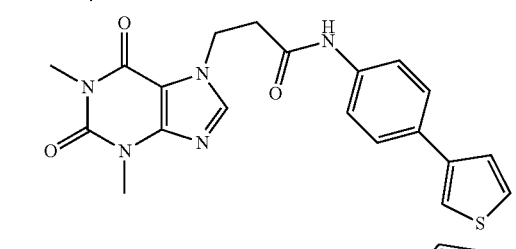
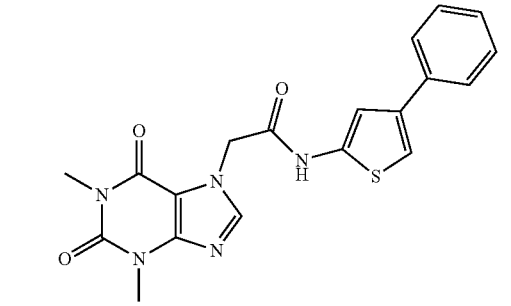
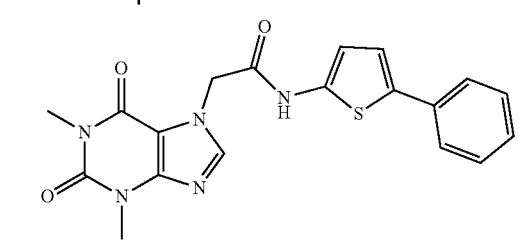

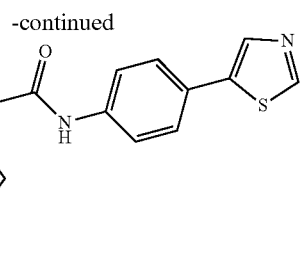

The compounds of the present invention may have an $IC_{50}$ against STF3A of less than about 10 micromolar. The $IC_{50}$ may be less than about 5, 2, 1, 0.5, 0.2 or 0.1 micromolar. It may be between about 0.01 and about 10 micromolar, or between about 0.01 and 5, 0.01 and 1, 0.01 and 0.5, 0.01 and 0.1, 0.01 and 0.05, 0.1 and 5, 0.1 and 1, 0.1 and 0.5, 0.1 and 10, 0.5 and 10, 1 and 10, 5 and 10, 1 and 5 or 0.1 and 0.5, e.g. about 0.01, 0.02, 0.03, 0.04, 0.05, 0.1, 0.2, 0.3, 0.4, 0.5, 0.6, 0.7, 0.8, 0.9, 1, 2, 3, 4, 5, 6, 7, 8, 9 or 10 micromolar. A suitable method for testing $IC_{50}$ is as follows: approximately 5000 cells in 75 μl culture media are seeded in each well of black 96 well plates and incubated overnight at 37° C. 25 μl of serially diluted compound is then added to the cells giving final concentration of. After 1 day of treatment, 100 μl of a luminescent cell viability assay reagent is added to each well and incubated for 10 minutes at room temperature. Luminescence is then measured to determine $IC_{50}$.

The compound may be such that it does not modulate, or does not inhibit, TRPA1. It may not inhibit TRPA1 at an $IC_{50}$ of about 10 micromolar or of about 5 micromolar or of about 2 micromolar or of about 1 micromolar. It may be a TRPA1 non-inhibitor. The term not inhibit" in this context may refer to an inhibition of less than about 10%, or less than about 5, 2 or 1% at the specified concentration.

The compounds of the present invention may inhibit phosphorylation of co-receptor LRP6 in PA-1 teratocarcinoma cells and/or in HPAF-II pancreatic adenocarcinoma cells by greater than about 40% after 4 hours at a concentration of about 2 micromolar. In this context, inhibition of 40% indicates that the concentration of phosphorylated LRP6 after 4 hours is 40% lower than in a control to which no inhibiting compound was added. The inhibition under the specified conditions may be greater than about 40%, or greater than about 45, 50 or 55%, and may be for example about 40, 45, 50, 55 or 60%. The inhibition may be achieved with a concentration of less than about 3 micromolar, or less than about 2, 1, 0.5, 0.2, 0.1 or 0.05 micromolar, or at a concentration of between about 0.003 and 2 micromolar, or between about 0.003 and 1.5 micromolar, 0.003 and 1 micromolar, 0.003 and 0.5 micromolar, 0.003 and 0.2 micromolar, 0.003 and 0.1 micromolar, 0.003 and 0.05, 0.003 and 0.01, 0.01 and 2, 0.1 and 2, 1 and 2, 0.01 and 0.1, 0.01 and 1, 0.01 and 0.1 and 0.05 or 0.005 and 0.5 micromolar, e.g. at a concentration of about 0.003, 0.005, 0.01, 0.002, 0.05, 0.1, 0.2, 0.5, 1, 1.5 or 2 micromolar.

The compounds of the present invention may be made as exemplified in the Examples provided herewith. A common method involves coupling 1,3-dimethyl-3,7-dihydro-1H-purine-2,6-dione (or suitable derivative such as an acid chloride) with an amine $H_2N-Ar-Cy$ (or a protected derivative of that if Ar or Cy have reactive substituents other than $NH_2$). This reaction may be conducted in the presence of a suitable amine, commonly a tertiary amine such as HATU and/or triethylamine.

The present invention encompasses in particular the anhydrous form of the free base of 2-(1,3-dimethyl-2,6-dioxo-1,2,3,6-tetrahydro-7H-purin-7-yl)-N-(6-phenylpyridazin-3-yl)acetamide, pharmaceutical compositions containing the anhydrous form of this free base and methods of use of the anhydrous form of the free base in the treatment of certain medical conditions. This compound is labelled herein as compound 5.

In the development of a drug in solid state form suitable for scale up and cGMP production and ultimately for clinical and commercial use, an acceptable level of drug activity against the target of interest is only one of the important variables that must be considered. For example, in the formulation of pharmaceutical compositions it is imperative that the pharmaceutically active substance be in a form that can be reliably reproduced in a commercial manufacturing process and which is robust enough to withstand the conditions to which the pharmaceutically active substance is exposed.

In a manufacturing sense it is important that during commercial manufacture the manufacturing process of the pharmaceutically active substance be such that the same material is reproduced when the same manufacturing conditions are used. In addition it is desirable that the pharmaceutically active substance exists in a solid form where minor changes to the manufacturing conditions do not lead to major changes in the solid form of the pharmaceutically active substance produced. For example it is important that the manufacturing process produce material having the same crystalline properties on a reliable basis and also produce material having the same level of hydration.

In addition it is important that the pharmaceutically active substance be stable both to degradation, hygroscopicity and subsequent changes to its solid form. This is important to facilitate the incorporation of the pharmaceutically active ingredient into pharmaceutical formulations. If the pharmaceutically active substance is hygroscopic ("sticky") in the sense that it absorbs water (either slowly or over time) it is almost impossible to reliably formulate the pharmaceutically active substance into a drug as the amount of substance to be added to provide the same dosage will vary greatly depending upon the degree of hydration. Furthermore variations in hydration or solid form ("polymorphism") can lead to changes in physico-chemical properties, such as solubility or dissolution rate, which might in turn lead to inconsistent oral absorption in a patient.

Accordingly, chemical stability, solid state stability, and "shelf life" of the pharmaceutically active agent are very important factors. In an ideal situation the pharmaceutically active agent and any compositions containing it, should be capable of being effectively stored over appreciable periods of time, without exhibiting a significant change in the physico-chemical characteristics of the active component such as its activity, moisture content, solubility characteristics, solid form and the like.

In relation to 2-(1,3-dimethyl-2,6-dioxo-1,2,3,6-tetrahydro-7H-purin-7-yl)-N-(6-phenylpyridazin-3-yl)acetamide, initial studies were carried out on the free base, the preferred chemical form, and indicated that polymorphism was prevalent with the compound being found to adopt more than one crystalline form depending upon the manufacturing conditions. In addition it was observed that the moisture content varied from batch to batch.

Accordingly the inventors have prepared a single polymorphic form of 2-(1,3-dimethyl-2,6-dioxo-1,2,3,6-tetrahydro-7I 1-purin-7-yl)-N-(6-phenylpyridazin-3-yl)acetamide which overcomes or ameliorates one or more of the above identified problems.

The present invention therefore encompasses an anhydrous form of the free base (non-hydrated single polymorph) of 2-(1,3-dimethyl-2,6-dioxo-1,2,3,6-tetrahydro-7H-purin-7-yl)-n-(6-phenylpyridazin-3-yl)acetamide.

The anhydrous free base may be crystalline. The crystalline anhydrous free base shows on X-ray diffraction a peak on the 2theta scale at 22.2°±0.5°. It also shows on X-ray diffraction peaks on the 2theta scale at 5.5°±0.5° and 14.2°±0.5°. In particular, it shows on X-ray diffraction at least four peaks on the 2theta scale selected from the group consisting of 5.5°±0.5° and 12.5°±0.5°, 14.2°±0.5°, 16.7°±0.5°, 17.7°±0.5°, 18.8°±0.5°, 22.4°±0.5°, 24.2°±0.5° and 31.7°±0.5°. Specifically it shows on X-ray diffraction peaks on the 2theta scale of and 5.5°±0.5° and 12.5°±0.5°, 14.2°+0.5°, 16.7°±0.5°, 17.7°±0.5°, 18.0°±0.5°, 18.8°±0.5°, 19.6°+0.5°, 20.6°±0.5°, 22.4°±0.5°, 24.2°±0.5°, 24.4°±0.5°, 25.0°±0.5°, 27.0°±0.5°, 27.6°±0.5°, 29.8°±0.5°, 31.7°±0.5° and 32.2°±0.5°.

The present invention also encompasses a pharmaceutical composition comprising the anhydrous free base as described above. It also encompasses a method of treating or preventing a proliferative disorder comprising administration of a therapeutically effective amount of the anhydrous free base of the invention to a patient in need thereof. In some embodiments the proliferative disorder is cancer. It further encompasses the use of the anhydrous free base of the invention in the treatment of a proliferative disorder such as cancer. It further encompasses the use of the anhydrous free base of the invention in the manufacture of a medicament for the treatment of a proliferative disorder. In some embodiments the proliferative disorder is cancer.

Disclosed herein are also compositions for the modulation of Wnt activity, optionally for the treatment of a disease or condition associated with Wnt pathway activity. These incorporate the compound of structure I as defined above, together with one or more pharmaceutically acceptable adjuvants, diluents and/or carriers.

Modulator and inhibitor compounds and agents of the present invention may be administered as compositions either therapeutically or preventively. In a therapeutic application, compositions are administered to a patient already suffering from a disease, in an amount sufficient to cure or at least partially arrest the disease and its complications. The composition should provide a quantity of the compound or agent sufficient to effectively treat the patient.

The therapeutically effective dose level for any particular patient will depend upon a variety of factors including: the disorder being treated and the severity of the disorder; activity of the compound or agent employed; the composition employed; the age, body weight, general health, sex and diet of the patient; the time of administration; the route of administration; the rate of sequestration of the agent or compound; the duration of the treatment; drugs used in combination or coincidental with the treatment, together with other related factors well known in medicine.

One skilled in the art would be able, by routine experimentation, to determine an effective, non-toxic amount of agent or compound which would be required to treat applicable diseases.

Generally, an effective dosage is expected to be in the range of about 0.0001 mg to about 1000 mg per kg body weight per 24 hours; typically, about 0.001 mg to about 750 mg per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours; about 1.0 mg to about 250 mg per kg body weight per 24 hours. More typically, an effective dose range is expected to be in the range about 1.0 mg to about 200 mg per kg body weight per 24 hours; about 1.0 mg to about 100 mg per kg body weight per 24 hours; about 1.0 mg to about 50 mg per kg body weight per 24 hours; about 1.0 mg to about 25 mg per kg body weight per 24 hours; about 5.0 mg to about 50 mg per kg body weight per 24 hours; about 5.0 mg to about 20 mg per kg body weight per 24 hours; about 5.0 mg to about 15 mg per kg body weight per 24 hours.

Alternatively, an effective dosage may be up to about 500 mg/m$^2$. Generally, an effective dosage is expected to be in the range of about 25 to about 500 mg/m$^2$, preferably about 25 to about 350 mg/m$^2$, more preferably about 25 to about 300 mg/m$^2$, still more preferably about 25 to about 250 mg/m$^2$, even more preferably about 50 to about 250 mg/m$^2$, and still even more preferably about 75 to about 150 mg/m$^2$.

Typically, in therapeutic applications, the treatment would commonly be for the duration of the disease state.

Further, it will be apparent to one of ordinary skill in the art that the optimal quantity and spacing of individual dosages will be determined by the nature and extent of the disease state being treated, the form, route and site of administration, and the nature of the particular individual being treated. Also, such optimum conditions can be determined by conventional techniques.

It will also be apparent to one of ordinary skill in the art that the optimal course of treatment, such as, the number of doses of the composition given per day for a defined number of days, can be ascertained by those skilled in the art using conventional course of treatment determination tests.

In general, suitable compositions may be prepared according to methods which are known to those of ordinary skill in the art and accordingly may include a pharmaceutically acceptable carrier, diluent and/or adjuvant.

These compositions can be administered by standard routes. In general, the compositions may be administered by the parenteral (e.g., intravenous, intraspinal, subcutaneous or intramuscular), oral or topical route. More preferably administration is by the parenteral route.

The carriers, diluents and adjuvants must be "acceptable" in terms of being compatible with the other ingredients of the composition, and not deleterious to the recipient thereof.

Examples of pharmaceutically acceptable carriers or diluents are demineralised or distilled water; saline solution; vegetable based oils such as peanut oil, safflower oil, olive oil, cottonseed oil, maize oil, sesame oils, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or isopropanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

The compositions of the invention may be in a form suitable for administration by injection, in the form of a formulation suitable for oral ingestion (such as capsules, tablets, caplets, elixirs, for example), in an aerosol form suitable for administration by inhalation, such as by intranasal inhalation or oral inhalation, in a form suitable for parenteral administration, that is, subcutaneous, intramuscular or intravenous injection.

For administration as an injectable solution or suspension, non-toxic parenterally acceptable diluents or carriers can include, Ringer's solution, isotonic saline, phosphate buffered saline, ethanol and 1,2 propylene glycol.

Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl distearate which delay disintegration.

Adjuvants typically include emollients, emulsifiers, thickening agents, preservatives, bactericides and buffering agents.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

The emulsions for oral administration may further comprise one or more emulsifying agents. Suitable emulsifying agents include dispersing agents as exemplified above or natural gums such as guar gum, gum acacia or gum tragacanth.

Methods for preparing parenterally administrable compositions are apparent to those skilled in the art, and are described in more detail in, for example, Remington's Pharmaceutical Science, 15th ed., Mack Publishing Company, Easton, Pa., hereby incorporated by reference herein.

The composition may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

The compositions may also be administered in the form of liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p. 33 et seq., the contents of which is incorporated herein by reference.

The oral formulation may be formulated with one or more pharmacologically acceptable ingredients to make a tablet or capsule etc. with an enteric coating. Methods for such formulations are well known to those skilled in the art (see e.g., Remington: The Science and Practice of Pharmacy, 19$^{th}$ ed. (1995) Mack Publishing Company, Easton, Pa.; herein incorporated by reference). The enteric coating may be an enteric coating which enhances delivery of the composition or active(s) drugs to specific regions of the gastrointestinal tract for enhanced bioavailability, such as are described in United States of America Patent Application Publication No. 20040162263 entitled "Pharmaceutical formulations targeting specific regions of the gastrointestinal tract" to Sands et al and published 19 Aug. 2004.

EXAMPLES

The following examples provide compounds according to the present invention together with a number of general synthetic schemes for preparing the compounds. Each synthetic scheme has been illustrated with a specific example, and the examples following that may be made by the same general process. The person skilled in the art will readily appreciate the variations required to the illustrated example of each synthetic scheme in order to prepare other related compounds.

Synthesis of Amines

Suzuki Method A: A stirred solution of the arylhalide (1 equiv.), boronic acid (1.5 equiv.) and sodium carbonate (2 equiv.) in toluene (0.08 M) and water (0.32 M) was degassed for 15 min with argon. Tetrakis(triphenylphosphine)palladium(0) (0.05 equiv.) was added to reaction mixture and the reaction mixture was heated to reflux for 16 h. After completion of starting material, the reaction mixture was concentrated and water was added to reaction mixture and extracted with ethyl acetate. The combined organic layers were washed with brine, dried with $Na_2SO_4$ and concentrated under vacuum. The crude compound was purified by column chromatography to afford the purified product.

Synthesis of 6-phenylpyridazin-3-amine

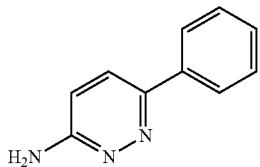 [SMILES: Nc1ccc(-c2ccccc2)nn1]

¹H NMR (400 MHz, DMSO-d₆) δ (ppm): 7.96-7.94 (d, J=8 Hz, 2H), 7.82-7.80 (d, J=9.2 Hz, 1H), 7.48-7.35 (m, 3H), 6.86-6.84 (m, 1H), 6.64 (br s, 2H). LC-MS: m/z 172.0 (M+H) with a purity of 82%.

Synthesis of 4-(pyridazin-3-yl) aniline

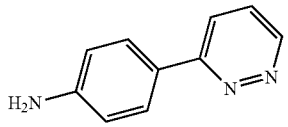 [SMILES: Nc1ccc(-c2cccnn2)cc1]

¹H NMR (400 MHz, CDCl₃) δ (ppm): 9.01-9.0 (d, J=4.4 Hz, 1H), 8.01-7.99 (d, J=8.8 Hz, 1H), 7.88-7.86 (d, J=7.9 Hz, 2H), 7.62-7.60 (m, 1H), 6.68-6.66 (d, J=8.0 Hz, 2H), 5.61 (s, 2H).

Synthesis of 4-(thiazol-5-yl)aniline

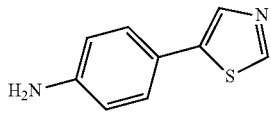 [SMILES: Nc1ccc(-c2cncs2)cc1]

¹H NMR (400 MHz, CDCl₃) δ (ppm): 8.87 (s, 1H), 8.01 (s, 1H), 7.33-7.31 (d, J=8.4 Hz, 2H), 6.60-6.58 (d, J=8.3 Hz, 2H), 5.42 (s, 2H).

Synthesis of 6-(4-fluorophenyl)pyridazin-3-amine

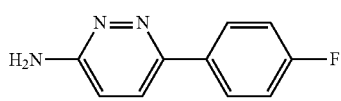 [SMILES: Nc1ccc(-c2ccc(F)cc2)nn1]

¹H-NMR (400 MHz; DMSO-d₆) δ (ppm): 8.02-7.98 (m, 2H), 7.82 (d, J=9.2 Hz, 1H), 7.29 (t, J=9.2 Hz, 2H), 6.84 (d, J=9.6 Hz, 1H), 6.5 (s, 2H). LC-MS: m/z 190 (M+H) with a purity of 99%.

Synthesis of 3'-(trifluoromethoxy)biphenyl-4-amine

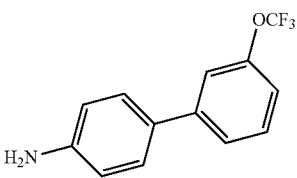 [SMILES: Nc1ccc(-c2cccc(OC(F)(F)F)c2)cc1]

¹H NMR (400 MHz, CDCl₃) δ (ppm): 7.44-7.46 (m, 1H), 7.36-7.41 (m, 4H), 7.09-7.11 (m, 1H), 6.74-6.77 (m, 2H), 3.77 (bs, 2H).

Synthesis of 5-(thiazol-2-yl)pyridin-2-amine

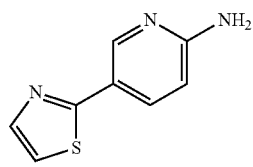 [SMILES: Nc1ccc(-c2nccs2)cn1]

¹H NMR (400 MHz, MeOD-d₄) δ (ppm): 8.48 (s, 1H), 7.95-7.98 (m, 1H), 7.77 (d, J=3.6 Hz, 1H), 7.48 (d, J=3.6 Hz, 1H), 6.64-6.66 (m, 1H). LC-MS: m/z 178 (M+H).

Synthesis of 4'-morpholinobiphenyl-4-amine

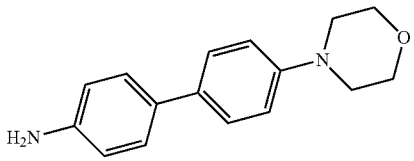 [SMILES: Nc1ccc(-c2ccc(N3CCOCC3)cc2)cc1]

¹H NMR (400 MHz, DMSO-d₆) δ (ppm): 7.39 (d, J=8.80 Hz, 2H), 7.26 (d, J=8.80 Hz, 2H), 6.94 (d, J=8.80 Hz, 2H), 6.60 (d, J=8.80 Hz, 2H), 5.06 (s, 2H), 3.74 (t, J=4.80 Hz, 4H), 3.09 (t, J=4.80 Hz, 4H).

Synthesis of 3¹-morpholinobiphenyl-4-amine

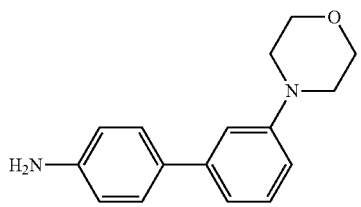 [SMILES: Nc1ccc(-c2cccc(N3CCOCC3)c2)cc1]

¹H NMR (400 MHz, DMSO-d₆) δ (ppm): 7.32-7.34 (m, 2H), 7.19-7.23 (m, 1H), 7.03 (s, 1H), 6.95-6.97 (m, 1H), 6.78-6.81 (m, 1H), 6.60-6.62 (m, 2H), 3.74 (t, J=4.80 Hz, 4H), 3.14 (t, J=4.80 Hz, 4H). LC-MS: m/z 255 (M+H) with a purity of 88%.

Synthesis of 4-(pyrimidin-2-yl) aniline

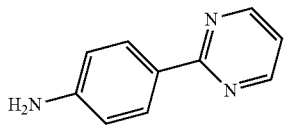 [SMILES: Nc1ccc(-c2ncccn2)cc1]

Synthesis of 4-(2-chloropyrimidin-4-yl)aniline

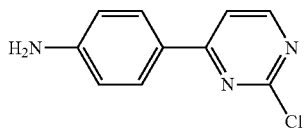 [SMILES: Nc1ccc(-c2ccnc(Cl)n2)cc1]

$^1$H-NMR (400 MHz; DMSO-d$_6$) δ (ppm): 8.54 (d, J=5.2 Hz, 1H), 7.92 (d, J=8.4 Hz, 2H), 7.83 (d, J=5.2 Hz, 1H), 6.65 (d, J=8.8 Hz, 2H), 6.04 (s, 2H). MS (ESI): m/z 206 [M+H]+. LC-MS: Purity of 99%.

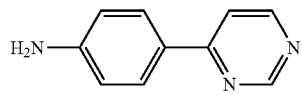

To a stirred solution of 4-(2-chloropyrimidin-4-yl)aniline (1 equiv.) in methanol (0.1 M) and 10% aqueous NaOH (0.24 M) was added 10% Pd/C (20 wt. %) and stirred under Hydrogen balloon pressure at room temperature for 16 h. The reaction mixture was filtered through celite pad and washed with methanol, filtrate concentrated under reduced pressure. The resultant solid was recrystalized with 30% ethyl acetate in petroleum ether to afford 4-(pyrimidin-4-yl) aniline as a pale yellow solid. $^1$H-NMR (400 MHz; DMSO-d$_6$) δ (ppm): 9.02 (s, 1H), 8.62 (d, J=5.2 Hz, 1H), 7.94 (d, J=8.4 Hz, 2H), 7.81 (d, J=5.6 Hz, 1H), 6.65 (d, J=8.8 Hz, 2H), 5.79 (s, 2H). MS (ESI): m/z 172 [M+H]+. LC-MS: Purity of 94%.

Suzuki Method B: A solution of aryl halide (1 equiv.) in 1,4-dioxane (0.12 M) and water (0.5 M) was treated with the respective boronic acid or ester (1.2 equiv.), tricyclohexylphosphine (0.1 equiv.) and K$_3$PO$_4$ (2 equiv.) at room temperature. Nitrogen gas was passed through the reaction mixture for 15 min. Pd$_2$(dba)$_3$ (0.1 equiv.) was added to the reaction mixture and degassed for another 15 min. The reaction mixture heated to 100° C. for 16 h. After completion, reaction mixture was cooled to room temperature, added water, extracted with ethyl acetate thrice. The combined organic layers were washed with brine solution, dried over anhydrous Na$_2$SO$_4$, filtered, rotary evaporated and dried under vacuum to afford crude product. The crude product was purified by column chromatography to afford the purified product.

Synthesis of 2,3'-bipyridin-6'-amine

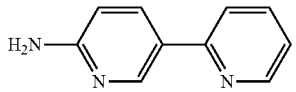

MS (ESI): m/z 172.13 [M+H]+.

Synthesis of 4-(thiazol-2-yl) aniline

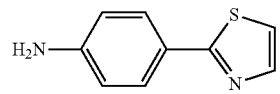

$^1$H-NMR (400 MHz; CDCl$_3$) δ (ppm): 7.77 (d, J=6.0 Hz, 1H), 7.19 (d, J=3.6 Hz, 1H), 6.71 (d, J=4.8 Hz, 2H), 3.8 (brs, 2H). LC-MS: m/z 175 [M–H]–. Purity of 62%.

Suzuki Method C: A stirred solution of arylhalide (1.1 equiv.) in 1,4-dioxane (0.7 M) and water (3.5 M) was treated with the respective boronic acid or ester (1 equiv.) and K$_2$CO$_3$ (2.4 equiv.) at room temperature. Nitrogen gas was passed through the reaction mixture for 15 min. Pd(dppf) Cl$_2$.DCM (0.02 equiv.) was added to the reaction mixture and degassed for another 15 minutes. The reaction mixture heated to 100° C. for 4 h. After completion, reaction mixture was cooled to room temperature, added water, extracted with ethyl acetate trice. The combined organic layers was washed with brine solution, dried over anhydrous Na$_2$SO$_4$, filtered, rotary evaporated and dried under vacuum to afford crude product. The crude product was purified by column chromatography to afford the purified product.

Synthesis of 4-(thiophen-3-yl) aniline

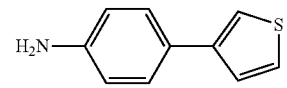 [SMILES: Nc1ccc(-c2ccsc2)cc1]

$^1$H-NMR (400 MHz; CDCl$_3$) δ (ppm): 7.41 (d, J=8.4 Hz, 2H), 7.33 (d, J=3.1 Hz, 1H), 7.32 (d, J=0.9 Hz, 1H), 7.31 (s, 1H), 6.71 (d, J=8.4 Hz, 2H), 3.7 (brs, 2H). MS (ESI): m/z 176 [M+H]+. LC-MS: Purity of 97%.

Synthesis of 6-(pyridin-4-yl) pyridazin-3-amine

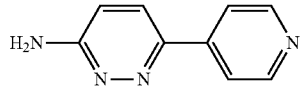 [SMILES: Nc1ccc(-c2ccncc2)nn1]

$^1$H NMR (400 MHz, DMSO-d$_6$) δ (ppm): 7.96-7.94 (d, J=8 Hz, 2H), 7.82-7.80 (d, J=9.2 Hz, 1H), 7.48-7.35 (m, 3H), 6.86-6.84 (m, 1H), 6.64 (br s, 2H). LC-MS: m/z 172.0 (M+H) with a purity of 82%.

Synthesis of
5-(2-methylthiazol-4-yl)pyridin-2-amine

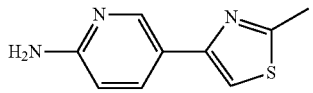

¹H NMR (400 MHz, DMSO-do) δ (ppm): 8.58-8.57 (1H, d, J=1.6 Hz), 7.94-7.92 (1H, dd, J1=2 Hz, J2=6.4 Hz), 7.15 (1H, s), 6.56-6.54 (1H, d, J=8.4 Hz), 4.54 (2H, brs), 2.76 (3H, s).

Synthesis of N-methyl-4-(thiophen-3-yl)aniline

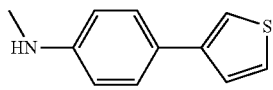

¹H NMR (400 MHz, CDCl₃) δ (ppm): 7.45-7.43 (d, J=7.0 Hz, 2H), 7.33 (s, 1H), 7.32-7.27 (m, 3H), 6.65-6.63 (d, J=7.1 Hz, 1H), 3.77-3.58 (brs, 1H), 2.87 (s, 1H).

Synthesis of 4-(oxazol-2-yl) aniline

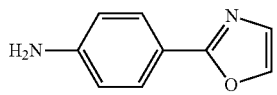

To a solution of commercially available 2-(4-nitrophenyl) oxazole, 1 (1 equiv.) in methanol (0.05 M) was added Pd/C (10% by wt) and stirred reaction at room temperature under H₂ gas balloon pressure for 4 h. After completion of starting material, the reaction mixture was filtered through Celite bed and filtrate was concentrated to give 4-(oxazol-2-yl) aniline, 2 as a brown solid. ¹H NMR (400 MHz, DMSO-d₆) δ (ppm): 8.0 (s, 1H), 7.64 (d, J=8.4 Hz, 2H), 7.20 (s, 1H), 6.63-6.61 (d, J=8.4 Hz, 2H), 5.68 (brs, 2H). LC-MS: m/z 161.0 (M+H) with a purity of 97%.

Synthesis of 5-phenylthiophen-2-amine

Step 1: Preparation of ethyl
2-amino-5-phenylthiophene-3-carboxylate

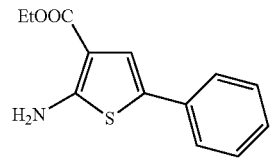 [SMILES: CCOC(=O)c1cc(-c2ccccc2)sc1N]

A stirred solution of the respective aldehyde or ketone (1 equiv.), ethyl cyano acetate (1 equiv.) and S powder in ethanol (1.6 M) was treated with morpholine (5 M) dropwise at room temperature and stirred for 3 h. After completion of starting material, the reaction mixture was concentrated and crude compound was purified by column chromatography to give the product. ¹H NMR (400 MHz, CDCl₃) δ (ppm): 7.45-7.43 (m, 2H), 7.34-7.30 (m, 2H), 7.27-7.20 (m, 2H), 6.0 (brs, 2H), 4.33-4.27 (q, J=7.2 Hz, 2H), 1.39-1.35 (t, J=7.2 Hz, 3H). LC-MS: m/z 248.2 (M+H) with a purity of 94%.

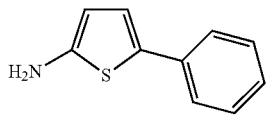

Step 2: Preparation of 5-phenylthiophen-2-amine

A solution of ethyl 2-amino-5-phenylthiophene-3-carboxylate (1 equiv.) in ethanol (0.04 M) was added 50% aq. HCl (0.04 M) and reaction mixture was heated to reflux for 4 h. After completion of starting material, the reaction mixture was cooled to room temperature and concentrated under vacuum and basified with aq.NaHCO₃ solution and extracted with ethyl acetate twice. The combined organic layers were washed with brine solution dried over NaSO₄ concentrated under vacuum. The crude compound was purified by column chromatography to give the purified product. LC-MS: m/z 176.8 (M+H) with a purity of 61%.

Synthesis of 4-phenylthiophen-2-amine

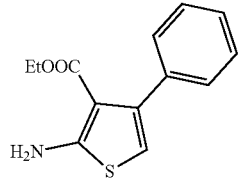 [SMILES: CCOC(=O)c1c(-c2ccccc2)csc1N]

Step 1: Preparation of ethyl
2-amino-4-phenylthiophene-3-carboxylate

¹H NMR (400 MHz, CDCl₃) δ (ppm): 7.30-7.28 (m, 5H), 6.07 (brs, 1H), 6.05 (brs, 2H), 4.06-4.00 (q, J=6.8 Hz, 2H), 0.94-0.91 (t, J=6.8 Hz, 3H). LC-MS: m/z 248.03 (M+H) with a purity of 98%.

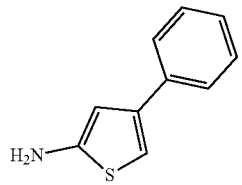 [SMILES: Nc1cc(-c2ccccc2)cs1]

Step 2: Preparation of 4-phenylthiophen-2-amine

¹H NMR (400 MHz, DMSO-d₆) δ (ppm): 7.60-7.58 (m, 2H), 7.40-7.38 (m, 3H), 7.29-7.27 (m, 2H), 7.15-7.11 (m, 2H). LC-MS: m/z 176.0 (M+H) with a purity of 94%.

Synthesis of 4-(pyrrolidin-1-yl)aniline

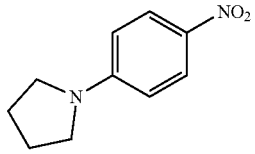 [SMILES: O=[N+]([O-])c1ccc(N2CCCC2)cc1]

Step 1: Preparation of 1-(4-nitrophenyl)pyrrolidine

Potassium carbonate (2 equiv.) and the respective amine (1.1 equiv.) were added to a stirred solution of 1-fluoro-4-nitrobenzene, 1 (1 equiv.) in anhydrous DMSO (0.5 M) and stirred at 120° C. for 18 h. Upon consumption of starting material, the reaction was diluted with water and extracted with dichloromethane. The combined organic layers were washed with brine, dried over $Na_2SO_4$ and concentrated under vacuum. Crude product was purified using column chromatography to afford the purified product. $^1$H NMR (400 MHz, DMSO-$d_6$) δ (ppm): 8.05 (d, J=9.2 Hz, 2H), 6.62 (d, J=9.2 Hz, 2H), 3.38 (m, 4H), 1.99 (m, 4H). LC-MS: m/z 193 (M+H)

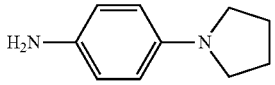

Step 2: Preparation of 4-(pyrrolidin-1-yl)aniline 1-(4-nitrophenyl)pyrrolidine was dissolved in ethyl acetate (0.05 M) and reduced with H-cube at 50° C., 10 bar. Reduction was completed in 2 cycles. The solvent was evaporated off in vacuo, and the crude purified using column chromatography to afford the product. $^1$H NMR (400 MHz, DMSO-$d_6$) δ (ppm): 6.49 (d, J=8.4 Hz, 2H), 6.34 (d, J=8.4 Hz), 4.24 (s, 2H), 3.07 (m, 4H), 1.87 (m, 4H). LC-MS: m/z 163 (M+H).

Synthesis of (S)-tert-butyl 4-(4-aminophenyl)-3-methylpiperazine-1-carboxylate

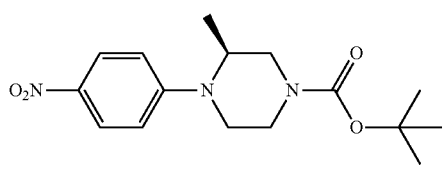 [SMILES: C[C@H]1CN(C(=O)OC(C)(C)C)CCN1c1ccc([N+](=O)[O-])cc1]

Step 1: Preparation of (S)-tert-butyl 3-methyl-4-(4-nitrophenyl)piperazine-1-carboxylate $^1$H NMR (400 MHz, CDCl$_3$) δ (ppm): 8.15-8.12 (m, 2H), 6.79-6.77 (d, J=9.6 Hz, 2H), 4.13-3.96 (m, 3H), 3.57-3.53 (m, 1H), 3.29-3.22 (m, 2H), 3.12 (br s, 1H), 1.49 (s, 9H), 1.18 (d, J=6.4 Hz, 3H). LC-MS: m/z 363 (M+H+41).

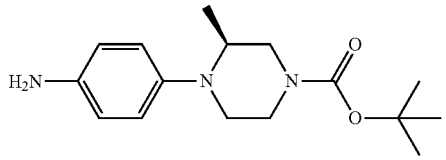

Step 2: Preparation of (S)-tert-butyl 4-(4-aminophenyl)-3-methylpiperazine-1-carboxylate $^1$H NMR (400 MHz, CDCl$_3$) δ (ppm): 6.84 (d, J=8.6 Hz, 2H), 6.64 (d, J=8.6 Hz, 2H), 3.53 (br s, 3H), 3.26 (br s, 2H), 2.99-2.96 (m, 1H), 2.88-2.85 (m, 1H), 1.48 (s, 9H), 0.87 (d, J=6.4 Hz, 3H). LC-MS: m/z 292 (M+H).

Synthesis of (R)-tert-butyl 4-(4-aminophenyl)-3-methylpiperazine-1-carboxylate

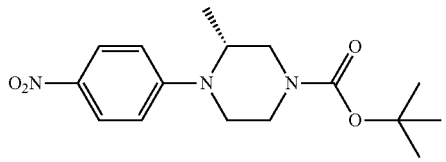

Step 1: Preparation of (R)-tert-butyl 3-methyl-4-(4-nitrophenyl)piperazine-1-carboxylate $^1$H NMR (400 MHz, CDCl$_3$) δ (ppm): 8.15-8.13 (m, 2H), 6.79-6.77 (m, 2H), 4.12 (br s, 2H), 4.02 (br s, 1H), 3.57-3.53 (m, 1H), 3.29-3.22 (m, 2H), 3.12 (br s, 1H), 1.49 (s, 9H), 1.18 (d, J=6.8 Hz, 3H). LC-MS: m/z 363 (M+H+41).

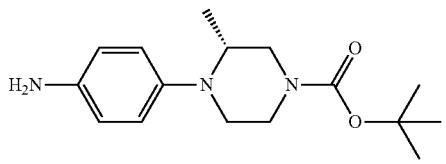 [SMILES: C[C@@H]1CN(C(=O)OC(C)(C)C)CCN1c1ccc([N+](=O)[O-])cc1]

Step 2: Preparation of (R)-tert-butyl 4-(4-aminophenyl)-3-methylpiperazine-1-carboxylate $^1$H NMR (400 MHz, CDCl$_3$) δ (ppm): 6.84 (d, J=8.4 Hz, 2H), 6.65-6.63 (m, 2H), 3.53 (br s, 3H), 3.26 (br s, 2H), 2.99-2.96 (m, 1H), 2.88-2.85 (m, 1H), 1.48 (s, 9H), 0.87 (d, J=6 Hz, 3H). LC-MS: m/z 292 (M+H).

Amide coupling Method A: To a stirred solution of commercially available 2-(1,3-dimethyl-2,6-dioxo-2,3-dihydro-1H-purin-7(6H)-yl)acetic acid, 1 (1 equiv.) in dichloromethane (0.01 M) was added HATU (1.3 equiv.), triethylamine (1.5 equiv.) and the respective amine (1 equiv.). The reaction mixture was allowed to stir at room temperature. Upon completion of the reaction, water was added to the mixture and the mixture was extracted with dichloromethane. The organic layer was washed with brine solution, dried over anhydrous $Na_2SO_4$, and concentrated under vacuum to afford the crude product. The crude product is further purified by column chromatography.

Compound 1: 2-(1,3-dimethyl-2,6-dioxo-2,3-dihydro-1H-purin-7(6H)-yl)-N-(4-(thiazol-5-yl)phenyl)acetamide

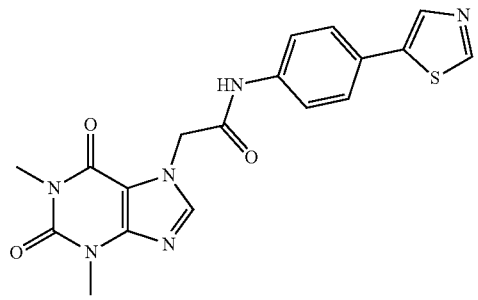 [SMILES: Cn1c(=O)c2c(ncn2CC(=O)Nc2ccc(-c3cncs3)cc2)n(C)c1=O]

¹H NMR (400 MHz, DMSO-d₆) δ (ppm): 10.58 (s, 1H), 9.03 (s, 1H), 8.24 (s, 1H), 8.08 (s, 1H), 7.65 (s, 4H), 5.20 (s, 2H), 3.40 (s, 3H), 3.20 (s, 3H).

Compound 2: 2-(1,3-dimethyl-2,6-dioxo-2,3-dihydro-1H-purin-7(6H)-yl)-N-(5-phenyl thiophen-2-yl)acetamide

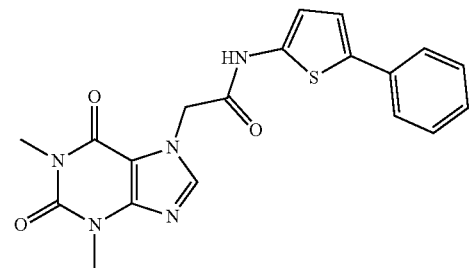 [SMILES: Cn1c(=O)c2c(ncn2CC(=O)Nc2ccc(-c3ccccc3)s2)n(C)c1=O]

¹H NMR (400 MHz, DMSO-d₆) δ (ppm): 11.71 (s, 1H), 8.09 (s, 1H), 7.55-7.53 (d, J=8 Hz, 2H), 7.38-7.34 (t, J=7.6 Hz, 2H), 7.28-7.21 (m, 2H), 6.73-6.72 (d, J=3.6 Hz, 1H), 5.25 (s, 2H), 3.46 (s, 3H), 3.20 (s, 3H). LC-MS: m/z 396.03 (M+H) with a purity of 99.02%. HPLC: At 254 nm with a purity of 95%.

Compound 3: 2-(1,3-dimethyl-2,6-dioxo-2,3-dihydro-1H-purin-7(6H)-yl)-N-(4-phenyl thiophen-2-yl)acetamide

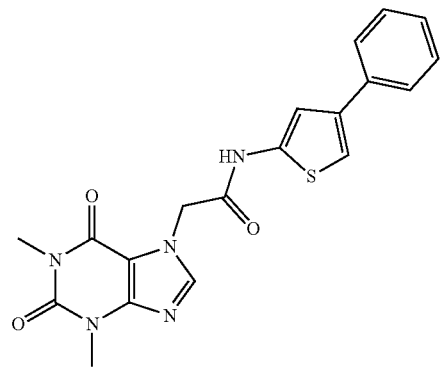 [SMILES: Cn1c(=O)c2c(ncn2CC(=O)Nc2cc(-c3ccccc3)cs2)n(C)c1=O]

¹H NMR (400 MHz, DMSO-d₆) δ (ppm): 11.70 (s, 1H), 8.09 (s, 1H), 7.64-7.62 (d, J=7.6 Hz, 2H), 7.42-7.38 (t, J=7.2 Hz, 2H), 7.31-7.28 (m, 2H), 7.08-7.07 (d, J=1.6 Hz, 1H), 5.26 (s, 2H), 3.46 (s, 3H), 3.20 (s, 3H). LC-MS: m/z 396.11 (M+H) with a purity of 99%.

Compound 4: N-(4-(1H-imidazol-1-yl)phenyl)-2-(1,3-dimethyl-2,6-dioxo-2,3-dihydro-1H-purin-7(6H)-yl)acetamide

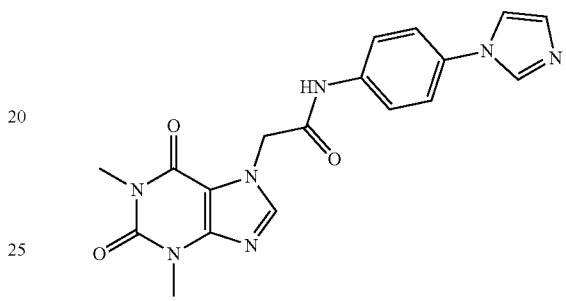

¹H NMR (400 MHz, DMSO-d₆) δ (ppm): 10.57 (s, 1H), 8.18 (s, 1H), 8.08 (s, 1H), 7.68-7.70 (m, 3H), 7.59-7.61 (m, 2H), 7.08 (s, 1H), 5.22 (s, 2H), 3.46 (s, 3H), 3.20 (s, 3H). LC-MS: m/z 380 (M+H) with a purity of 99%.

Compound 5: 2-(1,3-dimethyl-2,6-dioxo-1,2,3,6-tetrahydro-7H-purin-7-yl)-N-(6-phenylpyridazin-3-yl)acetamide (alternatively named 2-(1,3-dimethyl-2,6-dioxo-2,3-dihydro-1H-purin-7(6H)-yl)-N-(6-phenyl pyridazin-3-yl)acetamide)

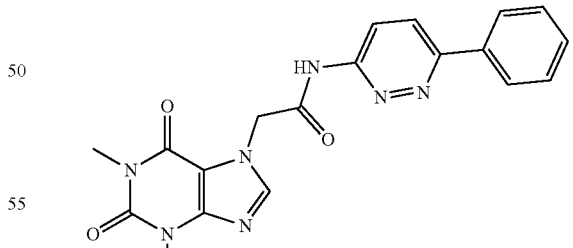

¹H NMR (400 MHz, DMSO-d₆) δ (ppm): 11.77 (s, 1H), 8.32-8.25 (m, 2H), 8.12-8.10 (m, 3H), 7.57-7.49 (m, 3H), 5.37 (s, 2H), 3.46 (s, 3H), 3.19 (s, 3H). LC-MS: m/z 390.1 (M+H) with a purity of 99%.

Compound 6: 2-(1,3-dimethyl-2,6-dioxo-2,3-dihydro-1H-purin-7(6H)-yl)-N-(4-(pyridazin-3-yl)phenyl)acetamide

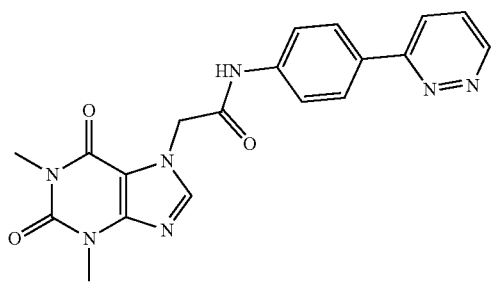 [SMILES: Cn1c(=O)c2c(ncn2CC(=O)Nc2ccc(-c3cccnn3)cc2)n(C)c1=O]

¹H NMR (400 MHz, DMSO-d$_6$) δ (ppm): 10.66 (s, 1H), 9.17-9.16 (d, J=4.4, 1H), 8.20-8.14 (m, 3H), 8.09 (s, 1H), 7.77-7.73 (m, 3H), 5.25 (s, 2H), 3.47 (s, 3H), 3.27 (s, 3H), 3.20 (s, 3H). LC-MS: m/z at 392 [M+H] with 99%.

Compound 7: 2-(1,3-dimethyl-2,6-dioxo-2,3-dihydro-1H-purin-7(6H)-yl)-N-(4-(pyridazin-3-yl)phenyl)acetamide

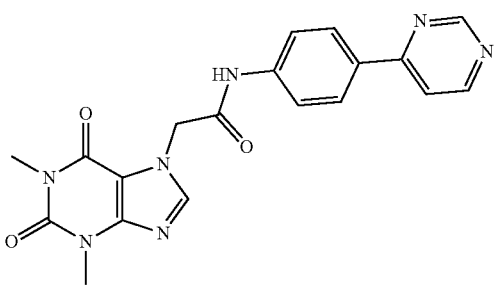 [SMILES: Cn1c(=O)c2c(ncn2CC(=O)Nc2ccc(-c3ccncn3)cc2)n(C)c1=O]

¹H-NMR (400 MHz; DMSO-d$_6$) δ (ppm): 10.65 (brs, 1H), 9.18 (s, 1H), 8.80 (d, J=5.2 Hz, 1H), 8.20 (d, J=8.8 Hz, 2H), 8.07 (s, 1H), 8.02 (d, J=5.2 Hz, 1H), 7.75 (d, J=8.8 Hz, 2H), 5.25 (s, 2H), 3.46 (s, 3H), 3.20 (s, 3H). MS (ESI): m/z 392 [M+H]+. LC-MS: Purity of 97%.

Compound 8: 2-(1, 3-dimethyl-2,6-dioxo-2,3-dihydro-1H-purin-7(6H)-yl)-N-(4-(pyrimidin-2-yl)phenyl)acetamide

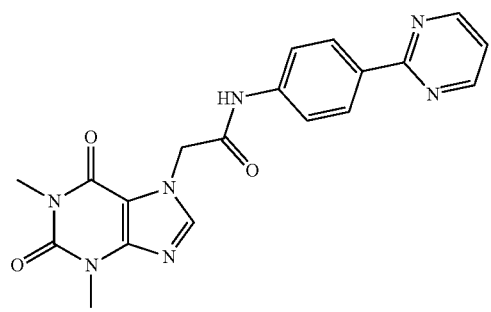 [SMILES: Cn1c(=O)c2c(ncn2CC(=O)Nc2ccc(-c3ncccn3)cc2)n(C)c1=O]

¹H NMR (400 MHz, DMSO-d$_6$) δ (ppm): 10.66 (s, 1H), 8.87-8.86 (d, J=4.0 Hz, 2H), 8.37-8.35 (d, J=8.4 Hz, 2H), 8.08 (s, 1H), 7.74-7.72 (d, J=8.8 Hz, 2H), 7.40-7.38 (t, J=4.8 Hz, 1H), 5.24 (s, 2H), 3.46 (s, 3H), 3.20 (s, 3H). LC-MS: m/z at 392 [M+H] with 99%.

Compound 9: N-(2,3'-bipyridin-6'-yl)-2-(1,3-dimethyl-2,6-dioxo-2,3-dihydro-1H-purin-7(6H)-yl)acetamide

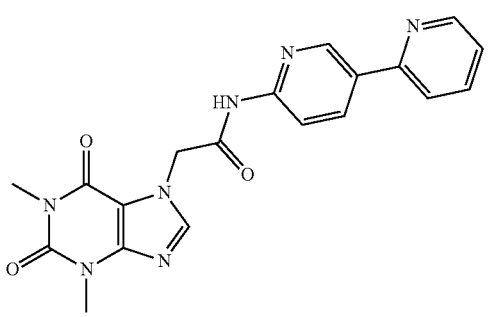 [SMILES: Cn1c(=O)c2c(ncn2CC(=O)Nc2ccc(-c3ccccn3)cn2)n(C)c1=O]

¹H-NMR (400 MHz; DMSO-d$_6$) δ (ppm): 11.21 (s, 1H), 9.08 (s, 1H), 8.67 (d, J=3.4 Hz, 1H), 8.47 (d, J=7.2 Hz, 1H), 8.08 (s, 1H), 8.03 (d, J=7.2 Hz, 2H), 7.9 (t, J=7.6 Hz, 1H), 7.38 (t, J=5.2 Hz, 1H), 5.30 (s, 2H), 3.46 (s, 3H), 3.19 (s, 3H). MS (ESI): m/z 392.13 [M+H]+. LC-MS: Purity of 97%.

Compound 10: 2-(1,3-dimethyl-2,6-dioxo-2,3-dihydro-1H-purin-7(6H)-yl)-N-(4-(pyridin-4-yl)phenyl)acetamide

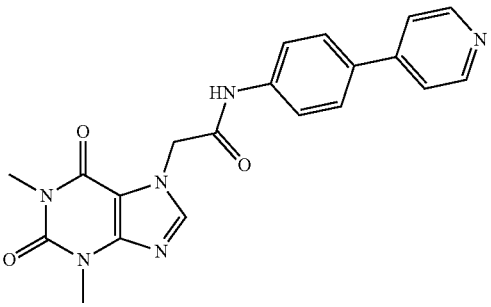 [SMILES: Cn1c(=O)c2c(ncn2CC(=O)Nc2ccc(-c3ccncc3)cc2)n(C)c1=O]

¹H NMR (400 MHz, MeOD-d$_4$) δ (ppm): 8.55 (d, J=6.00 Hz, 2H), 7.992 (s, 1H), 7.73-7.78 (m, 4H), 7.71 (d, J=6.00 Hz, 2H), 5.28 (s, 2H), 3.58 (s, 3H), 3.33 (s, 3H). LC-MS: m/z 391 (M+H) with a purity of 99%.

Compound 11: 2-(1,3-dimethyl-2,6-dioxo-2,3-di-hydro-1H-purin-7(6H)-yl)-N-(6-(4-fluoro phenyl) pyridazin-3-yl)acetamide

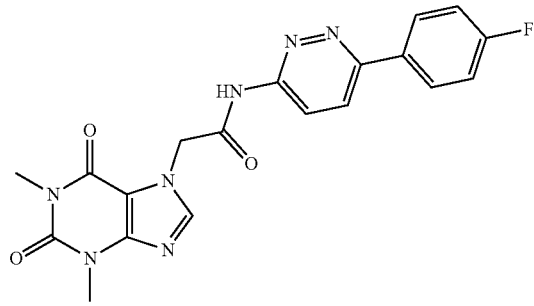 [SMILES: Cn1c(=O)c2c(ncn2CC(=O)Nc2ccc(-c3ccc(F)cc3)nn2)n(C)c1=O]

$^1$H-NMR (400 MHz; CDCl$_3$) δ (ppm): 11.65 (s, 1H), 8.58 (d, J=9.6 Hz, 1H), 7.99 (dd, J=5.2 Hz, J=3.6 Hz, 2H), 7.90 (d, J=9.2 Hz, 1H), 7.73 (s, 1H), 7.17 (t, J=8.8 Hz, 1H), 5.57 (s, 2H), 3.64 (s, 3H), 3.42 (s, 3H). MS (ESI): m/z 410.17 [M+H]+. LC-MS: Purity of 99%.

Compound 12: 2-(1,3-dimethyl-2,6-dioxo-2,3-di-hydro-1H-purin-7(6H)-yl)-N-(6-(pyridin-4-yl) pyridazin-3-yl)acetamide

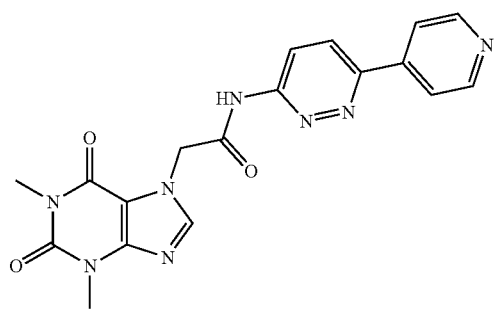 [SMILES: Cn1c(=O)c2c(ncn2CC(=O)Nc2ccc(-c3ccncc3)nn2)n(C)c1=O]

$^1$H NMR (400 MHz, DMSO-d$_6$) δ (ppm): 11.88 (brs, 1H), 8.76 (s, 2H), 8.39-8.37 (m, 2H), 8.15-8.09 (m, 3H), 5.38 (s, 2H), 3.46 (s, 3H), 3.19 (s, 3H). LC-MS: m/z 393.20 (M+H) with a purity of 98.93%. HPLC: At 254 nm with a purity of 98%.

Compound 13: 2-(1,3-dimethyl-2,6-dioxo-2,3-di-hydro-1H-purin-7(6H)-yl)-N-(3-methyl biphenyl-4-yl)acetamide

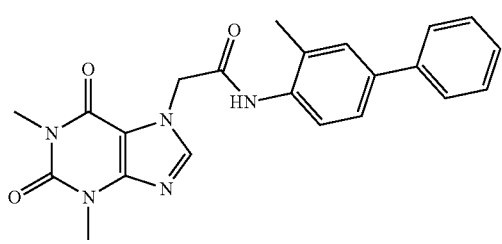 [SMILES: Cc1cc(-c2ccccc2)ccc1NC(=O)Cn1cnc2c1c(=O)n(C)c(=O)n2C]

$^1$H NMR (400 MHz, DMSO-d$_6$) δ (ppm): 9.79 (s, 1H), 8.10 (s, 1H), 7.63 (d, J=7.6 Hz, 2H), 7.54-7.40 (m, 5H), 7.34 (t, J=7.2 Hz, 1H), 5.26 (s, 2H), 3.45 (s, 3H). 3.22 (s, 3H), 2.32 (s, 3H).

Compound 14: 2-(1, 3-dimethyl-2,6-dioxo-2,3-di-hydro-1H-purin-7(6H)-yl)-N-(2-methoxy biphenyl-4-yl)acetamide

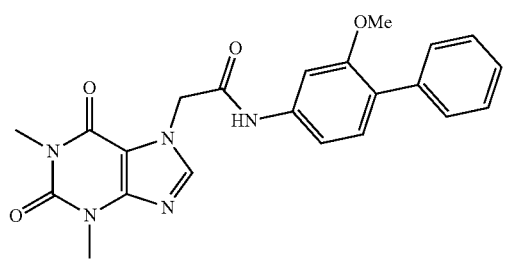 [SMILES: COc1cc(NC(=O)Cn2cnc3c2c(=O)n(C)c(=O)n3C)ccc1-c1ccccc1]

$^1$H NMR (400 MHz, DMSO-d$_6$) δ (ppm): 10.56 (s, 1H), 8.09 (s, 1H), 7.48-7.30 (m, 5H), 7.28-7.17 (m, 3H), 5.23 (s, 2H), 3.72 (s, 3H). 3.46 (s, 3H), 3.20 (s, 3H).

Compound 15: (S)-tert-butyl 4-(4-(2-(1,3-dimethyl-2,6-dioxo-2,3-dihydro-1H-purin-7(6H)-yl)acet-amido)phenyl)-3-methylpiperazine-1-carboxylate

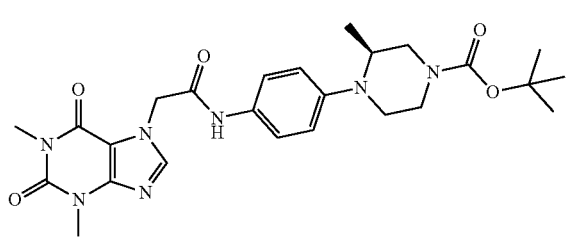 [SMILES: C[C@H]1CN(C(=O)OC(C)(C)C)CCN1c1ccc(NC(=O)Cn2cnc3c2c(=O)n(C)c(=O)n3C)cc1]

$^1$H NMR (400 MHz, CDCl$_3$) δ (ppm): 9.27 (s, 1H), 7.77 (s, 1H), 7.42 (d, J=8.8 Hz, 2H), 6.85 (d, J=8.8 Hz, 2H), 4.94 (s, 2H), 4.00-3.78 (br s, 1H), 3.71-3.69 (m, 2H), 3.61 (s, 3H), 3.46 (s, 3H), 3.42-3.36 (m, 1H), 3.21 (br s, 1H), 3.05-3.03 (m, 2H), 1.47 (s, 9H), 0.94 (d, J=6.4 Hz, 3H). LC-MS: m/z 512 (M+H) with a purity of 97%.

Compound 16: (R)-tert-butyl 4-(4-(2-(1,3-dimethyl-2,6-dioxo-2,3-dihydro-1H-purin-7(6H)-yl)acet-amido)phenyl)-3-methylpiperazine-1-carboxylate

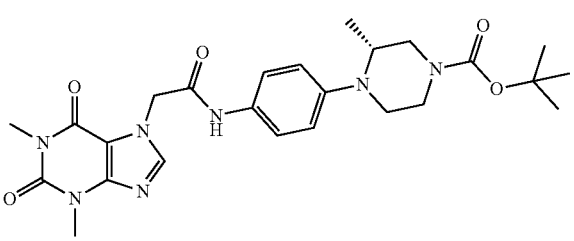 [SMILES: C[C@@H]1CN(C(=O)OC(C)(C)C)CCN1c1ccc(NC(=O)Cn2cnc3c2c(=O)n(C)c(=O)n3C)cc1]

$^1$H NMR (400 MHz, CDCl$_3$) δ (ppm): 9.35 (br s, 1H), 7.77 (s, 1H), 7.46-7.44 (m, 2H), 6.90 (br s, 2H), 4.94 (s, 2H), 3.89 (br s, 1H), 3.70-3.68 (m, 1H), 3.67-3.61 (m, 4H), 3.46

(m, 4H), 3.32-3.25 (br s, 1H), 3.09 (br s, 2H), 1.48 (s, 9H), 0.96 (d, J=6.4 Hz, 3H). LC-MS: m/z 512 (M+H) with a purity of 97%.

Compound 17: 2-(1,3-dimethyl-2,6-dioxo-2,3-di-hydro-1H-purin-7(6H)-yl)-N-methyl-N-(4-(thio-phen-3-yl)phenyl)acetamide

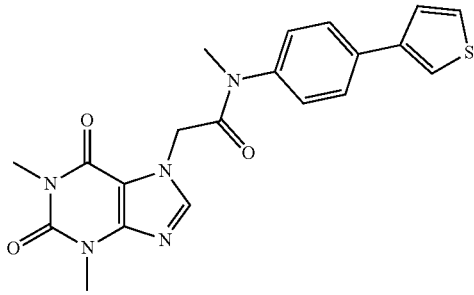 [SMILES: CN(C(=O)Cn1cnc2c1c(=O)n(C)c(=O)n2C)c1ccc(-c2ccsc2)cc1]

$^1$H NMR (400 MHz, CDCl$_3$) δ (ppm): 7.74-7.72 (d, J=7.6 Hz, 2H), 7.54-7.51 (d, J=9.2 Hz, 2H), 7.43-7.26 (m, 4H), 4.89 (s, 2H), 3.59 (s, 3H), 3.38 (s, 3H), 3.34 (s, 3H). MS (ESI) m/z 410 [M+1].

Amide coupling Method B: To a stirred solution of commercially available 2-(1,3-dimethyl-2,6-dioxo-2,3-dihydro-1H-purin-7(6H)-yl)acetic acid, 1 in N,N-dimethylformamide (0.2 M) was added Hunig's base (1.5 equiv.), HATU (1.5 equiv.) and the respective amine (1.2 equiv.). The mixture was stirred at room temperature. After consumption of starting material, the reaction mixture was quenched with water and extracted with dichloromethane. The combined organic layers were washed with brine solution, dried over Na$_2$SO$_4$ and concentrated under vacuum to afford the crude product. The crude product is further purified by column chromatography.

Compound 18: 2-(1,3-dimethyl-2,6-dioxo-2,3-di-hydro-1H-purin-7(6H)-yl)-N-(4-(thiophen-3-yl)phenyl)acetamide

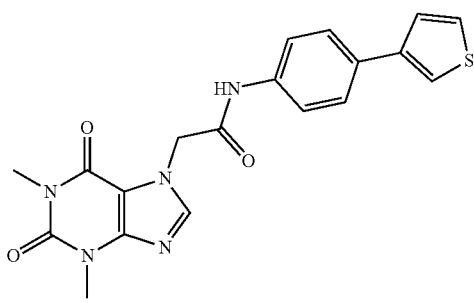 [SMILES: Cn1c(=O)c2c(ncn2CC(=O)Nc2ccc(-c3ccsc3)cc2)n(C)c1=O]

$^1$H NMR (400 MHz, DMSO-d$_6$) δ (ppm): 10.43 (s, 1H), 8.07 (s, 1H), 7.78-7.77 (m, 1H), 7.69-7.67 (m, 2H), 7.62-7.60 (m, 3H), 7.53-7.52 (m, 1H), 5.22 (s, 2H), 3.47 (s, 3H), 3.21 (s, 3H). LC-MS: m/z 396 (M+H) with a purity of 98%.

Compound 19: 2-(1,3-dimethyl-2,6-dioxo-2,3-di-hydro-1H-purin-7(6H)-yl)-N-(5-phenylpyridin-2-yl)acetamide

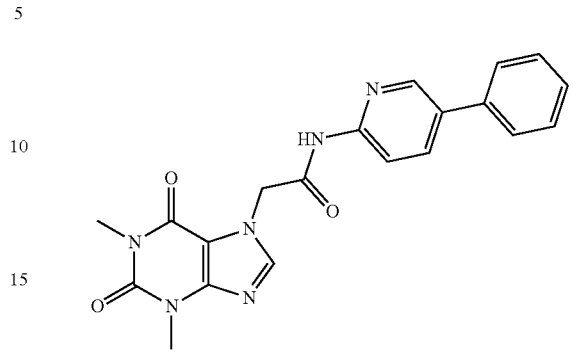

$^1$H NMR (400 MHz, DMSO-d$_6$) δ (ppm): 11.07 (bs, 1H), 8.68 (s, 1H), 8.04-8.12 (m, 3H), 7.70-7.72 (m, 2H), 7.48 (t, J=7.60 Hz, 2H), 7.38 (t, J=7.60 Hz, 1H), 5.29 (s, 2H), 3.19 (s, 3H). LC-MS: m/z 391 (M+H) with a purity of 98%.

Compound 20: tert-butyl 4-(4-(2-(1,3-dimethyl-2,6-dioxo-2,3-dihydro-1H-purin-7(6H)-yl) propana-mido)phenyl)piperazine-1-carboxylate

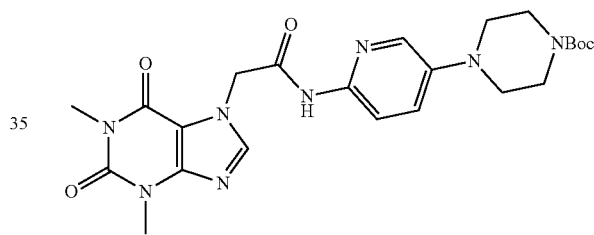

$^1$H NMR (600 MHz, C$_6$D6) δ (ppm): 9.84 (s, 1H), 8.39 (d, J=9.0 Hz, 1H), 7.92 (d, J=2.9 Hz, 1H), 7.01 (s, 1H), 6.64 (dd, J=9.0, 2.9 Hz, 1H), 4.35 (s, 2H), 3.26 (m, 4H), 3.26 (s, 3H), 3.25 (s, 3H), 2.53-2.40 (m, 4H), 1.45 (s, 10H). LC-MS: m/z 499 (M+H) with a purity of 99%

Compound 21: N-(5-(4-(3-chlorobenzyl)piperazin-1-yl)pyridin-2-yl)-2-(1,3-dimethyl-2,6-dioxo-2,3-dihydro-1H-purin-7(6H)-yl)acetamide

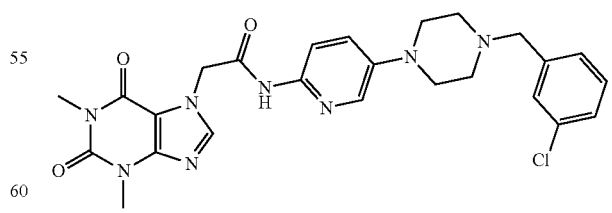

$^1$H NMR (600 MHz, CDCl$_3$) δ (ppm): 9.43 (s, 1H), 8.01-7.94 (m, 2H), 7.74 (s, 1H), 7.36 (s, 1H), 7.24 (ddd, J=12.1, 7.6, 3.3 Hz, 4H), 5.09 (s, 2H), 3.60 (s, 3H), 3.54 (s, 2H), 3.42 (s, 3H), 3.22-3.14 (m, 4H), 2.65-2.57 (m, 4H). LC-MS: m/z 523 (M+H), 521 (M−H) with a purity of 98%.

Compound 22: tert-butyl 4-(4-(2-(1,3-dimethyl-2,6-dioxo-2,3-dihydro-1H-purin-7(6H)-yl)acetamido)phenyl)piperazine-1-carboxylate

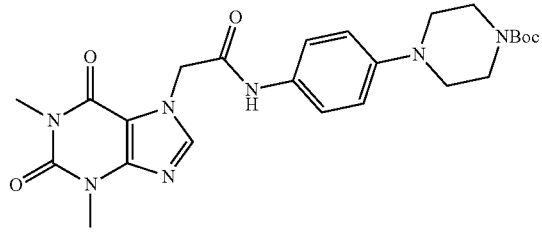 [SMILES: Cn1c(=O)c2c(ncn2CC(=O)Nc2ccc(N3CCN(C(=O)OC(C)(C)C)CC3)cc2)n(C)c1=O]

$^1$H NMR (600 MHz, CDCl$_3$) δ (ppm): 9.30 (s, 1H), 7.77 (s, 1H), 7.42 (d, J=9.1 Hz, 2H), 6.87 (d, J=8.9 Hz, 2H), 4.95 (s, 2H), 3.60 (s, 3H), 3.57 (m, 4H), 3.45 (s, 3H), 3.07 (m, 4H), 1.47 (s, 9H). LC-MS: m/z 498 (M+1), 496 (M−1) with purity of 99%.

Compound 23: tert-butyl 4-(4-(2-(1,3-dimethyl-2,6-dioxo-2,3-dihydro-1H-purin-7(6H)-yl) propanamido)phenyl)piperazine-1-carboxylate

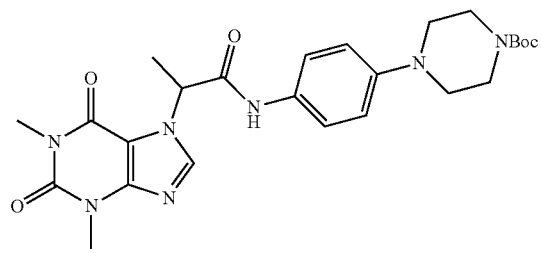 [SMILES: CC(C(=O)Nc1ccc(N2CCN(C(=O)OC(C)(C)C)CC2)cc1)n1cnc2c1c(=O)n(C)c(=O)n2C]

$^1$H NMR (600 MHz, MeOD-d$_4$) δ (ppm): 8.23 (s, 1H), 7.83 (s, 2H), 7.51 (d, J=7.6 Hz, 2H), 7.00 (d, J=7.6 Hz, 2H), 5.81 (q, J=7.2 Hz, 1H), 3.64 (bs, 7H), 3.39 (s, 3H), 3.15 (m, 4H), 1.96 (d, J=7.2 Hz, 3H), 1.55 (s, 9H). LC-MS: m/z 512 (M+1), 510 (M−1) with purity of 98%.

Amide coupling Method C: To a stirred solution of commercially available 2-(1,3-dimethyl-2,6-dioxo-2,3-dihydro-1H-purin-7(6H)-yl)acetic acid, 1 in dichloromethane (0.1 M) was added the respective amine (100 l equiv.), EDCI (1.2 equiv.) and HOBT (1.2 equiv.). The reaction mixture was stirred at room temperature for 16 h. After completion of starting material, water was added to the reaction mixture and product was extracted with 10% methanol/chloroform twice. The organic layer was dried over anhydrous Na2SO4, concentrated under vacuum to afford the crude product. The crude product is further purified by column chromatography.

Compound 24: 2-(1,3-dimethyl-2,6-dioxo-2,3-dihydro-1H-purin-7(6H)-yl)-N-(4-(oxazol-2-yl) phenyl)acetamide

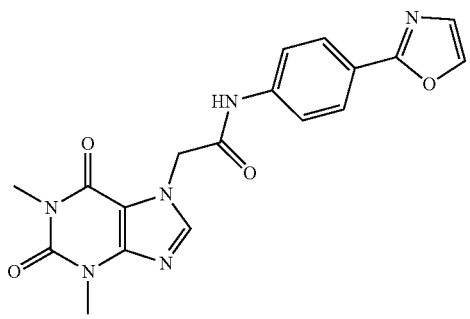

$^1$H NMR (400 MHz, DMSO-d$_6$) δ (ppm): 10.72 (s, 1H), 8.19 (s, 1H), 8.09 (s, 1H), 7.96-7.94 (d, J=8.8 Hz, 2H), 7.75-7.72 (d, J=8.8 Hz, 2H), 7.35 (s, 1H), 5.24 (s, 2H), 3.46 (s, 3H), 3.19 (s, 3H). LC-MS: m/z 379.3 (M+H) with a purity of 96.48%. HPLC: At 254 nm with a purity of 97%.

Amide coupling Method D: A stirred solution of commercially available 2-(1,3-dimethyl-2,6-dioxo-2,3-dihydro-1H-purin-7(6H)-yl)acetic acid, 1 (1 equiv.) in N,N-dimethylforamide (0.18 M), was added Hunig's base (1.5 equiv.), HOBt (1.5 equiv.), EDCI (1.5 equiv.) and the respective amine (1.5 equiv.). The mixture was stirred at room temperature for 16 h. After consumption of starting material, the reaction mixture was quenched with water and extracted with dichloromethane. The combined organic layers were washed with brine solution, dried over Na$_2$SO$_4$ and concentrated under vacuum. The crude compound was purified by column chromatography to afford the product.

Compound 25: 2-(1,3-dimethyl-2,6-dioxo-2,3-dihydro-1H-purin-7(6H)-yl)-N-(4-(pyridin-2-yl) phenyl)acetamide

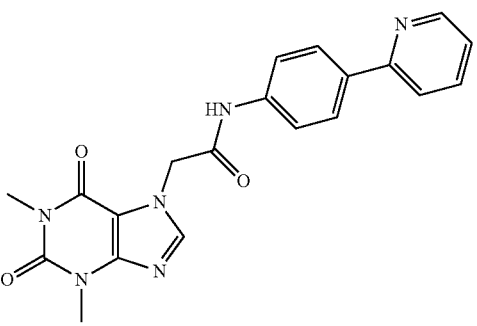 [SMILES: Cn1c(=O)c2c(ncn2CC(=O)Nc2ccc(-c3ccccn3)cc2)n(C)c1=O]

$^1$H NMR (400 MHz, DMSO-d$_6$) δ (ppm): 10.57 (s, 1H), 8.61-8.62 (m, 1H), 8.05-8.08 (m, 3H), 7.91 (d, J=8.00 Hz, 1H), 7.82-7.86 (m, 1H), 7.68 (d, J=8.00 Hz, 1H), 7.28-7.31 (m, 1H), 5.23 (s, 2H), 3.46 (s, 3H), 3.20 (s, 3H).

Compound 26: 2-(1,3-dimethyl-2,6-dioxo-2,3-dihydro-1H-purin-7(6H)-yl)-N-(4-(pyridin-3-yl)phenyl)acetamide

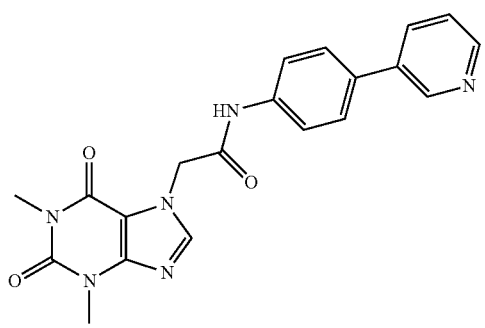 [SMILES: Cn1c(=O)c2c(ncn2CC(=O)Nc2ccc(-c3cccnc3)cc2)n(C)c1=O]

$^1$H NMR (400 MHz, DMSO-d$_6$) δ (ppm): 10.56 (s, 1H), 8.87 (s, 1H), 8.52-8.53 (m, 1H), 8.08 (s, 1H), 8.04-8.06 (m, 1H), 7.68-7.73 (m, 4H), 7.44-7.47 (m, 1H), 5.23 (s, 2H), 3.46 (s, 3H), 3.20 (s, 3H). LC-MS: m/z 391 (M+H) with a purity of 97%.

Compound 27: 2-(1,3-dimethyl-2,6-dioxo-2,3-dihydro-1H-purin-7(6H)-yl)-N-(2'-methoxy biphenyl-4-yl)acetamide

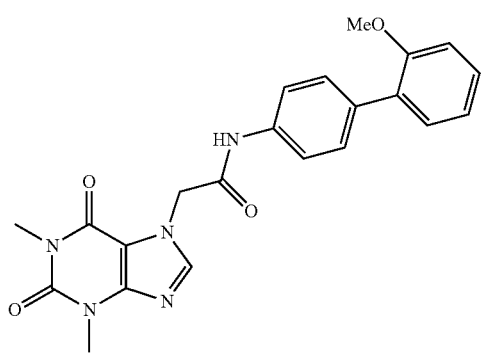 [SMILES: COc1ccccc1-c1ccc(NC(=O)Cn2cnc3c2c(=O)n(C)c(=O)n3C)cc1]

$^1$H NMR (400 MHz, DMSO-d$_6$) δ (ppm): 10.48 (s, 1H), 8.08 (s, 1H), 7.60-7.58 (m, 2H), 7.44-7.42 (m, 2H), 7.33-7.25 (m, 2H), 7.08 (d, J=8 Hz, 1H), 7.00 (t, J=7.4 Hz, 1H), 5.21 (s, 2H), 3.74 (s, 3H), 3.20 (s, 3H). LC-MS: m/z 420 (M+H) with a purity of 98%

Compound 28: 2-(1,3-dimethyl-2,6-dioxo-2,3-dihydro-1H-purin-7(6H)-yl)-N-(2'-methyl biphenyl-4-yl)acetamide

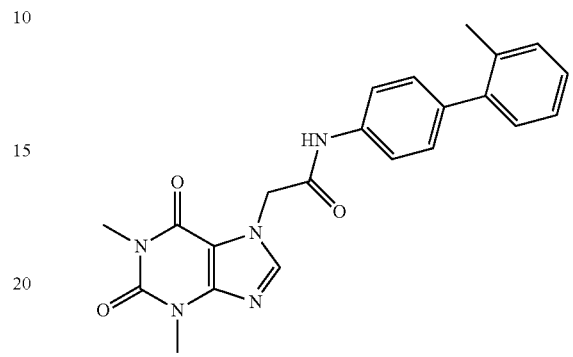

$^1$H NMR (400 MHz, MeOD-d$_4$) δ (ppm): 8.00 (s, 1H), 7.63-7.61 (m, 2H), 7.28-7.23 (m, 3H), 7.22-7.19 (m, 2H), 7.18-7.15 (m, 1H), 5.28 (s, 2H), 3.58 (s, 3H), 3.35 (s, 3H), 2.24 (s, 3H). LC-MS: m/z 404 (M+H) with a purity of 98%.

Compound 29: 2-(1,3-dimethyl-2,6-dioxo-2,3-dihydro-1H-purin-7(6H)-yl)-N-(3'-methyl biphenyl-4-yl)acetamide

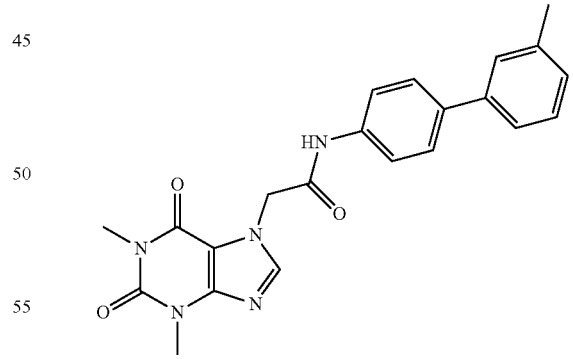

$^1$H NMR (400 MHz, MeOD-d$_4$) δ (ppm): 7.99 (s, 1H), 7.65-7.63 (m, 2H), 7.58-7.56 (m, 2H), 7.41 (s, 1H), 7.38-7.36 (m, 1H), 7.29 (t, J=7.8, 1H), 7.14-7.12 (m, 1H), 5.27 (s, 2H), 3.58 (s, 3H), 3.34 (s, 3H), 2.39 (s, 3H). LC-MS: m/z 404 (M+H) with a purity of 97%.

Compound 30: 2-(1,3-dimethyl-2,6-dioxo-2,3-di-hydro-1H-purin-7(6H)-yl)-N-(4'-methyl biphenyl-4-yl)acetamide

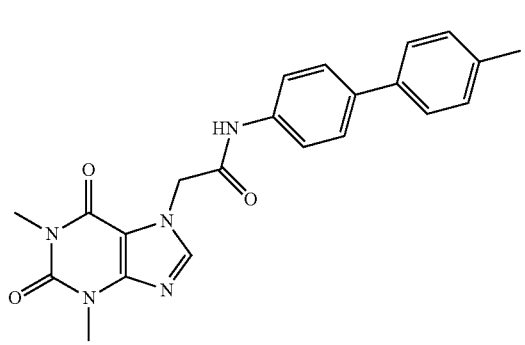

¹H NMR (400 MHz, MeOD-d₄) δ (ppm): 7.99 (s, 1H), 7.64-7.62 (m, 2H), 7.57-7.55 (m, 2H), 7.48 (d, J=8 Hz, 2H), 7.23 (d, J=8 Hz, 2H), 5.27 (s, 2H), 3.58 (s, 3H), 3.34 (s, 3H), 2.36 (s, 3H). LC-MS: m/z 404 (M+H) with a purity of 97%.

Compound 31: 2-(1,3-dimethyl-2,6-dioxo-2,3-di-hydro-1H-purin-7(6H)-yl)-N-(4'-(trifluoro methoxy) biphenyl-4-yl)acetamide

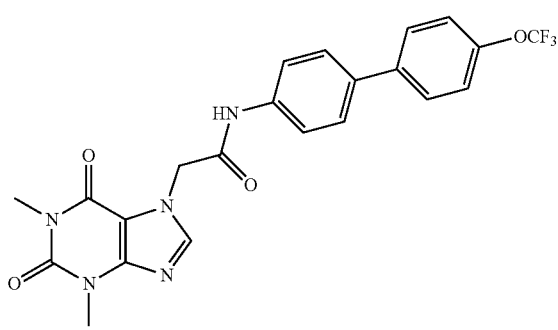 [SMILES: Cn1c(=O)c2c(ncn2CC(=O)Nc2ccc(-c3ccc(OC(F)(F)F)cc3)cc2)n(C)c1=O]

¹H NMR (400 MHz, DMSO-d₆) δ (ppm): 10.54 (s, 1H), 8.08 (s, 1H), 7.76 (d, J=8.40 Hz, 2H), 7.65-7.70 (m, 4H), 7.42 (d, J=8.40 Hz, 2H), 5.23 (s, 2H), 3.46 (s, 3H), 3.20 (s, 3H). LC-MS: m/z 474 (M+H) with a purity of 98%.

Compound 32: 2-(1,3-dimethyl-2,6-dioxo-2,3-di-hydro-1H-purin-7(6H)-yl)-N-(3'-methoxy biphenyl-4-yl)acetamide

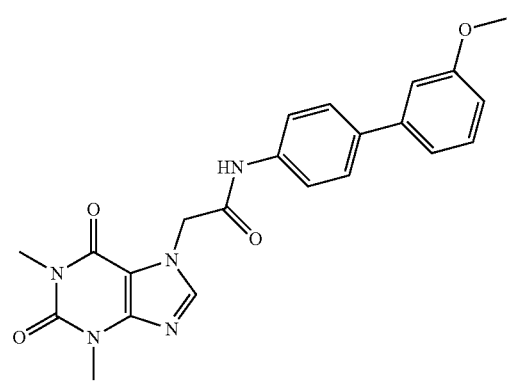

¹H NMR (400 MHz, DMSO-d₆) δ (ppm): 10.52 (s, 1H), 8.08 (s, 1H), 7.65 (s, 4H), 7.35 (t, J=8 Hz, 1H), 7.21 (d, J=8 Hz, 1H), 7.16 (m, 1H), 6.91-6.88 (m, 1H), 5.22 (s, 2H), 3.81 (s, 3H), 3.20 (s, 3H). LC-MS: m/z 420 (M+H) with a purity of 99%.

Compound 33: 2-(1,3-dimethyl-2,6-dioxo-2,3-di-hydro-1H-purin-7(6H)-yl)-N-(4-(2-methyl thiazol-4-yl)phenyl)acetamide

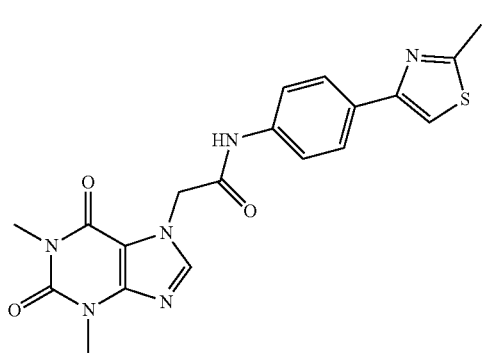

¹H NMR (400 MHz, DMSO-d₆) δ (ppm): 10.51 (s, 1H), 8.08 (s, 1H), 7.89 (d, J=8.8 Hz, 2H), 7.81 (s, 1H), 7.63 (d, J=8.8 Hz, 2H), 5.22 (s, 2H), 3.46 (s, 3H), 3.20 (s, 3H), 2.70 (s, 3H). LC-MS: m/z 411.5 (M+H) with a purity of 96%.

Compound 34: 2-(1,3-dimethyl-2,6-dioxo-2,3-dihydro-1H-purin-7(6H)-yl)-N-(4-(thiazol-2-yl) phenyl)acetamide

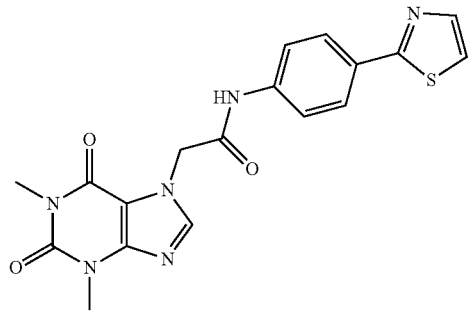 [SMILES: Cn1c(=O)c2c(ncn2CC(=O)Nc2ccc(-c3nccs3)cc2)n(C)c1=O]

$^1$H NMR (400 MHz, DMSO-d$_6$) δ (ppm): 10.67 (s, 1H), 8.08 (s,1H), 7.94-7.91 (m, 2H), 7.88 (d, J=3.2 Hz, 1H), 7.73-7.72 (m, 2H), 7.70 (m, 1H), 5.24 (s, 2H), 3.47 (s, 3H), 3.20 (s, 3H). LC-MS: m/z 397 (M+H) with a purity of 95%.

Amide coupling Method E: A solution of commercially available 2-(1,3-dimethyl-2,6-dioxo-2,3-dihydro-1H-purin-7(6H)-yl)acetic acid, 1 (1.3 equiv.) and triethylamine (2.1 equiv.) in dichloromethane (0.1 M) was cooled to 0° C. under nitrogen atmosphere and treated with isobutyl chloroformate (2.0 equiv.). The reaction mixture stirred for 30 minutes, treated with the respective amine (1.0 equiv.) and gently brought up to room temperature for 2-18 h until judged complete by LC-MS. It was partitioned between dichloromethane and saturated sodium bicarbonate. The organic phase was separated, washed with aqueous sodium chloride, dried over sodium sulfate and concentrated to dryness. The residue was purified using preparative HPLC to give the product.

Compound 35: 2-(1,3-dimethyl-2,6-dioxo-2,3-dihydro-1H-purin-7(6H)-yl)-N-(6-phenylpyridin-3-yl)acetamide

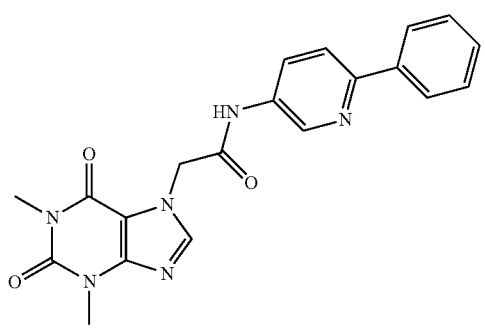 [SMILES: Cn1c(=O)c2c(ncn2CC(=O)Nc2ccc(-c3ccccc3)nc2)n(C)c1=O]

$^1$H NMR (400 MHz, DMSO-d$_6$) δ (ppm): 10.74 (s, 1H), 8.81-8.82 (m, 1H), 8.09-8.12 (m, 2H), 8.03-8.05 (m, 2H), 7.94-7.96 (m, 1H), 7.45-7.49 (m, 2H), 7.39-7.41 (m, 1H), 5.26 (s, 2H), 3.46 (s, 3H), 3.20 (s, 3H). LC-MS: m/z 391 (M+H) with a purity of 96%.

Compound 36: 2-(1,3-dimethyl-2,6-dioxo-2,3-dihydro-1H-purin-7(6H)-yl)-N-(5-phenylpyrazin-2-yl)acetamide

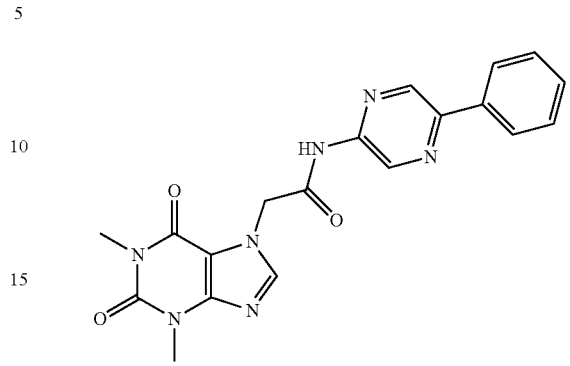

$^1$H NMR (400 MHz, MeOD-d$_4$) δ (ppm): 9.35 (bs, 1H), 8.86 (d, J=1.2 Hz, 1H), 8.00-8.02 (m, 3H), 7.42-7.52 (m, 3H), 5.37 (s, 2H), 3.58 (s, 3H), 3.33 (s, 3H). LC-MS: m/z 392 (M+H) with a purity of 99%.

Compound 37: 2-(1,3-dimethyl-2,6-dioxo-2,3-dihydro-1H-purin-7(6H)-yl)-N-(5-(4-fluoro phenyl)pyridin-2-yl)acetamide

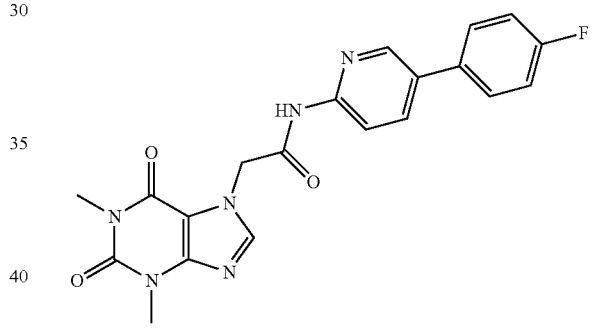

$^1$H NMR (400 MHz, DMSO-d$_6$) δ (ppm): 11.08 (bs, 1H), 8.67 (s, 1H), 8.06-8.11 (m, 3H), 7.75-7.78 (m, 2H), 7.29-7.33 (m, 2H), 5.29 (s, 2H), 3.46 (s, 3H), 3.19 (s, 3H). LC-MS: m/z 409 (M+H) with a purity of 98%.

Compound 38: methyl 4'-(2-(1,3-dimethyl-2,6-dioxo-2,3-dihydro-1H-purin-7(6H)-yl) acetamido)biphenyl-4-carboxylate

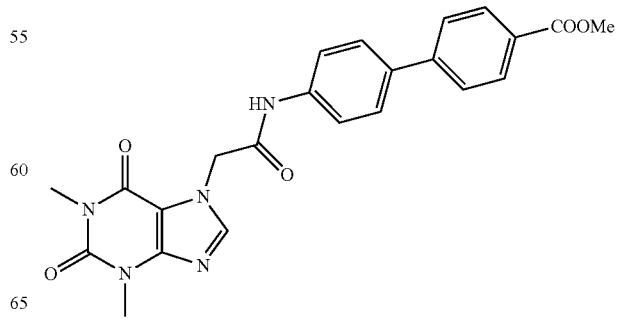

¹H NMR (400 MHz, DMSO-d₆) δ (ppm): 10.57 (s, 1H), 8.08 (s, 1H), 8.01 (d, J=8.40 Hz, 2H), 7.81 (d, J=8.40 Hz, 2H), 7.69-7.76 (m, 4H), 5.23 (s, 2H), 3.86 (s, 3H), 3.46 (s, 3H), 3.20 (s, 3H). LC-MS: m/z 448 (M+H) with a purity of 97%.

Compound 39: 2-(1,3-dimethyl-2,6-dioxo-2,3-dihydro-1H-purin-7(6H)-yl)-N-(3-phenyl isoxazol-5-yl)acetamide

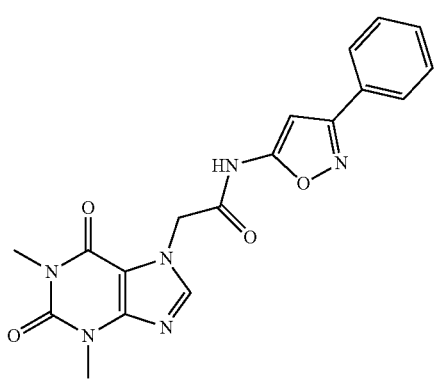 [SMILES: Cn1c(=O)c2c(ncn2CC(=O)Nc2cc(-c3ccccc3)no2)n(C)c1=O]

¹H NMR (400 MHz, DMSO-d₆) δ (ppm): 12.28 (s, 1H), 8.08 (s, 1H), 7.82 (s, 2H), 7.49 (s, 3H), 6.68 (s, 1H), 5.29 (s, 2H), 3.46 (s, 3H), 3.19 (s, 3H). LC-MS: m/z 381 (M+H) with a purity of 97%.

Compound 40: 2-(1,3-dimethyl-2,6-dioxo-2,3-dihydro-1H-purin-7(6H)-yl)-N-(4-(oxazol-5-yl) phenyl)acetamide

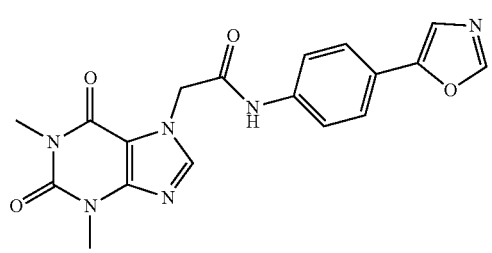 [SMILES: Cn1c(=O)c2c(ncn2CC(=O)Nc2ccc(-c3cnco3)cc2)n(C)c1=O]

¹H NMR (400 MHz, DMSO-d₆) δ (ppm): 10.59 (s, 1H), 8.39 (s, 1H), 8.07 (s, 1H), 7.68 (m, 4H), 7.59 (s, 1H), 5.22 (s, 2H), 3.46 (s, 3H), 3.20 (s, 3H). LC-MS: m/z 381 (M+H) with a purity of 95%.

Compound 41: 2-(1,3-dimethyl-2,6-dioxo-2,3-dihydro-1H-purin-7(6H)-yl)-N-(5-(thiazol-2-yl) pyridin-2-yl)acetamide

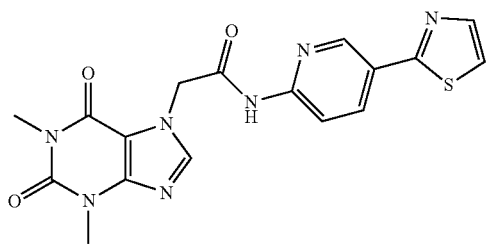 [SMILES: Cn1c(=O)c2c(ncn2CC(=O)Nc2ccc(-c3nccs3)cn2)n(C)c1=O]

¹H NMR (400 MHz, DMSO-d₆) δ (ppm): 11.27 (s, 1H), 8.93 (d, J=2 Hz, 1H), 8.32 (dd, J=8.8, 2.4 Hz, 1H), 8.11-8.09 (m, 1H), 8.07 (s, 1H), 7.95 (d, J=3.2 Hz, 1H), 7.82 (d, J=3.2 Hz, 1H), 5.31 (s, 2H), 3.46 (s, 3H), 3.19 (s, 3H). LC-MS: m/z 398 (M+H) with a purity of 96%.

Removal of Boc protecting group: To a mixture of tert-butyl 4-(6-(2-(1,3-dimethyl-2,6-dioxo-2,3-dihydro-1H-purin-7(6H)-yl)acetamido)pyridin-3-yl)piperazine-1-carboxylate, 1 (1 equiv.) in dichloromethane (0.1 M) was added trifluroacetic acid (10 equiv.) at room temperature. The reaction mixture was allowed to stir for 2 h followed by which the volatiles were evaporated. The resulting mass was then subjected to purification on a preparative TLC.

Compound 42: 2-(1,3-dimethyl-2,6-dioxo-2,3-dihydro-1H-purin-7(6H)-yl)-N-(5-(piperazin-1-yl) pyridin-2-yl)acetamide

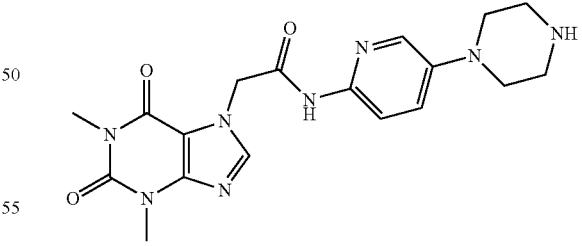

¹H NMR (600 MHz, CDCl₃: MeOD (10:1)) δ (ppm): 7.86 (d, J=8.9 Hz, 1H), 7.83 (d, J=2.8 Hz, 1H), 7.69 (s, 1H), 7.20-7.16 (m, 1H), 5.06 (s, 2H), 3.47 (s, 3H), 3.25 (s, 3H), 3.22 (dt, J=3.9, 1.6 Hz, 1H), 3.14 (dd, J=6.2, 3.9 Hz, 3H), 3.07-3.03 (m, 4H). LC-MS: m/z 399 (M+H) with a purity of 96%.

Compound 43: (S)-2-(1,3-dimethyl-2,6-dioxo-2,3-dihydro-1H-purin-7(6H)-yl)-N-(4-(2-methyl piperazin-1-yl)phenyl)acetamide

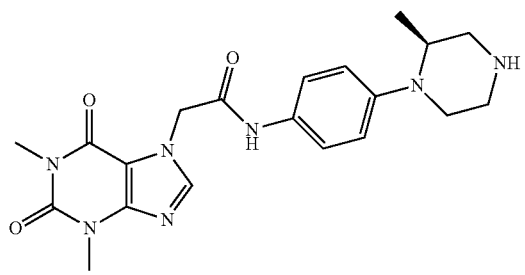 [SMILES: C[C@H]1CNCCN1c1ccc(NC(=O)Cn2cnc3c2c(=O)n(C)c(=O)n3C)cc1]

$^1$H NMR (400 MHz, CDCl$_3$) δ (ppm): 9.37 (s, 1H), 7.77 (s, 1H), 7.45 (d, J=8.8 Hz, 2H), 6.92 (d, J=8.8 Hz, 2H), 4.95 (s, 2H), 3.61 (m, 4H), 3.47 (s, 3H), 3.24-3.06 (m, 5H), 2.91-2.87 (m, 1H), 0.99 (d, J=6.4 Hz, 3H). LC-MS: m/z 412 (M+H) with a purity of 99%.

Compound 44: (R)-2-(1,3-dimethyl-2,6-dioxo-2,3-dihydro-1H-purin-7(6H)-yl)-N-(4-(2-methyl piperazin-1-yl)phenyl)acetamide

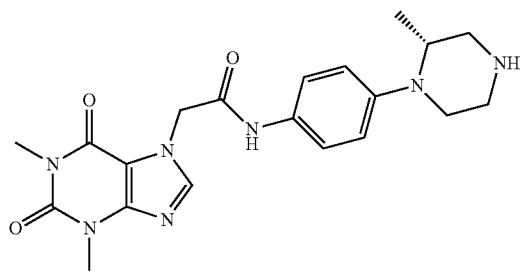 [SMILES: C[C@@H]1CNCCN1c1ccc(NC(=O)Cn2cnc3c2c(=O)n(C)c(=O)n3C)cc1]

$^1$H NMR (400 MHz, CDCl$_3$) δ (ppm): 9.37 (s, 1H), 7.77 (s, 1H), 7.45 (d, J=8.8 Hz, 2H), 6.92 (d, J=8.8 Hz, 2H), 4.95 (s, 2H), 3.61 (m, 4H), 3.47 (s, 3H), 3.24-3.06 (m, 5H), 2.91-2.87 (m, 1H), 0.99 (d, J=6.4 Hz, 3H). LC-MS: m/z 412 (M+H) with a purity of 99%.

Acylation Method A: To a solution of 2-(1,3-dimethyl-2,6-dioxo-2,3-dihydro-1H-purin-7(6H)-yl)-N-(5-(piperazin-1-yl)pyridin-2-yl)acetamide, 1 (1 equiv.) in dry N,N-dimethylformamide (0.07 M) was added Hunig's base (2 equiv.) and the respective acid chloride (1 equiv.). The reaction was stirred for 16 h at room temperature then quenched by the addition of distilled water. The solvent was removed in vacuo, and the crude material was partitioned between chloroform and saturated NaHCO$_3$. The crude product was further purified by column chromatography.

Compound 45: N-(5-(4-benzoylpiperazin-1-yl)pyridin-2-yl)-2-(1,3-dimethyl-2,6-dioxo-2,3-dihydro-1H-purin-7(6H)-yl)acetamide

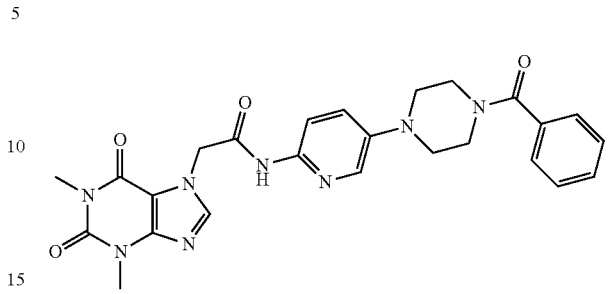

$^1$H NMR (600 MHz, CDCl$_3$) δ (ppm): 9.53 (s, 1H), 8.02 (d, J=8.9 Hz, 1H), 7.98 (d, J=1.9 Hz, 1H), 7.73 (s, 1H), 7.43 (s, 5H), 7.27 (dd, J=9.1, 3.0 Hz, 1H), 5.11 (s, 2H), 3.93 (br s, 2H), 3.60 (m, 5H), 3.41 (s, 3H), 3.16 (br d, J=59.6 Hz, 4H). LC-MS: 503 (M+H), 524 (M+Na) with a purity of 92%.

Compound 46: (S)—N-(4-(4-benzoyl-2-methylpiperazin-1-yl)phenyl)-2-(1,3-dimethyl-2,6-dioxo-2,3-dihydro-1H-purin-7(6H)-yl)acetamide

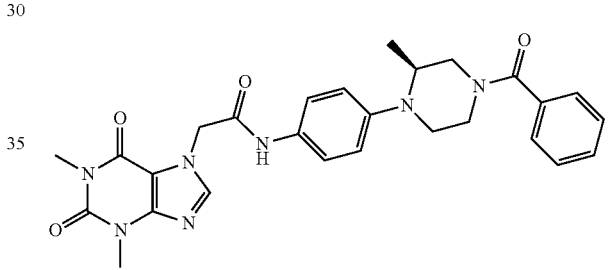

$^1$H NMR (400 MHz, CDCl$_3$) δ (ppm): 9.31 (s, 1H), 7.76 (s, 1H), 7.44-7.42 (m, 7H), 6.87 (d, J=8.8 Hz, 2H), 4.94 (s, 2H), 3.61 (m, 4H), 3.46 (m, 5H), 1.55 (s, 7H). LC-MS: m/z 516 (M+H) with a purity of 98%.

Compound 47: 2-(1,3-dimethyl-2,6-dioxo-2,3-dihydro-1H-purin-7(6H)-yl)-N-(5-(4-(3,3-dimethylbutanoyl)piperazin-1-yl)pyridin-2-yl)acetamide

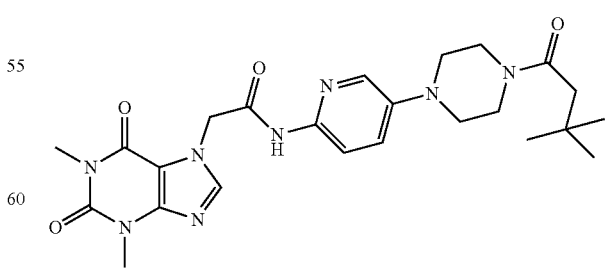

$^1$H NMR (600 MHz, C$_6$D$_6$) δ (ppm): 6 9.97 (s, 1H), 8.44 (d, J=9.1 Hz, 1H), 7.94 (d, J=2.9 Hz, 1H), 7.09 (s, 1H), 6.71 (dd, J=9.1, 3.0 Hz, 1H), 4.49 (s, 2H), 3.55 (s, 2H), 3.29 (s, 3H), 3.27 (s, 3H), 2.89 (s, 2H), 2.45 (d, J=39.6 Hz, 4H), 2.03 (s, 2H), 1.10 (s, 9H). LC-MS: m/z 497 (M+H), 495 (M−H) with a purity of 97%.

Compound 48: 2-(1,3-dimethyl-2,6-dioxo-2,3-dihydro-1H-purin-7(6H)-yl)-N-(5-(piperazin-1-yl)pyridin-2-yl)acetamide

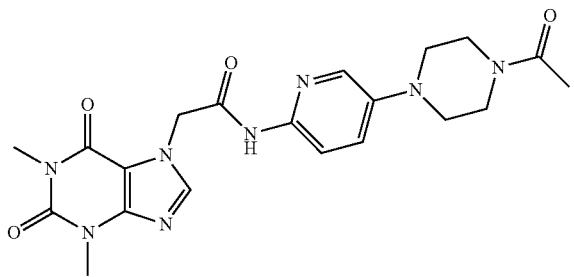 [SMILES: CC(=O)N1CCN(c2ccc(NC(=O)Cn3cnc4c3c(=O)n(C)c(=O)n4C)nc2)CC1]

¹H NMR (600 MHz, C₆D₆) δ (ppm): δ 9.50 (s, 1H), 8.47 (d, J=9.2 Hz, 1H), 7.88 (d, J=2.6 Hz, 1H), 6.86 (s, 1H), 6.66 (dd, J=9.1, 3.0 Hz, 1H), 4.12 (s, 2H), 3.47-3.42 (m, 2H), 3.23 (s, 6H), 3.01 (s, 3H), 2.66-2.59 (m, 2H), 2.39-2.34 (m, 2H), 2.25-2.21 (m, 2H). LC-MS: m/z 439 (M−H), 441 (M+H) with a purity of 97%.

Compound 49: N-(5-(4-(4-chlorobenzoyl)piperazin-1-yl)pyridin-2-yl)-2-(1,3-dimethyl-2,6-dioxo-2,3-dihydro-1H-purin-7(6H)-yl)acetamide

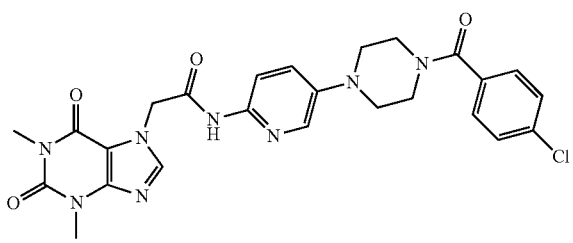 [SMILES: Cn1c(=O)c2c(ncn2CC(=O)Nc2ccc(N3CCN(C(=O)c4ccc(Cl)cc4)CC3)cn2)n(C)c1=O]

¹H NMR (600 MHz, CDCl₃) δ (ppm): 9.53 (s, 1 H), 8.03 (d, J=9.0 Hz, 1H), 7.97 (d, J=2.9 Hz, 1H), 7.73 (s, 1H), 7.40 (m, J=8.7 Hz, 4H), 7.28-7.26 (m, 1H), 5.11 (s, 2H), 3.91 (s, 2H), 3.60 (s, 4H), 3.48 (s, 1H), 3.41 (s, 3H), 3.17 (bs, 4H). LC-MS: m/z 537 (M+1) and 535 (M−1) with a purity of 98%.

Compound 50: 2-(1,3-dimethyl-2,6-dioxo-2,3-dihydro-1H-purin-7(6H)-yl)-N-(5-(4-(thiophene-2-carbonyl)piperazin-1-yl)pyridin-2-yl)acetamide

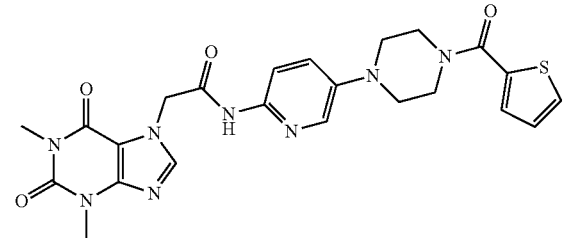 [SMILES: Cn1c(=O)c2c(ncn2CC(=O)Nc2ccc(N3CCN(C(=O)c4cccs4)CC3)cn2)n(C)c1=O]

¹H NMR (600 MHz, DMSO-d₆) δ (ppm): 10.77 (s, 1H), 8.07 (d, J=3.0 Hz, 1H), 8.06 (s, 1H), 7.86 (d, J=9.0 Hz, 1H), 7.78 (dd, J=5.0, 1.1 Hz, 1H), 7.46 (dd, J=3.6, 1.0 Hz, 1H), 7.44 (dd, J=9.1, 2.9 Hz, 1H), 7.15 (dd, J=5.0, 3.6 Hz, 1H), 5.22 (s, 2H), 3.79 (m, 4H), 3.45 (s, 3H), 3.22 (m, 4H), 3.19 (s, 3H). LC-MS: m/z 509 (M+H), 507 (M−H) with a purity of 99%.

Acylation Method B: To a mixture of the 2-(1,3-dimethyl-2,6-dioxo-2,3-dihydro-1H-purin-7(6H)-yl)-N-(5-(piperazin-1-yl)pyridin-2-yl)acetamide, 1 (1 equiv.) and the respective acid (1 equiv.) in N,N-dimethylforamide (0.06 M), HATU (1.2 equiv.) and Hunig's base (3 equiv.) in a dropwise fashion at room temperature. The reaction mixture was allowed to stir for 30 min followed by which it was quenched with saturated NaHCO₃ solution. The resulting mixture was extracted with ethyl acetate twice and the combined organic layer was evaporated and the crude products were subjected to purification on a preparative TLC plate.

Compound 51: 2-(1,3-dimethyl-2,6-dioxo-2,3-dihydro-1H-purin-7(6H)-yl)-N-(5-(4-(3-fluoro benzoyl)piperazin-1-yl)pyridin-2-yl)acetamide

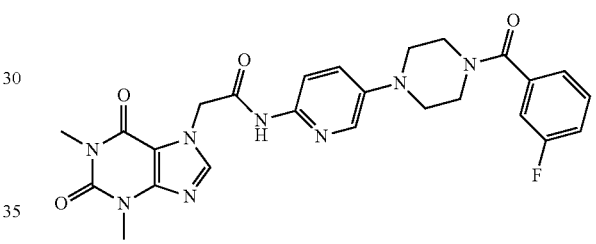

¹H NMR (600 MHz, DMSO-d₆) δ (ppm): 10.80 (s, 1H), 8.09-8.02 (m, 2H), 7.85 (d, J=9.1 Hz, 1H), 7.52 (td, J=7.9, 5.8 Hz, 1H), 7.43 (dd, J=9.1, 3.0 Hz, 1H), 7.36-7.22 (m, 3H), 5.21 (s, 2H), 3.76 (bs, 2H), 3.45 (s, 3H), 3.24 (bs, 2H), 3.18 (s, 3H), 3.13 (bs, 2H). LC-MS: m/z 521 (M+1), 519 (M−1) with a purity of 95%.

Compound 52: 2-(1,3-dimethyl-2,6-dioxo-2,3-dihydro-1H-purin-7(6H)-yl)-N-(5-(4-(4-fluoro benzoyl)piperazin-1-yl)pyridin-2-yl)acetamide

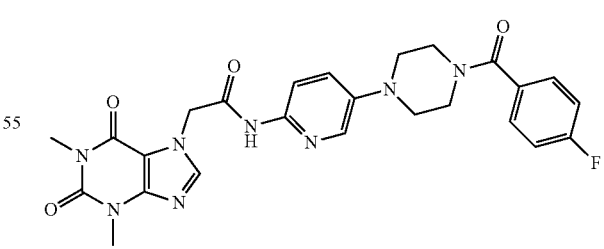

¹H NMR (600 MHz, CDCl₃) δ (ppm): 9.69 (s, 1H), 8.04 (d, J=9.1 Hz, 1H), 7.96 (d, J=2.8 Hz, 1H), 7.74 (s, 1H), 7.50-7.40 (m, 2H), 7.30 (dd, J=9.2, 3.0 Hz, 1H), 7.15-7.08 (m, 2H), 5.12 (s, 2H), 3.90 (bs, 3H), 3.66 (bs, 1H), 3.60 (s, 3H), 3.41 (s, 3H), 3.17 (s, 4H). LC-MS: m/z 519 (M−H) and purity of 98%.

Alkylation Procedure: To a mixture of the 2-(1,3-dimethyl-2,6-dioxo-2,3-dihydro-1H-purin-7(6H)-yl)-N-(5-(piperazin-1-yl)pyridin-2-yl)acetamide, 1 (1 equiv.) in N,N-dimethylforamide (0.08 M) and Hunig's base was added the respective arylbromide (1 equiv.) at room temperature. The reaction mixture was allowed to stir for 24 h followed by evaporation of the volatiles and addition water. The resulting mixture was extracted with ethyl acetate trice and the organic layer was evaporated and the crude products were subjected to purification on a preparative TLC plate.

Compound 53: N-(5-(4-benzylpiperazin-1-yl)pyridin-2-yl)-2-(1,3-dimethyl-2,6-dioxo-2,3-dihydro-1H-purin-7(6H)-yl)acetamide

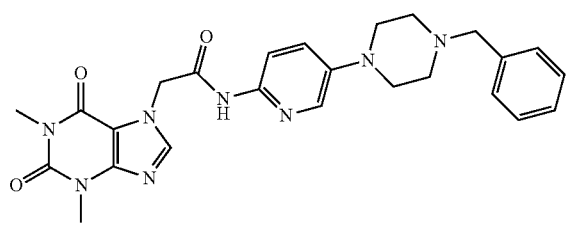 [SMILES: Cn1c(=O)c2c(ncn2CC(=O)Nc2ccc(N3CCN(Cc4ccccc4)CC3)cn2)n(C)c1=O]

$^1$H NMR (600 MHz, CDCl$_3$) δ (ppm): 9.64 (s, 1H), 8.01 (d, J=2.9 Hz, 1H), 7.99 (d, J=9.1 Hz, 1H), 7.76 (s, 1H), 7.37 (m, 5H), 7.33 (d, J=4.3 Hz, 1H), 5.10 (s, 2H), 3.59 (s, 3H), 3.57 (s, 2H), 3.40 (s, 3H), 3.22-3.13 (m, 4H), 2.71-2.45 (m, 4H). LC-MS: 489 (M+H) with a purity of 94%.

Compound 54: N-(5-(4-(3,5-difluorobenzyl)piperazin-1-yl)pyridin-2-yl)-2-(1,3-dimethyl-2,6-dioxo-2,3-dihydro-1H-purin-7(6H)-yl)acetamide

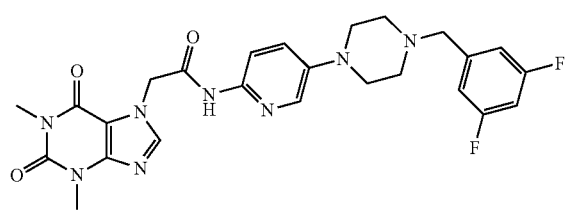 [SMILES: Cn1c(=O)c2c(ncn2CC(=O)Nc2ccc(N3CCN(Cc4cc(F)cc(F)c4)CC3)cn2)n(C)c1=O]

$^1$H NMR (600 MHz, CDCl$_3$) δ (ppm): 9.33 (s, 1H), 8.02-7.94 (m, 2H), 7.73 (d, J=13.6 Hz, 1H), 7.25-7.22 (m, 1H), 6.90 (t, J=13.6 Hz, 2H), 6.74-6.65 (m, 1H), 5.13-5.04 (m, 2H), 3.63-3.59 (m, 3H), 3.57-3.52 (m, 2H), 3.45-3.39 (m, 3H), 3.18 (dd, J=14.6, 9.6 Hz, 4H), 2.62 (s, 4H). LC-MS: m/z 525 (M+H), 523 (M−H) with purity of 97%.

Reductive amination procedure: To a mixture of the 2-(1,3-dimethyl-2,6-dioxo-2,3-dihydro-1H-purin-7(6H)-yl)-N-(5-(piperazin-1-yl)pyridin-2-yl)acetamide, 1 (1 equiv.) and the respective aldehyde (1 equiv.) in dichloroethane (0.1 M) was added acetic acid (2 equiv.) followed by triacetoxy sodium borohydride (1.4 equiv.) at room temperature. The reaction was stirred for an hour and then quenched with saturated NaHCO$_3$ (1 mL). The organics were extracted in ethyl acetate trice and the combined organic layers were dried. The residue was purified by using preparative TLC.

Compound 55: 2-(1,3-dimethyl-2,6-dioxo-2,3-dihydro-1H-purin-7(6H)-yl)-N-(5-(4-(2-fluorobenzyl)piperazin-1-yl)pyridin-2-yl)acetamide

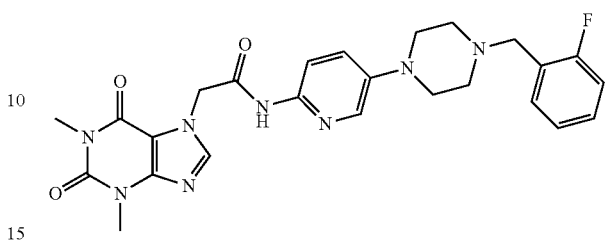

$^1$H NMR (600 MHz, CDCl$_3$) δ (ppm): 9.61 (s, 1H), 7.99-7.98 (m, 1H), 7.96 (d, J=9.2 Hz, 1H), 7.73 (s, 1H), 7.45-7.38 (m, 1H), 7.29-7.24 (m, 1H), 7.22 (dd, J=9.1, 3.0 Hz, 1H), 7.15-7.10 (m, 1H), 7.07-7.02 (m, 1H), 5.10 (s, 2H), 3.67 (s, 2H), 3.59 (s, 3H), 3.40 (s, 3H), 3.24-3.13 (m, 4H), 2.67 (s, 4H). LC-MS: m/z 507 (M+1), 505 (M−1) with purity of 96%.

Compound 56: 2-(1,3-dimethyl-2,6-dioxo-2,3-dihydro-1H-purin-7(6H)-yl)-N-(5-(4-(4-fluorobenzyl)piperazin-1-yl)pyridin-2-yl)acetamide

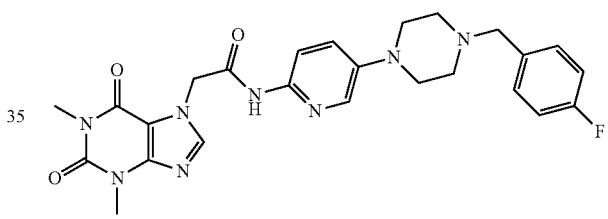

$^1$H NMR (600 MHz, CDCl$_3$) δ (ppm): 9.29 (s, 1H), 7.98 (d, J=9.1 Hz, 1H), 7.95 (d, J=2.4 Hz, 1H) 7.73 (s, 1H), 7.38 (m, 2H), 7.26-7.20 (m, 1H), 7.04 (t, J=8.6 Hz, 2H), 5.08 (s, 2H), 3.64 (bs, 2H), 3.60 (s, 3H), 3.42 (s, 3H), 3.25 (bs, 4H), 2.70 (bs, 4H). LC-MS: m/z 507 (M+1), 505 (M−1) with a purity of 96%.

Compound 57: 2-(1,3-dimethyl-2,6-dioxo-2,3-dihydro-1H-purin-7(6H)-yl)-N-(5-(4-(3-fluoro benzyl) piperazin-1-yl)pyridin-2-yl)acetamide

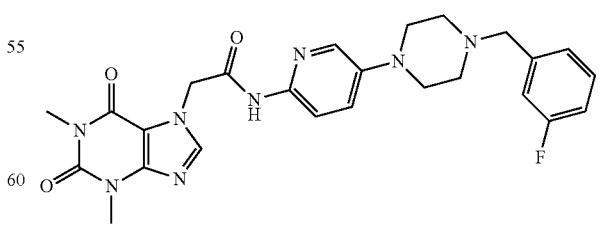

$^1$H NMR (600 MHz, CDCl$_3$) δ (ppm): 9.48 (s, 1H), 8.01 (s, 1H), 7.99 (m, 1H), 7.76 (s, 1H), 7.34-7.29 (m, 1H), 7.28-7.23 (m, 1H), 7.15-7.09 (m, 2H), 6.99 (ddd, J=7.8, 5.2, 1.8 Hz, 1H), 5.12 (s, 2H), 3.65-3.61 (m, 3H), 3.62-3.58 (m, 2H), 3.44 (s, 3H), 3.25-3.16 (m, 4H), 2.66 (m, 4H). LC-MS: m/z 507 (M+H), 505 (M−H) with a purity of 95%.

Mitsunobu reaction conditions:

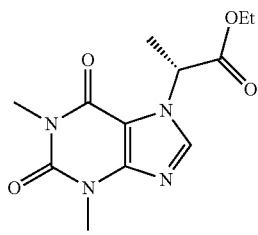

To a stirred solution of commercially available 1,3-dimethyl-1H-purine-2,6(3H,7H)-dione, 1 (2 equiv.), (S)-ethyl 2-hydroxypropanoate, 2 (1 equiv.) and triphenyl phosphine (1.45 g, 5.555) in tetrahydrofuran (0.14 M) was added DIAD (2 equiv.) dropwise at room temperature, and the resulting reaction mixture was stirred for 5 h. After completion of starting material, the reaction mixture was diluted with water and extracted with ethyl acetate twice. The combined organic layers were washed with brine, dried over anhydrous $Na_2SO_4$, and concentrated under vacuum. The crude compound was purified by column chromatography to afford the product.

Alkylation Method A:

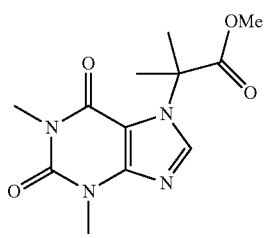 [SMILES: COC(=O)C(C)(C)n1cnc2c1c(=O)n(C)c(=O)n2C]

To a solution of commercially available 1,3-dimethyl-1H-purine-2,6(3H,7H)-dione, 1 (1 equiv.) in N,N-dimethylformamide (0.28 M) was added methyl 2-bromo-2-methylpropanoate, 2 (1.2 equiv.), $K_2CO_3$ (2 equiv.) at room temperature and warmed to 80° C. for 20 h. After completion, the reaction mixture was cooled to room temperature; water was added and mixture was extracted with ethyl acetate trice. The combined ethyl acetate layers were washed with water, brine, dried over anhydrous $Na_2SO_4$, filtered, rotary evaporated and dried under vacuum to afford the product.

Alkylation Method B:

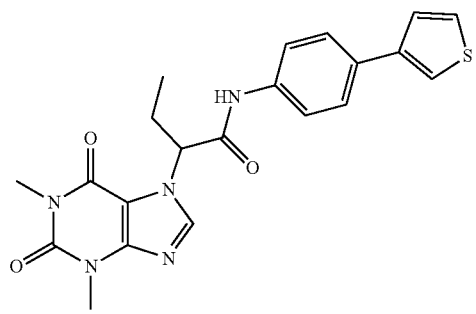 [SMILES: CCC(C(=O)Nc1ccc(-c2ccsc2)cc1)n1cnc2c1c(=O)n(C)c(=O)n2C]

A solution of 1,3-dimethyl-1H-purine-2,6(3H,7H)-dione, 2 (1 equiv.) and 2-bromo-N-(4-(thiophen-3-yl)phenyl)butanamide, 1 (1.1 equiv.) in N,N-dimethylformamide (0.1 M) cooled to 0° C. under nitrogen atmosphere, was treated with sodium hydride (2.5 equiv., 60% mineral oil). The mixture was stirred for 18 h at room temperature under nitrogen atmosphere and was partitioned between dichloromethane and water. The organic phase was separated, washed with aqueous sodium chloride, dried over sodium sulfate and concentrated to dryness. The residue was purified using preparative HPLC to give the final product.

Hydrolysis Conditions:

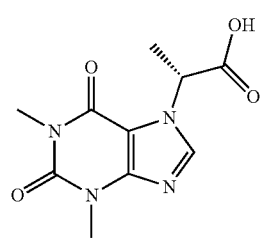 [SMILES: C[C@H](C(=O)O)n1cnc2c1c(=O)n(C)c(=O)n2C]

To a stirred solution of (R)-ethyl 2-(1,3-dimethyl-2,6-dioxo-2,3-dihydro-1H-purin-7(6H)-yl)propanoate, 3 (1 equiv.) in tetrahydrofuran (0.18 M), methanol (0.36 M) and water (0.36 M) was added $LiOH.H_2O$ (1.5 equiv.) at room temperature and resulting reaction mixture was stirred at room temperature for 2 h. After completion of starting material, the reaction mixture was concentrated and the residue was dissolved in water and washed with ethyl acetate twice and acidified with aq.$KHSO_4$; product was extracted with 10% methanol/chloroform twice. The combined organic layers were dried using $Na_2SO_4$, concentrated under vacuum to give the product.

Compound 58 (R)-2-(1,3-dimethyl-2,6-dioxo-2,3-dihydro-1H-purin-7(6H)-yl)-N-(4-(thiophen-3-yl)phenyl)propanamide

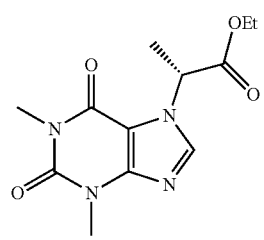 [SMILES: C[C@H](C(=O)O)n1cnc2c1c(=O)n(C)c(=O)n2C]

Step 1: Preparation of (R)-ethyl 2-(1,3-dimethyl-2,6-dioxo-2,3-dihydro-1H-purin-7(6H)-yl)propanoate Intermediate was prepared using the Mitsunobu conditions as described. $^1$H NMR (400 MHz, $CDCl_3$) δ (ppm): 7.75 (s, 1H), 5.63-5.58(q, J=6.8 Hz, 1H), 4.26-4.24 (q, J=6.8 Hz, 2H), 3.61 (s, 3H), 3.39 (s, 3H), 1.86-1.84 (d, J=6.8 Hz, 3H), 1.29-1.25 (t, J=6.8 Hz, 3H). LC-MS: m/z 281.3 (M+H) with a purity of 43%.

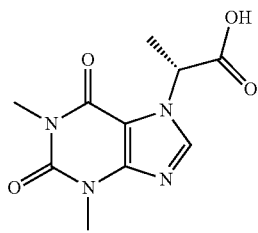

Step 2: Preparation of (R)-2-(1,3-dimethyl-2,6-dioxo-2,3-dihydro-1H-purin-7(6H)-yl) propanoic acid Intermediate was prepared using the hydrolysis condition as described. $^1$H NMR (400 MHz, DMSO-d$_6$) δ (ppm): 13.25 (brs, 1H), 8.20 (s, 1H), 5.50-5.44 (q, J=7.6 Hz, 1H), 3.44 (s, 3H), 3.24 (s, 3H), 1.76-1.74 (d, J=7.6 Hz, 3H). LC-MS: m/z 250.9 (M+H) with a purity of 97%.

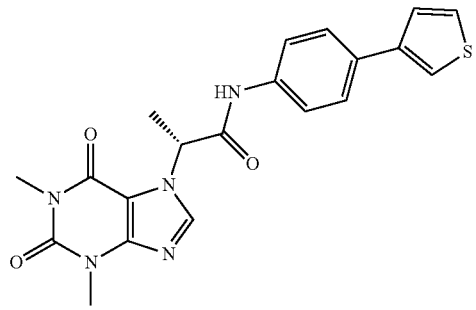 [SMILES: C[C@H](C(=O)Nc1ccc(-c2ccsc2)cc1)n1cnc2c1c(=O)n(C)c(=O)n2C]

Step 3: Preparation of (R)-2-(1,3-dimethyl-2,6-dioxo-2,3-dihydro-1H-purin-7(6H)-yl)-N-(4-(thiophen-3-yl)phenyl)propanamide The final product was prepared using amide coupling method A reaction conditions as described.

$^1$H NMR (400 MHz, DMSO-d$_6$) δ (ppm): 10.47 (s, 1H), 8.33 (s, 1H), 7.79 (s, 1H), 7.69-7.67 (d, J=8.8 Hz, 2H), 7.62-7.60 (d, J=8.4 Hz, 3H), 7.53-7.52 (d, J=4.8 Hz, 1H), 5.71-5.69 (q, J=6.9 Hz, 1H), 3.46 (s, 3H), 3.20 (s, 3H), 1.84-1.83 (d, J=6.8 Hz, 3H). LC-MS: m/z 410.13 (M+H) with a purity of 99%.

Compound 59: (S)-2-(1,3-dimethyl-2,6-dioxo-2,3-dihydro-1H-purin-7(6H)-yl)-N-(4-(thiophen-3-yl)phenyl)propanamide

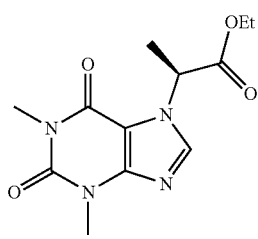

Step 1: Preparation of (S)-ethyl 2-(1,3-dimethyl-2,6-dioxo-2,3-dihydro-1H-purin-7(6H)-yl)propanoate Intermediate was prepared using the Mitsunobu conditions as described. $^1$H NMR (400 MHz, CDCl$_3$) δ (ppm): 7.75 (s, 1H), 5.63-5.58(q, J=6.8 Hz, 1H), 4.26-4.24 (q, J=6.8 Hz, 2H), 3.61 (s, 3H), 3.39 (s, 3H), 1.86-1.84 (d, J=6.8 Hz, 3H), 1.29-1.25 (t, J=6.8 Hz, 3H). LC-MS: m/z 281.4 (M+H) with a purity of 32%.

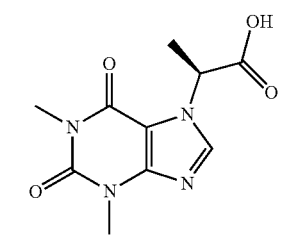 [SMILES: C[C@@H](C(=O)O)n1cnc2c1c(=O)n(C)c(=O)n2C]

Step 2: Preparation of (S)-2-(1,3-dimethyl-2,6-dioxo-2,3-dihydro-1H-purin-7(6H)-yl) propanoic acid Intermediate was prepared using the hydrolysis condition as described. $^1$H NMR (400 MHz, DMSO-d$_6$) δ (ppm): 13.25 (brs, 1H), 8.20 (s, 1H), 5.50-5.44 (q, J=7.6 Hz, 1H), 3.44 (s, 3H), 3.24 (s, 3H), 1.76-1.74 (d, J=7.6 Hz, 3H). LC-MS: m/z 226.14 (M+H) with a purity of 95%.

Step 3: (S)-2-(1,3-dimethyl-2,6-dioxo-2,3-dihydro-1H-purin-7(6H)-yl)-N-(4-(thiophen-3-yl) phenyl) propanamide The final product was prepared using amide coupling method A reaction conditions as described.

$^1$H NMR (400 MHz, DMSO-d$_6$) δ (ppm): 10.47 (s, 1H), 8.33 (s, 1H), 7.79 (s, 1H), 7.69-7.67 (d, J=8.8 Hz, 2H), 7.62-7.60 (d, J=8.4 Hz, 3H), 7.53-7.52 (d, J=4.8 Hz, 1H), 5.71-5.69 (q, J=6.9 Hz, 1H), 3.46 (s, 3H), 3.20 (s, 3H), 1.84-1.83 (d, J=6.8 Hz, 2H). LC-MS: m/z 410.07 (M+H) with a purity of 99%. ee: 99.67%.

Compound 60: (S)-2-(1,3-dimethyl-2,6-dioxo-2,3-dihydro-1H-purin-7(6H)-yl)-N-(4-(thiophen-3-yl)phenyl)propanamide

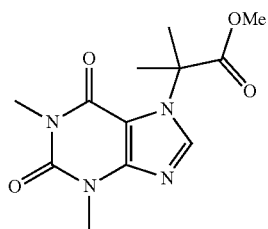 [SMILES: COC(=O)C(C)(C)n1cnc2c1c(=O)n(C)c(=O)n2C]

Step 1: Preparation of methyl 2-(1,3-dimethyl-2,6-dioxo-2,3-dihydro-1H-purin-7(6H)-yl)-2-methylpropanoate Intermediate was prepared using alkylation method A conditions as described. $^1$H-NMR (400 MHz; DMSO-d$_6$) δ (ppm): 8.24 (s, 1H), 3.62 (s, 3H), 3.44 (s, 3H), 3.19 (s, 3H), 1.80 (s, 6H). MS (ESI): m/z 281 [M+H]+. LC-MS: Purity of 34%.

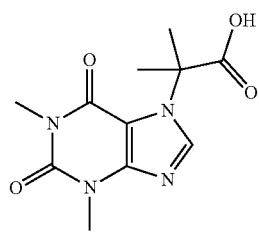 [SMILES: Cn1c(=O)c2c(ncn2C(C)(C)C(=O)O)n(C)c1=O]

Step 2: Preparation of 2-(1,3-dimethyl-2,6-dioxo-2,3-dihydro-1H-purin-7(6H)-yl)-2-methyl propanoic acid Intermediate was prepared using hydrolysis conditions as described. $^1$H-NMR (400 MHz; DMSO-d$_6$) δ (ppm): 13.10 (brs, 1H), 8.22 (s, 1H), 3.45 (s, 3H), 3.21 (s, 3H), 1.81 (s, 6H). MS (ESI): m/z 267 [M+H]+. LC-MS: Purity of 87%.

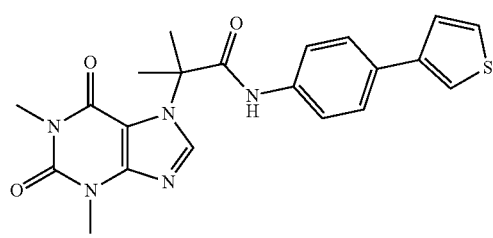 [SMILES: Cn1c(=O)c2c(ncn2C(C)(C)C(=O)Nc2ccc(-c3ccsc3)cc2)n(C)c1=O]

Step 3: Preparation of 2-(1,3-dimethyl-2,6-dioxo-2,3-dihydro-1H-purin-7(6H)-yl)-2-methyl-N-(4-(thiophen-3-yl)phenyl)propanamide The final product was prepared using amide coupling method A reaction conditions as described. $^1$H-NMR (400 MHz; DMSO-d$_6$) δ (ppm): 9.37 (s, 1H), 8.28 (s, 1H), 7.78 (s, 1H), 7.65-7.60 (m, 3H), 7.60-7.52 (m, 3H), 3.47 (s, 3H), 3.17 (s, 3H), 1.90 (s, 6H). MS (ESI): m/z 424.05 [M+H]+. LC-MS: Purity of 96%.

Compound 61: 2-(1,3-dimethyl-2,6-dioxo-2,3-dihydro-1H-purin-7(6H)-yl)-N-(4-(thiophen-3-yl) phenyl)propanamide

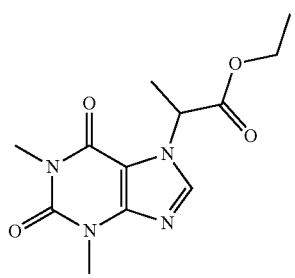 [SMILES: CCOC(=O)C(C)n1cnc2c1c(=O)n(C)c(=O)n2C]

Step 1: Preparation ethyl 2-(1,3-dimethyl-2,6-dioxo-2,3-dihydro-1H-purin-7(6H)-yl) propanoate Intermediate was prepared using alkylation method A conditions as described. $^1$H NMR (400 MHz, CDCl$_3$) δ (ppm): 7.97 (s, 1H), 5.59 (q, J=7.60 Hz, 1H), 4.24 (q, J=7.20 Hz, 2H), 3.58 (s, 3H), 3.36 (s, 3H), 1.83 (d, J=7.60 Hz, 3H), 1.28 (t, J=7.20 Hz, 3H). LC-MS: m/z 281 (M+H).

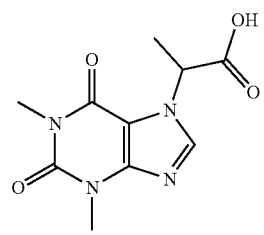

Step 2: Preparation 2-(1,3-dimethyl-2,6-dioxo-2,3-dihydro-1H-purin-7(6H)-yl)propanoic acid Intermediate was prepared using hydrolysis conditions as described. $^1$H NMR (400 MHz, DMSO-d$_6$) δ (ppm): 8.19 (s, 1H), 5.46 (q, J=7.20 Hz, 1H), 3.44 (s, 3H), 3.21 (s, 3H), 1.74 (d, J=7.20 Hz, 3H). LC-MS: m/z 253 (M+H).

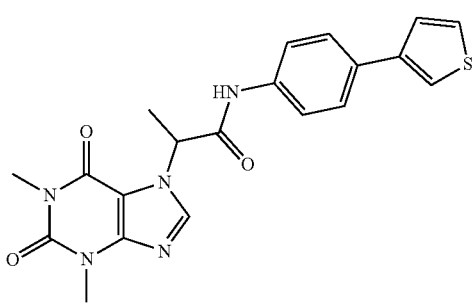 [SMILES: CC(C(=O)Nc1ccc(-c2ccsc2)cc1)n1cnc2c1c(=O)n(C)c(=O)n2C]

Step 3: Preparation 2-(1,3-dimethyl-2,6-dioxo-2,3-dihydro-1H-purin-7(6H)-yl)-N-(4-(thiophen-3-yl)phenyl)propanamide The final product was prepared using amide coupling method D reaction conditions as described.

$^1$H NMR (400 MHz, DMSO-d$_6$) δ (ppm): 10.46 (s, 1H), 8.31 (s, 1H), 7.78 (d, J=1.60 Hz, 1H), 7.60-7.68 (m, 5H), 7.52 (d, J=4.80 Hz, 1H), 5.69 (q, J=7.20 Hz, 1H), 3.45 (s, 3H), 3.20 (s, 3H), 1.83 (d, J=7.20 Hz, 1H). LC-MS: m/z 410 (M+H) with a purity of 97%.

Compound 62: N-(biphenyl-4-yl)-2-(1,3-dimethyl-2,6-dioxo-2,3-dihydro-1H-purin-7(6H)-yl)propanamide

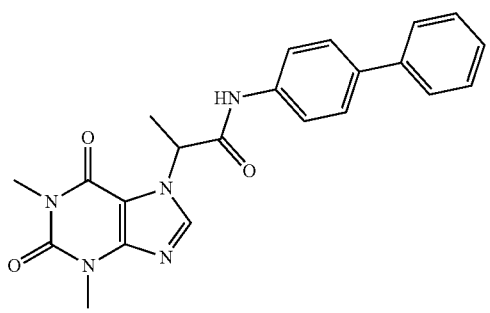 [SMILES: CC(C(=O)Nc1ccc(-c2ccccc2)cc1)n1cnc2c1c(=O)n(C)c(=O)n2C]

The final product was prepared using amide coupling method D reaction conditions as described. NMR (400 MHz, DMSO-d$_6$) δ (ppm): 10.49 (s, 1H), 8.32 (s, 1H), 7.62-7.68 (m, 6H), 7.43 (t, J=7.60 Hz, 2H), 7.32 (t, J=7.60 Hz, 1H), 5.70 (q, J=7.20 Hz, 1H), 3.46 (s, 3H), 3.20 (s, 3H), 1.84 (d, J=7.20 Hz, 3H). LC-MS: m/z 404 (M+H) with a purity of 99%.

Compound 63: N-(4-(4-(3,5-difluorobenzyl)piperazin-1-yl)phenyl)-2-(1,3-dimethyl-2,6-dioxo-2,3-dihydro-1H-purin-7(6H)-yl)propanamide

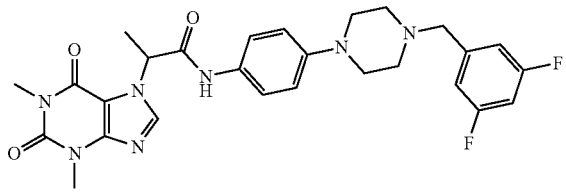 [SMILES: CC(C(=O)Nc1ccc(N2CCN(Cc3cc(F)cc(F)c3)CC2)cc1)n1cnc2c1c(=O)n(C)c(=O)n2C]

Product was prepared using alkylation method A reaction conditions as described. $^1$H NMR (600 MHz, CDCl$_3$) δ (ppm): 9.25 (s, 1H), 7.86 (s, 1H), 7.42 (d, J=9.1 Hz, 2H), 6.92 (d, J=6.3 Hz, 2H), 6.85 (d, J=9.1 Hz, 2H), 6.70 (m, 1H), 5.55 (q, J=7.1 Hz, 1H), 3.60 (s, 3H), 3.56 (s, 2H), 3.46 (s, 3H), 3.17 (m, 4H), 2.62 (m, 4H), 1.87 (d, J=7.1 Hz, 3H). LC-MS: m/z 538 (M+1) with HPLC purity of 99%.

Compound 64: 2-(1,3-dimethyl-2,6-dioxo-2,3-dihydro-1H-purin-7(6H)-yl)-N-(4-(thiophen-3-yl)phenyl)butanamide

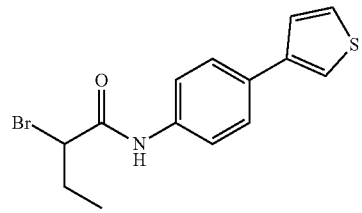 [SMILES: CCC(Br)C(=O)Nc1ccc(-c2ccsc2)cc1]

Step 1: Preparation 2-bromo-N-(4-(thiophen-3-yl)phenyl)butanamide

Intermediate was prepared using amide coupling method E reaction conditions as described. $^1$H NMR (400 MHz, CDCl$_3$) δ (ppm): 7.58-7.59 (m, 4H), 7.42 (s, 1H), 7.36-7.40 (m, 2H), 4.43-4.48 (m, 1H), 2.22-2.31 (m, 1H), 2.07-2.20 (m, 1H), 1.10-1.14 (m, 3H).

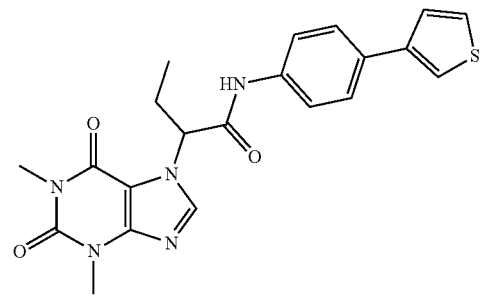 [SMILES: CCC(C(=O)Nc1ccc(-c2ccsc2)cc1)n1cnc2c1c(=O)n(C)c(=O)n2C]

Step 2: Preparation 2-(1,3-dimethyl-2,6-dioxo-2,3-dihydro-1H-purin-7(6H)-yl)-N-(4-(thiophen-3-yl)phenyl)butanamide Final product was prepared using the alkylation method B reaction conditions as described. $^1$H NMR (400 MHz, MeOD-d$_4$) δ (ppm): 8.26 (s, 1H), 7.61 (s, 4H), 7.56-7.57 (m, 1H), 7.42-7.46 (m, 2H), 5.67-5.71 (m, 1H), 3.56 (s, 3H), 3.36 (s, 3H), 2.23-2.38 (m, 2H), 1.04-1.07 (m, 3H). LC-MS: m/z 424 (M+H) with a purity of 97%.

Compound 65: N-(biphenyl-4-yl)-2-(1,3-dimethyl-2,6-dioxo-2,3-dihydro-1H-purin-7(6H)-yl)-3-methylbutanamide

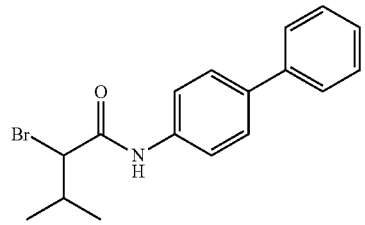 [SMILES: CC(C)C(Br)C(=O)Nc1ccc(-c2ccccc2)cc1]

Step 1: Preparation N-(biphenyl-4-yl)-2-bromo-3-methylbutanamide

Intermediate was prepared using amide coupling method B reaction conditions as described. $^1$H NMR (400 MHz, DMSO-$d_6$) δ (ppm): 10.40 (s, 1H), 7.63-7.70 (m, 6H), 7.42-7.46 (m, 2H), 7.31-7.35 (m, 1H), 4.30-4.33 (m, 1H), 2.19-2.28 (m, 1H), 1.11 (d, J=6.80 Hz, 3H), 0.99 (d, J=6.80 Hz, 3H). LC-MS: m/z 404 (M+H).

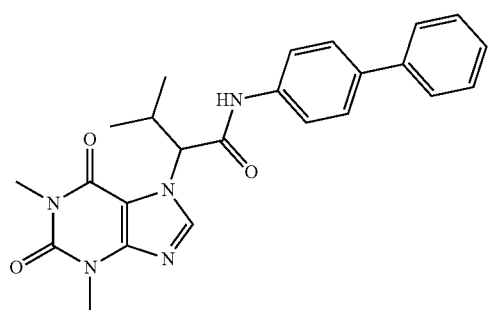 [SMILES: CC(C)C(C(=O)Nc1ccc(-c2ccccc2)cc1)n1cnc2c1c(=O)n(C)c(=O)n2C]

Step 2: Preparation N-(biphenyl-4-yl)-2-(1,3-dimethyl-2,6-dioxo-2,3-dihydro-1H-purin-7(6H)-yl)-3-methylbutanamide The product was prepared using alkylation method A reaction conditions as described. $^1$H NMR (400 MHz, MeOD-$d_4$) δ (ppm): 8.36 (s, 1H), 7.66-7.69 (m, 2H), 7.58-7.60 (m, 4H), 7.41 (t, J=7.60 Hz, 2H), 7.30 (t, J=7.60 Hz, 1H), 5.52-5.54 (m, 1H), 3.56 (s, 3H), 3.38 (s, 3H), 2.57-2.67 (m, 1H), 1.16 (d, J=6.80 Hz, 3H), 0.96 (d, J=6.80 Hz, 3H). LC-MS: m/z 432 (M+H) with a purity of 99%.

Preparation of 1,3,8-trimethyl-1H-purine-2,6(3H,7H)-dione

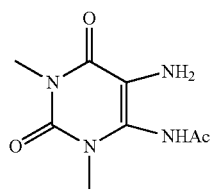

Step 1: Preparation of N-(5-amino-1,3-dimethyl-2,6-dioxo-1,2,3,6-tetrahydropyrimidin-4-yl)acetamide To a stirred solution of commercially available 5,6-diamino-1,3-dimethylpyrimidine-2,4(1H,3H)-dione, 1 (1 equiv.) in acetic acid (4 equiv.) at room temperature and warmed to 70° C. for 4 h. The reaction mixture was cooled to room temperature then diluted with ice water and concentrated under reduced pressure to get crude compound, dried under vacuum. The resultant crude was precipitated with 20% dichloromethane in hexane to afford N-(5-amino-1,3-dimethyl-2,6-dioxo-1,2,3,6-tetrahydropyrimidin-4-yl)acetamide as a yellow solid. $^1$H-NMR (400 MHz; DMSO-$d_6$) δ (ppm): 8.36 (s, 1H), 6.58 (s, 2H), 3.30 (s, 3H), 3.10 (s, 3H), 1.92 (s, 3H). MS (ESI): m/z 213 [M+H]+. LC-MS: Purity of 96%.

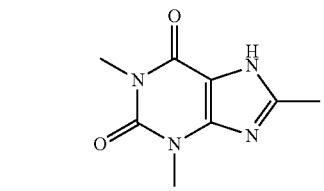

Step 2: Preparation of 1,3,8-trimethyl-1H-purine-2,6(3H,7H)-dione

To a stirred solid of N-(5-amino-1,3-dimethyl-2,6-dioxo-1,2,3,6-tetrahydropyrimidin-4-yl)acetamide, 2 at room temperature and warmed to 250° C. for 2 h. The reaction mixture was cooled to room temperature and the reaction mixture was precipitated with 30% dichloromethane in hexane to afford 1,3,8-trimethyl-1H-purine-2,6(3H,7H)-dione as a yellow solid. $^1$H-NMR (400 MHz; DMSO-$d_6$) δ (ppm): 12.50 (brs, 1H), 3.40 (s, 3H), 3.22 (s, 3H), 2.37 (s, 3H). MS (ESI): m/z 195 [M+H]+. LC-MS: Purity of 96%.

Compound 66: N-(4-(thiophen-3-yl)phenyl)-2-(1,3,8-trimethyl-2,6-dioxo-2,3-dihydro-1H-purin-7(6H)-yl)acetamide

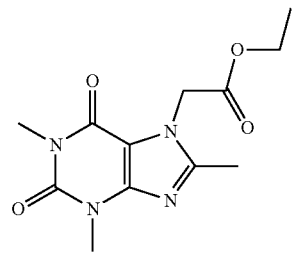 [SMILES: CCOC(=O)Cn1c(C)nc2c1c(=O)n(C)c(=O)n2C]

Step 1: Preparation of ethyl 2-(1,3,8-trimethyl-2,6-dioxo-2,3-dihydro-1H-purin-7(6H)-yl)acetate Intermediate was prepared using alkylation method A reaction conditions as described. $^1$H-NMR (400 MHz; CDCl$_3$) δ (ppm): 5.09 (s, 2H), 4.27 (q, J=7.2 Hz), 3.58 (s, 3H), 3.38 (s, 3H), 2.43 (s, 3H), 1.31 (t, J=7.2 Hz, 3H). MS (ESI): m/z 281 [M+H]+. LC-MS: Purity of 93%.

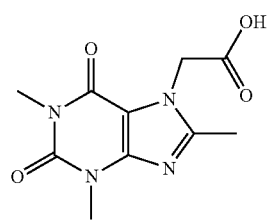 [SMILES: Cc1nc2c(c(=O)n(C)c(=O)n2C)n1CC(=O)O]

Step 2: Preparation of 2-(1,3,8-trimethyl-2,6-dioxo-2,3-dihydro-1H-purin-7(6H)-yl)acetic acid Intermediate was prepared using hydrolysis reaction conditions as described. $^1$H-NMR (400 MHz; DMSO-$d_6$) δ

(ppm): 13.34 (brs, 1H), 5.08 (s, 2H), 3.41 (s, 3H), 3.20 (s, 3H), 2.38 (s, 3H). MS (ESI): m/z 251 [M−H]−. LC-MS: Purity of 94%.

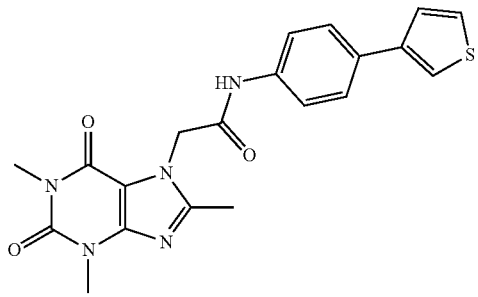

Step 3: Preparation of N-(4-(thiophen-3-yl)phenyl)-2-(1,3,8-trimethyl-2,6-dioxo-2,3-dihydro-1H-purin-7(6H)-yl)acetamide Product was prepared using amide coupling method A reaction conditions as described. $^1$H-NMR (400 MHz; DMSO-d$_6$) δ (ppm): 10.50 (s, 1H), 7.80 (s, 1H), 7.70-7.61 (m, 5H), 7.53 (d, J=4.4 Hz, 1H), 5.22 (s, 2H), 3.44 (s, 3H), 3.20 (s, 3H), 2.42 (s, 3H). MS (ESI): m/z 408.5 [M−H]−. LC-MS: Purity of 96%.

Compound 67: (S)—N-(4-(thiazol-2-yl) phenyl)-2-(1,3,8-trimethyl-2,6-dioxo-2,3-dihydro-1H-purin-7(6H)-yl)propanamide

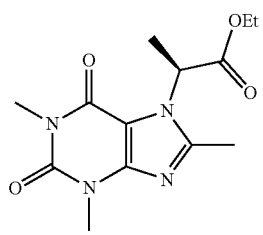 [SMILES: CCOC(=O)[C@H](C)n1c(C)nc2c1c(=O)n(C)c(=O)n2C]

Step 1: Preparation of (S)-ethyl 2-(1,3,8-trimethyl-2,6-dioxo-2,3-dihydro-1H-purin-7(6H)-yl)propanoate.

Intermediate was prepared using Mitsunobu reaction conditions as described. $^1$H-NMR (400 MHz; CDCl$_3$) δ (ppm): 5.50 (q, J=7.2 Hz, 1H), 4.11 (q, J=3.6 Hz, 2H), 3.41 (s, 3H), 3.19 (s, 3H), 2.46 (s, 3H), 1.66 (d, J=7.2 Hz, 3H), 1.14 (t, J=7.2 Hz, 3H). LC-MS: m/z 295.1 (M+H) with a purity of 57.79% (desired). LCMS: m/z 279 (M+H) with a purity of 31%.

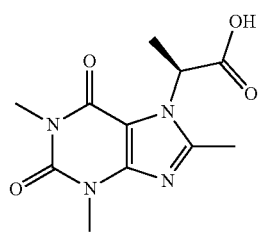

Step 2: Preparation of (S)-2-(1,3,8-trimethyl-2,6-dioxo-2,3-dihydro-1H-purin-7(6H)-yl) propanoic acid Intermediate was prepared using hydrolysis reaction conditions as described. $^1$H-NMR (400 MHz; DMSO-d$_6$) δ (ppm): 13.03 (brs, 1H), 5.43 (q, J=6.8 Hz, 1H), 3.41 (s, 3H), 3.20 (s, 3H), 2.45 (s, 3H), 1.66 (d, J=7.2 Hz, 3H). LC-MS: m/z 267.1 [M+H]+. LC-MS: Purity of 98%.

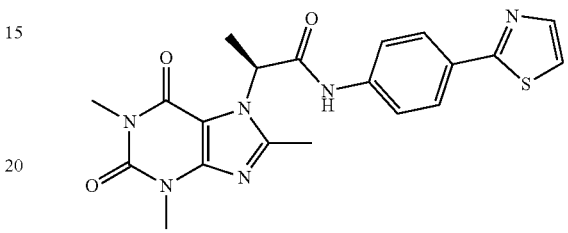

Step 3: Preparation of (S)—N-(4-(thiazol-2-yl) phenyl)-2-(1,3,8-trimethyl-2,6-dioxo-2,3-dihydro-1H-purin-7(6H)-yl)propanamide Product was prepared using amide coupling method A reaction conditions as described. $^1$H-NMR (400 MHz; DMSO-d$_6$) δ (ppm): 9.99 (s, 1H), 7.89-7.82 (m, 3H), 7.71-7.65 (m, 3H), 5.74 (q, J=6.9 Hz, 1H), 3.46 (s, 3H), 3.33 (s, 3H), 3.19 (s, 3H), 1.77 (d, J=7.2 Hz, 3H). LC-MS: m/z 422.9 [M−H]− (95%) and 90% ee.

Preparation of ethyl 2-(8-bromo-1,3-dimethyl-2,6-dioxo-2,3-dihydro-1H-purin-7(6H)-yl) acetate

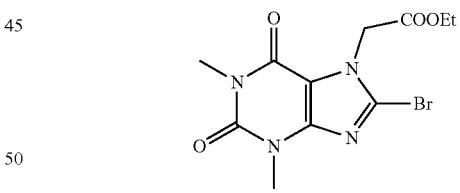

To a solution of commercially available 8-bromo-1,3-dimethyl-1H-purine-2,6(3H,7H)-dione (1 equiv.) in N,N-dimethylformamide (0.2 M) was added bromoethylacetate (1.2 equiv.), K$_2$CO$_3$ (2.5 equiv.) at room temperature and warmed to 70° C. for 4 h. The reaction mixture was cooled to room temperature then poured into ice water to precipitate the crude compound. The solid was filtered and washed with water, dried under vacuum. The resultant solid was re-crystallized with isopropanol to afford the product. $^1$H-NMR (400 MHz; CDCl$_3$) δ (ppm): 5.12 (s, 2H), 4.28 (q, J=7.6 Hz, 2H), 3.58 (s, 3H), 3.38 (s, 3H), 1.32 (t, J=6.8 Hz, 3H). MS (ESI): m/z 331 [M+H]+.

Compound 68: N-(4-(thiophen-3-yl)phenyl)-2-(1,3,8-trimethyl-2,6-dioxo-2,3-dihydro-1H-purin-7(6H)-yl)acetamide

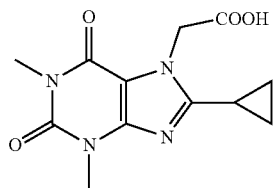 [SMILES: Cn1c(=O)c2c(nc(C3CC3)n2CC(=O)O)n(C)c1=O]

Step 1: Preparation of 2-(8-cyclopropyl-1,3-dimethyl-2,6-dioxo-2,3-dihydro-1H-purin-7(6H)-yl) acetic acid Intermediate was prepared using Suzuki Method C reaction conditions as described. $^1$H-NMR (400 MHz; DMSO-$d_6$) δ (ppm): 13.30 (brs, 1H), 5.20 (s, 2H), 3.37 (s, 3H), 3.19 (s, 3H), 2.15-2.12 (m, 1H), 1.05 (d, J=2.8 Hz, 2H), 0.98 (d, J=2.8 Hz, 2H). MS (ESI): m/z 279 [M+H]+. LC-MS: Purity of 88%.

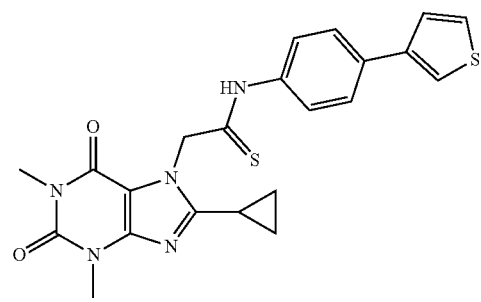 [SMILES: Cn1c(=O)c2c(nc(C3CC3)n2CC(=S)Nc2ccc(-c3ccsc3)cc2)n(C)c1=O]

Step 2: Preparation of 2-(8-cyclopropyl-1,3-dimethyl-2,6-dioxo-2,3-dihydro-1H-purin-7(6H)-yl)-N-(4-(thiophen-3-yl)phenyl)acetamide Product was prepared using amide coupling reaction conditions as described. $^1$H-NMR (400 MHz; DMSO-$d_6$) δ (ppm): 10.46 (s, 1H), 7.78 (s, 1H), 7.69-7.52 (m, 5H), 7.52 (d, J=4.4 Hz, 1H), 5.32 (s, 2H), 3.39 (s, 3H), 3.19 (s, 3H), 2.15 (m, 1H), 1.06-1.02 (m, 4H). MS (ESI): m/z 436 [M+H]+. LC-MS: Purity of 94%.

Compound 69: N-(4-(thiophen-3-yl)phenyl)-2-(1,3,8-trimethyl-2,6-dioxo-2,3-dihydro-1H-purin-7(6H)-yl)acetamide

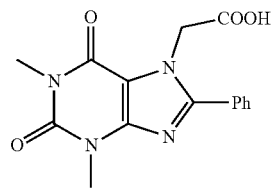 [SMILES: Cn1c(=O)c2c(nc(-c3ccccc3)n2CC(=O)O)n(C)c1=O]

Step 1: Preparation of 2-(1,3-dimethyl-2,6-dioxo-8-phenyl-2,3-dihydro-1H-purin-7(6H)-yl) acetic acid Intermediate was prepared using Suzuki Method C reaction conditions as described. $^1$H-NMR (400 MHz; DMSO-$d_6$) δ (ppm): 13.38 (brs, 1H), 7.67-7.57 (m, 5H), 5.01 (s, 2H), 3.49 (s, 3H), 3.25 (s, 3H). MS (ESI): m/z 315 [M+H]+. LC-MS: Purity of 94%.

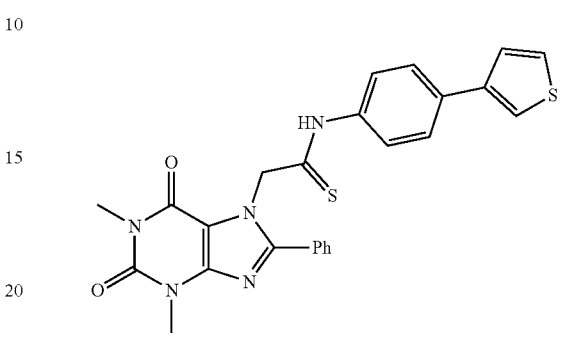

Step 2: Preparation of 2-(1,3-dimethyl-2,6-dioxo-8-phenyl-2,3-dihydro-1H-purin-7(6H)-yl)-N-(4-(thiophen-3-yl)phenyl)acetamide Product was prepared using amide coupling reaction conditions as described. $^1$H-NMR (400 MHz; DMSO-$d_6$) δ (ppm): 10.53 (s, 1H), 7.80 (s, 1H), 7.72-7.67 (m, 5H), 7.61-7.53 (m, 6H), 5.21 (s, 2H), 3.51 (s, 3H), 3.24 (s, 3H). MS (ESI): m/z 472 [M+H]+. LC-MS: Purity of 98%.

Compound 70: 2-(1,3-dimethyl-2,6-dioxo-8-(trifluoromethyl)-2,3-dihydro-1H-purin-7(6H)-yl)-N-(4-(thiophen-3-yl)phenyl)acetamide

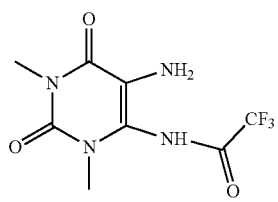 [SMILES: Cn1c(NC(=O)C(F)(F)F)c(N)c(=O)n(C)c1=O]

Step 1: Preparation of N-(5-amino-1,3-dimethyl-2,6-dioxo-1,2,3,6-tetrahydropyrimidin-4-yl)-2,2,2-trifluoroacetamide To a stirred solution of commercially available 5,6-diamino-1,3-dimethylpyrimidine-2,4(1H,3H)-dione (1 equiv.) in benzene (0.06 M) at room temperature was added trifluoroacetic acid (1 equiv.) and the resulting reaction mixture was heated to reflux for 4 h. After completion of the starting material, the reaction mixture was cooled to room temperature and concentrated under vacuum. The residue was washed with diethyl ether and dried to give the intermediate N-(5-amino-1,3-dimethyl-2,6-dioxo-1,2,3,6-tetrahydropyrimidin-4-yl)-2,2,-tri fluoroacetamide as a brown solid. $^1$H NMR (400 MHz, DMSO-$d_6$) δ (ppm): 9.76 (s, 1H), 6.97 (s, 2H), 3.32 (s, 3H), 3.11 (s, 3H). LC-MS: m/z 264.9 (M–H) with a purity of 84%.

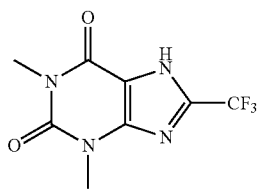 [SMILES: Cn1c(=O)c2[nH]c(C(F)(F)F)nc2n(C)c1=O]

Step 2: Preparation of 1,3-dimethyl-8-(trifluoromethyl)-1H-purine-2,6(3H,7H)-dione N-(5-amino-1,3-dimethyl-2,6-dioxo-1,2,3,6-tetrahydropyrimidin-4-yl)-2,2,2-trifluoroacetamide was mixed with P$_2$O$_5$ (w/w) and heated to 200° C. for 15 h. The black mass was cooled to room temperature and quenched with ice and extracted with ethyl acetate twice. The combined ethyl acetate layers were dried over Na$_2$SO$_4$ and concentrated under vacuum. The crude compound was purified by column chromatography to afford the intermediate 1,3-dimethyl-8-(trifluoromethyl)-1H-purine-2,6(3H,7H)-dione as a light brown solid. $^1$H NMR (400 MHz, DMSO-d$_6$) δ (ppm): 3.34 (s, 3H), 3.26 (brs, 1H), 3.24 (s, 3H). LC-MS: m/z 249.0 (M+H) with a purity of 88%.

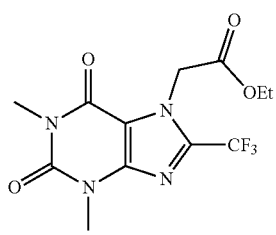 [SMILES: CCOC(=O)Cn1c(C(F)(F)F)nc2c1c(=O)n(C)c(=O)n2C]

Step 3: Preparation of ethyl 2-(1,3-dimethyl-2,6-dioxo-8-(trifluoromethyl)-2,3-dihydro-1H-purin-7(6H)-yl)acetate Intermediate was prepared using alkylation method A reaction conditions as described. $^1$H NMR (400 MHz, CDCl$_3$) δ (ppm): 5.28 (s, 2H), 4.31-4.25 (q, J=7.2 Hz, 2H), 3.61 (s, 3H), 3.40 (s, 3H), 1.29-1.21 (t, J=7.2 Hz, 3H).

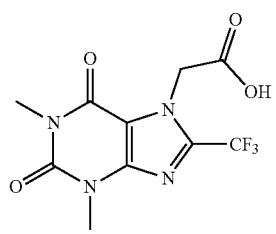 [SMILES: Cn1c(=O)c2c(nc(C(F)(F)F)n2CC(=O)O)n(C)c1=O]

Step 4: Preparation of 2-(1,3-dimethyl-2,6-dioxo-8-(trifluoromethyl)-2,3-dihydro-1H-purin-7(6H)-yl) acetic acid Intermediate was prepared using hydrolysis reaction conditions as described. LC-MS: m/z 307.3 (M+H) with a purity of 41%.

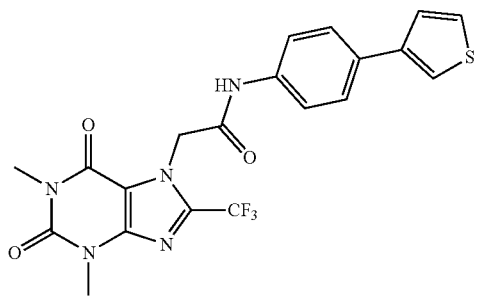

Step 5: Preparation of 2-(1,3-dimethyl-2,6-dioxo-8-(trifluoromethyl)-2,3-dihydro-1H-purin-7(6H)-yl)-N-(4-(thiophen-3-yl)phenyl)acetamide Product was prepared using amide coupling method A reaction conditions as described. $^1$H NMR (400 MHz, DMSO-d$_6$) δ (ppm): 10.57 (s, 1H), 7.79-7.70 (m, 1H), 7.68-7.66 (d, J=8.4 Hz, 2H), 7.61-7.55 (m, 3H), 7.52-7.50 (dd, J1=3.2 Hz, J2=1.6 Hz, 1H), 5.43 (s, 2H), 3.45 (s, 3H), 3.22 (s, 3H). LC-MS: m/z 464.02 (M+H) with a purity of 97%.

Compound 71: 2-(2,6-dioxo-2,3-dihydro-1H-purin-7(6H)-yl)-N-(4-(thiophen-3-yl)phenyl) acetamide

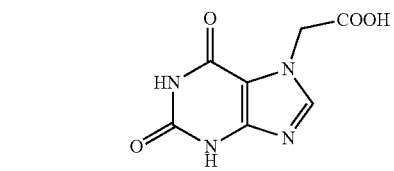 [SMILES: O=C(O)Cn1cnc2[nH]c(=O)[nH]c(=O)c21]

Step 1: Preparation of 2-(2,6-dioxo-2,3-dihydro-1H-purin-7(6H)-yl)acetic acid Commercially available 1H-purine-2,6(3H,7H)-dione (1 equiv.) in water (1.5 M) at room temperature was added 2M NaOH solution (0.65 M) and the resulting solution was stirred for 30 min and chloroacetic acid (1 equiv.) was added and resulting reaction mixture was refluxed for 5 h. The reaction mixture was cooled to room temperature and stirred for 16 h. The precipitated solid was removed by filtration and water was acidified with conc HCl (pH 2). The solid collected by filtration, washed with hot ethanol to afford the intermediate 2-(2,6-dioxo-2,3-dihydro-1H-purin-7(6H)-yl) acetic acid as a white solid. $^1$H NMR (400 MHz, DMSO-d$_6$) δ (ppm): 13.35 (brs, 1H), 11.59 (s, 1H), 10.88 (brs, 1H), 7.91 (s, 1H), 5.0 (s, 2H). LC-MS: m/z 211.1 (M+H) with a purity of 97%.

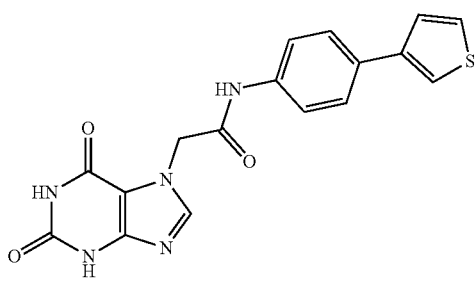 [SMILES: O=C(Cn1cnc2[nH]c(=O)[nH]c(=O)c21)Nc1ccc(-c2ccsc2)cc1]

Step 2: Preparation of 2-(2,6-dioxo-2,3-dihydro-1H-purin-7(6H)-yl)-N-(4-(thiophen-3-yl) phenyl)acetamide Product was prepared using amide coupling method D reaction conditions as described. ¹H NMR (400 MHz, DMSO-d₆) δ (ppm): 11.60 (s, 1H), 10.88 (brs, 1H), 10.43 (brs, 1H), 7.95 (s, 1H), 7.80-7.79 (d, J=2 Hz, 1H), 7.70-7.67 (d, J=8.8 Hz, 2H), 7.61-7.59 (m, 3H), 7.53-7.52 (d, J=4.8 Hz, 1H), 5.14 (s, 2H). LC-MS: mlz 366.10 (M−H) with a purity of 95.43%. HPLC: At 278 nm with a purity of 96%.

Compound 72: 2-(1,3-diethyl-2,6-dioxo-2,3-dihydro-1H-purin-7(6H)-yl)-N-(4-(thiophen-3-yl) phenyl)acetamide

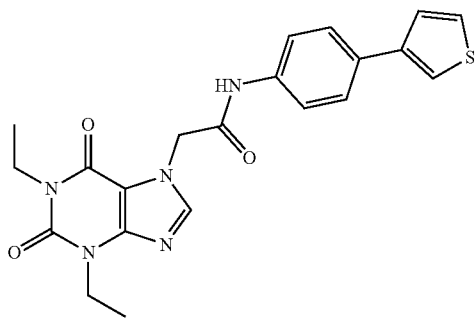 [SMILES: CCn1c(=O)c2c(ncn2CC(=O)Nc2ccc(-c3ccsc3)cc2)n(CC)c1=O]

Step 3: Preparation of 2-(1,3-diethyl-2,6-dioxo-2,3-dihydro-1H-purin-7(6H)-yl)-N-(4-(thiophen-3-yl) phenyl)acetamide A stirred solution of 2-(2,6-dioxo-2,3-dihydro-1H-purin-7(6H)-yl)-N-(4-(thiophen-3-yl)phenyl)acetamide (1 equiv.)) in N,N-dimethylformamide (0.03 M) was added K₂CO₃ (2.5 equiv.) and stirred at room temperature for 15 min. Ethyl iodide (2.5 equiv.) was added to the reaction mixture and stirred for another 4 h at room temperature. After completion, water was added to the reaction mixture and extracted with ethyl acetate twice. The combined organic layer was washed with brine, dried over anhydrous Na₂SO₄, and concentrated under vacuum and purified by column chromatography to afford the product 2-(1,3-diethyl-2,6-dioxo-2,3-dihydro-1H-purin-7(6H)-yl)-N-(4-(thiophen-3-yl)phenyl)acetamide as an off-white solid. ¹H NMR (400 MHz, DMSO-d₆) δ (ppm): 10.48 (s, 1H), 8.08 (s, 1H), 7.70-7.68 (d, J=8.4 Hz, 2H), 7.62-7.61 (m, 3H), 7.54-7.53 (d, J=4.4 Hz, 1H), 5.21 (s, 2H), 4.06-4.04 (m, 2H), 3.89-3.87 (m, 2H), 1.27-1.23 (t, J=6.8 Hz, 3H), 1.11-1.08 (t, J=6.8 Hz, 3H). LC-MS: m/z 424.12 (M+H) with a purity of 99%.

Compound 73: 2-(8-(dimethylamino)-1,3-dimethyl-2,6-dioxo-2,3-dihydro-1H-purin-7(6H)-yl)-N-(4-(thiophen-3-yl)phenyl)acetamide

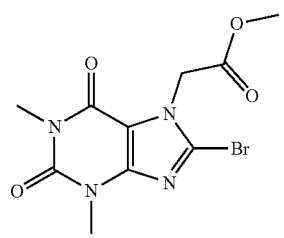 [SMILES: COC(=O)Cn1c(Br)nc2c1c(=O)n(C)c(=O)n2C]

Step 1: Preparation of 2-(1,3-dimethyl-2,6-dioxo-2,3-dihydro-1H-purin-7(6H)-yl)-N-(3'-methoxybiphenyl-4-yl)acetamide Intermediate was prepared using alkylation method A reaction conditions as described. ¹H NMR (400 MHz, DMSO-d₆) δ (ppm): 5.19 (s, 2H), 3.74 (s, 3H), 3.41 (s, 3H), 3.20 (s, 3H). LC-MS: m/z 332 (M+H).

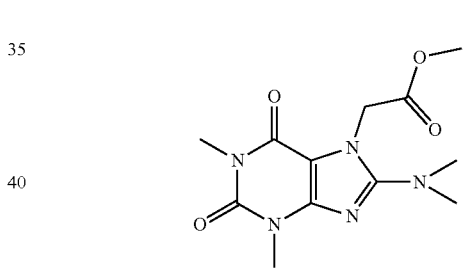

Step 2: Preparation of methyl 2-(8-(dimethylamino)-1,3-dimethyl-2,6-dioxo-2,3-dihydro-1H-purin-7(6H)-yl)acetate A solution of 2-(1,3-dimethyl-2,6-dioxo-2,3-dihydro-1H-purin-7(6H)-yl)-N-(3'-methoxy biphenyl-4-yl)acetamide (1 equiv.) in 11% dimethylamine in 2M ethanol solution (1 equiv.) was refluxed for 18 h. After consumption of starting material, the reaction mixture was concentrated in vacuo and extracted with dichloromethane twice. The combined organic layers were washed with brine, dried over Na₂SO₄ and concentrated under vacuum. The crude compound was purified by column chromatography to obtain the intermediate methyl 2-(8-(dimethylamino)-1,3-dimethyl-2,6-dioxo-2,3-dihydro-1H-purin-7(6H)-yl)acetate. ¹H NMR (400 MHz, DMSO-d₆) δ (ppm): 5.00-4.98 (m, 2H), 3.71 (s, 3H), 3.38 (s, 3H), 3.16 (s, 3H), 2.93 (s, 6H). LC-MS: m/z 297 (M+H+41).

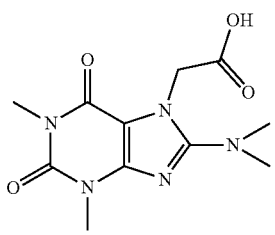 [SMILES: CN(C)c1nc2c(c(=O)n(C)c(=O)n2C)n1CC(=O)O]

Step 3: Preparation of 2-(8-(dimethylamino)-1,3-dimethyl-2,6-dioxo-2,3-dihydro-1H-purin-7(6H)-yl) acetic acid Intermediate was prepared using hydrolysis reaction conditions as described. LC-MS: m/z 282 (M+H).

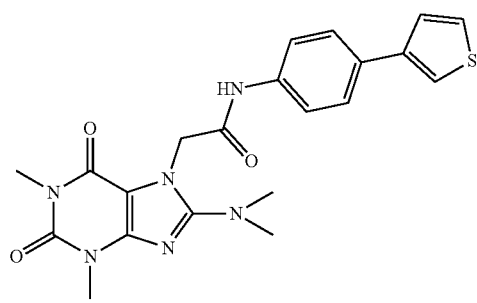 [SMILES: CN(C)c1nc2c(c(=O)n(C)c(=O)n2C)n1CC(=O)Nc1ccc(-c2ccsc2)cc1]

Step 4: Preparation of 2-(8-(dimethylamino)-1,3-dimethyl-2,6-dioxo-2,3-dihydro-1H-purin-7(6H)-yl)-N-(4-(thiophen-3-yl)phenyl)acetamide Product prepared using amide coupling method A reaction conditions as described. $^1$H NMR (400 MHz, DMSO-d$_6$) δ (ppm): 10.42 (s, 1H), 7.79-7.78 (m, 1H), 7.69 (s, 1H), 7.67 (s, 1H), 7.62-7.60 (m, 3H), 7.52 (dd, J=5 Hz, J=1 Hz, 1H), 5.02 (s, 2H), 3.41 (s, 3H), 3.17 (s, 3H), 2.97 (s, 6H). LC-MS: m/z 439 (M+H) with a purity of 97%.

Compound 74: 2-(1,3-dimethyl-8-morpholino-2,6-dioxo-2,3-dihydro-1H-purin-7(6H)-yl)-N-(4-(thiophen-3-yl)phenyl)acetamide

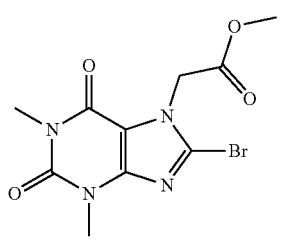 [SMILES: COC(=O)Cn1c(Br)nc2c1c(=O)n(C)c(=O)n2C]

Step 1: Preparation of methyl 2-(8-bromo-1,3-dimethyl-2,6-dioxo-2,3-dihydro-1H-purin-7(6H)-yl) acetate Intermediate was prepared using alkylation method A reaction conditions as described. $^1$H NMR (400 MHz, DMSO-d$_6$) δ (ppm): 5.19 (s, 2H), 3.74 (s, 3H), 3.41 (s, 3H), 3.20 (s, 3H). LC-MS: m/z 332 (M+H).

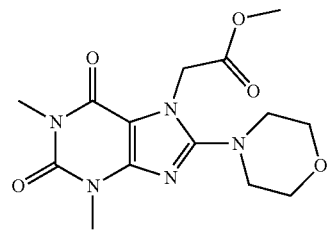 [SMILES: COC(=O)Cn1c(N2CCOCC2)nc2c1c(=O)n(C)c(=O)n2C]

Step 2: Preparation of methyl 2-(1,3-dimethyl-8-morpholino-2,6-dioxo-2,3-dihydro-1H-purin-7(6H)-yl)acetate A stirred solution of methyl 2-(8-bromo-1,3-dimethyl-2,6-dioxo-2,3-dihydro-1H-purin-7(6H)-yl)acetate (1 equiv.) and morpholine (5 equiv.) in DMF (0.4 M) was refluxed for 2 h. After consumption of starting material, the reaction mixture was quenched with water and extracted with dichloromethane twice. The combined organic layers were washed with brine, dried over Na$_2$SO$_4$ and concentrated under vacuum. The crude compound was purified by column chromatography to afford the intermediate methyl 2-(1,3-dimethyl-8-morpholino-2,6-dioxo-2,3-dihydro-1H-purin-7(6H)-yl)acetate. $^1$H NMR (400 MHz, DMSO-d$_6$) δ (ppm): 4.94 (s, 2H), 3.71-3.69 (m, 6H), 3.17 (s, 3H), 3.39 (s, 3H), 3.16-3.13 (m, 5H). LC-MS: m/z 338 (M+H).

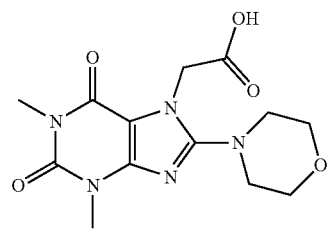 [SMILES: Cn1c(=O)c2c(nc(N3CCOCC3)n2CC(=O)O)n(C)c1=O]

Step 3: Preparation of 2-(1,3-dimethyl-8-morpholino-2,6-dioxo-2,3-dihydro-1H-purin-7(6H)-yl) acetic acid Intermediate was prepared using hydrolysis reaction conditions as described. $^1$H NMR (400 MHz, DMSO-d$_6$) δ (ppm): 4.83 (s, 2H), 3.72-3.70 (m, 3H), 3.39 (s, 3H), 3.18 (s, 3H), 3.16-3.14 (m, 5H). LC-MS: m/z 324 (M+H).

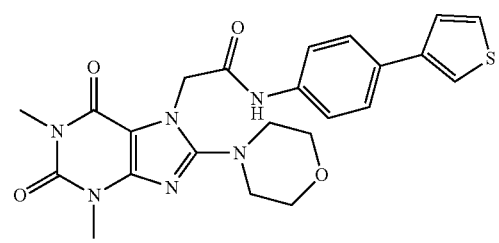 [SMILES: Cn1c(=O)c2c(nc(N3CCOCC3)n2CC(=O)Nc2ccc(-c3ccsc3)cc2)n(C)c1=O]

Step 4: Preparation of 2-(1,3-dimethyl-8-morpholino-2,6-dioxo-2,3-dihydro-1H-purin-7(6H)-yl)-N-(4-(thiophen-3-yl)phenyl)acetamide Product was prepared using amide coupling method A reaction conditions as described. $^1$H NMR (400 MHz, DMSO-d$_6$) δ (ppm): 10.45 (s, 1H), 7.79 (m, 1H), 7.69-7.67 (m, 2H), 7.63-7.60 (m, 3H), 7.52 (m, 1H), 4.97 (s, 2H), 3.70 (t, J=4.4 Hz, 4H), 3.42 (s, 3H), 3.21 (t, J=4.4 Hz, 4H), 3.19 (s, 3H). LC-MS: m/z 481 (M+H) with a purity of 99%.

Compound 75: 2-(1,3-dimethyl-2,6-dioxo-8-(thiophen-2-yl)-2,3-dihydro-1H-purin-7(6H)-yl)-N-(4-(thiophen-3-yl)phenyl)acetamide

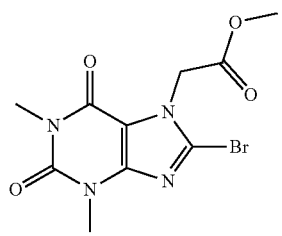 [SMILES: COC(=O)Cn1c(Br)nc2c1c(=O)n(C)c(=O)n2C]

Step 1: Preparation of methyl 2-(8-bromo-1,3-dimethyl-2,6-dioxo-2,3-dihydro-1H-purin-7(6H)-yl)acetate Intermediate prepared using alkylation method A reaction conditions as described. NMR (400 MHz, DMSO-d$_6$) δ (ppm): 5.19 (s, 2H), 3.74 (s, 3H), 3.41 (s, 3H), 3.20 (s, 3H). LC-MS: m/z 332 (M+H).

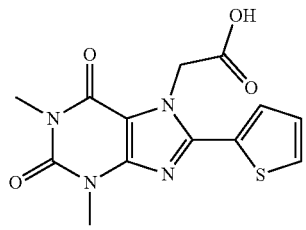 [SMILES: Cn1c(=O)c2c(nc(-c3cccs3)n2CC(=O)O)n(C)c1=O]

Step 2: Preparation of 2-(1,3-dimethyl-2,6-dioxo-8-(thiophen-2-yl)-2,3-dihydro-1H-purin-7(6H)-yl)acetic acid Intermediate prepared using Suzuki coupling method C reaction conditions as described. $^1$H NMR (400 MHz, DMSO-d$_6$) δ (ppm): 7.87-7.85 (m, 1H), 7.55-7.54 (m, 1H), 7.27-7.24 (m, 1H), 5.28 (s, 2H), 3.47 (s, 3H), 3.24 (s, 3H). LC-MS: m/z 321 (M+H).

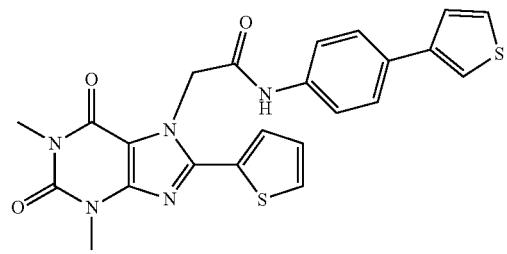 [SMILES: Cn1c(=O)c2c(nc(-c3cccs3)n2CC(=O)Nc2ccc(-c3ccsc3)cc2)n(C)c1=O]

Step 3: Preparation of 2-(1,3-dimethyl-2,6-dioxo-8-(thiophen-2-yl)-2,3-dihydro-1H-purin-7(6H)-yl)-N-(4-(thiophen-3-yl)phenyl)acetamide Product prepared using amide coupling method A reaction conditions as described. $^1$H NMR (400 MHz, DMSO-d$_6$) δ (ppm): 10.61 (s, 1H), 7.85 (dd, J=5.0 Hz, J=1.2 Hz, 1H), 7.80-7.79 (m, 1H), 7.70-7.68 (m, 2H), 7.62-7.59 (m, 4H), 7.54 (dd, J=15.8 Hz, J=1.2 Hz, 1H), 7.25-7.23 (m, 1H), 5.44 (s, 2H), 3.49 (s, 3H), 3.24 (s, 3H). LC-MS: m/z 478 (M+H) with a purity of 98%.

Compound 76: 2-(8-bromo-1,3-dimethyl-2,6-dioxo-2,3-dihydro-1H-purin-7(6H)-yl)-N-(4-(thiophen-3-yl)phenyl)acetamide

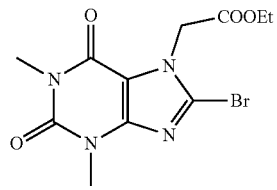 [SMILES: CCOC(=O)Cn1c(Br)nc2c1c(=O)n(C)c(=O)n2C]

Step 1: Methyl 2-(8-bromo-1,3-dimethyl-2,6-dioxo-2,3-dihydro-1H-purin-7(6H)-yl)acetate Intermediate prepared using alkylation method A reaction conditions as described. $^1$H NMR (400 MHz, DMSO-d$_6$) δ (ppm): 5.19 (s, 2H), 3.74 (s, 3H), 3.41 (s, 3H), 3.20 (s, 3H). LC-MS: m/z 332 (M+H).

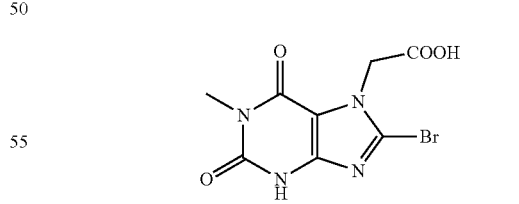

Step 2: 2-(8-bromo-1,3-dimethyl-2,6-dioxo-2,3-dihydro-1H-purin-7(6H)-yl)acetic acid Intermediate was prepared using hydrolysis reaction conditions as described. $^1$H NMR (400 MHz, DMSO-d$_6$): 13.60 (brs, 1H), 5.06 (s, 2H), 3.32 (s, 3H), 3.20 (s, 3H). LC-MS: m/z 316.94, 318.94 M−H, M−H+2) with a purity of 99%.

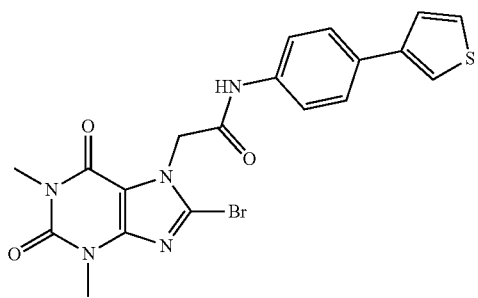 [SMILES: Cn1c(=O)c2c(nc(Br)n2CC(=O)Nc2ccc(-c3ccsc3)cc2)n(C)c1=O]

Step 3: 2-(8-bromo-1,3-dimethyl-2,6-dioxo-2,3-dihydro-1H-purin-7(6H)-yl)-N-(4-(thiophen-3-yl)phenyl)acetamide Product was prepared using amide coupling method A reaction conditions as described. ¹H NMR (400 MHz, DMSO-$d_6$): 10.57 (s, 1H), 7.80 (s, 1H), 7.70-7.68 (m, 2H), 7.62-7.59 (m, 3H), 7.52 (s, 1H), 5.20 (s, 2H), 3.43 (s, 3H), 3.21 (s, 3H). LC-MS: m/z 474.20 (M+H) with a purity of 96.04%. HPLC: At 279 nm with a purity of 97%.

Compound 77: 2-(1,3-dimethyl-2,6-dioxo-2,3-dihydro-1H-purin-7(6H)-yl)-N-(6-phenyl pyridazin-3-yl)propanamide

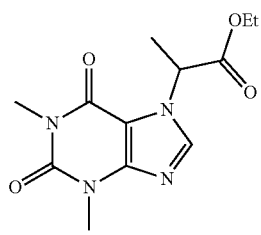 [SMILES: CCOC(=O)C(C)n1cnc2c1c(=O)n(C)c(=O)n2C]

Step 1: Preparation of ethyl 2-(1,3-dimethyl-2,6-dioxo-2,3-dihydro-1H-purin-7(6H)-yl) propanoate Intermediate was prepared using Mitsunobu reaction conditions as described. LC-MS: m/z 281 (M+H) with a purity of 46%.

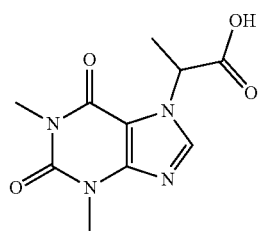 [SMILES: CC(C(=O)O)n1cnc2c1c(=O)n(C)c(=O)n2C]

Step 2: Preparation of 2-(1,3-dimethyl-2,6-dioxo-2,3-dihydro-1H-purin-7(6H)-yl)propanoic acid Intermediate was prepared using hydrolysis reaction conditions as described. ¹H-NMR (400 MHz; DMSO-$d_6$) δ (ppm): 13.27 (br s, 1H), 8.21 (s, 1H), 5.49-5.44 (q, J=7.5 Hz, 1H), 3.44 (s, 3H), 3.21 (s, 3H), 1.76-1.74 (d, J=7.5 Hz, 3H).

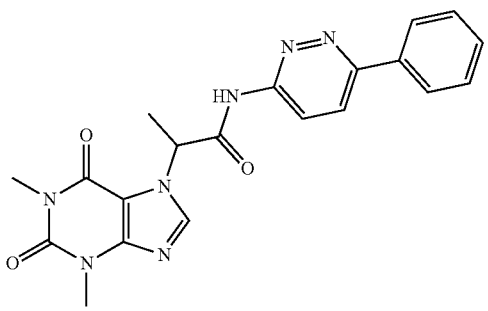 [SMILES: CC(C(=O)Nc1ccc(-c2ccccc2)nn1)n1cnc2c1c(=O)n(C)c(=O)n2C]

Step 3: Preparation of 2-(1,3-dimethyl-2,6-dioxo-2,3-dihydro-1H-purin-7(6H)-yl)-N-(6-phenylpyridazin-3-yl)propanamide Product was prepared using amide coupling method A reaction conditions as described. ¹H-NMR (400 MHz; CDCl₃) δ (ppm): 11.78 (s, 1H), 8.50-8.46 (m, 1H), 8.02-8.00 (dd, J=6.8, 3.2 Hz, 2H), 7.90-7.86 (m, 1H), 7.51-7.48 (m, 3H), 6.02-5.94 (q, J=7.6 Hz, 1H), 3.61 (s, 3H), 3.44 (s, 3H), 1.97-1.95 (d, J=7.2 Hz, 3H). MS (ESI): m/z 406.21 [M+H]+.

Compound 78: 2-(1,3-dimethyl-2,6-dioxo-2,3-dihydro-1H-purin-7(6H)-yl)-N-(6-(4-fluoro phenyl)pyridazin-3-yl)propanamide

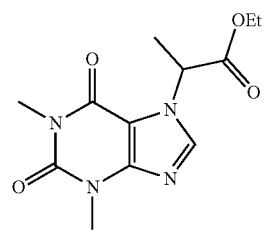

Step 1: Preparation of ethyl 2-(1,3-dimethyl-2,6-dioxo-2,3-dihydro-1H-purin-7(6H)-yl) propanoate Intermediate was prepared using Mitsunobu reaction conditions as described. LC-MS: m/z 281 (M+H) with a purity of 46%.

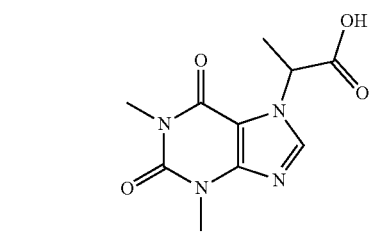 [SMILES: CCOC(=O)C(C)n1cnc2c1c(=O)n(C)c(=O)n2C]

Step 2: Preparation of 2-(1,3-dimethyl-2,6-dioxo-2,3-dihydro-1H-purin-7(6H)-yl)propanoic acid Intermediate was prepared using hydrolysis reaction conditions as described. ¹H-NMR (400 MHz; DMSO-$d_6$) δ

(ppm): 13.27 (br s, 1H), 8.21 (s, 1H), 5.49-5.44 (q, J=7.5 Hz, 1H), 3.44 (s, 3H), 3.21 (s, 3H), 1.76-1.74 (d, J=7.5 Hz, 3H).

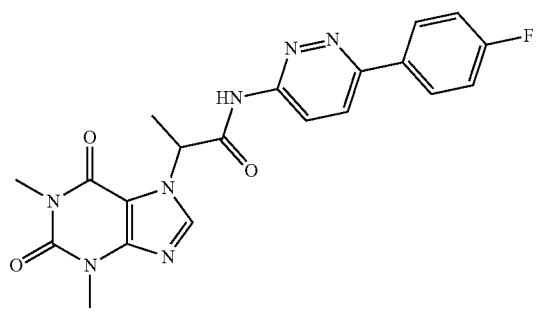 [SMILES: CC(C(=O)Nc1ccc(-c2ccc(F)cc2)nn1)n1cnc2c1c(=O)n(C)c(=O)n2C]

Step 3: Preparation of 2-(1,3-dimethyl-2,6-dioxo-2,3-dihydro-1H-purin-7(6H)-yl)-N-(6-(4-fluorophenyl)pyridazin-3-yl)propanamide Product was prepared using amide coupling method A reaction conditions as described. $^1$H-NMR (400 MHz; CDCl$_3$) δ (ppm): 10.39 (s, 1H), 8.46-8.44 (d, J=9.2 Hz, 1H), 8.03-8.00 (m, 2H), 7.88 (s, 1H), 7.84-7.82 (d, J=9.2 Hz, 1H), 7.21-7.16 (t, J=8.4 Hz, 2H), 5.91-5.87 (q, J=7.1 Hz, 1H), 3.60 (s, 3H), 3.45 (s, 3H), 1.96-1.94 (d, J=7.1 Hz, 3H). MS (ESI): m/z 422 [M−H]+.

Compound 79: (S)-2-(1,3-dimethyl-2,6-dioxo-2,3-dihydro-1H-purin-7(6H)-yl)-N-(4-(thiophen-3-yl)phenyl)propanamide

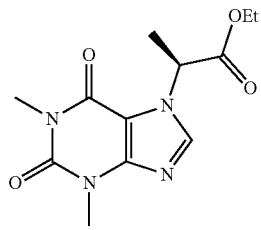 [SMILES: CCOC(=O)[C@H](C)n1cnc2c1c(=O)n(C)c(=O)n2C]

Step 1: Preparation of (S)-ethyl 2-(1,3-dimethyl-2,6-dioxo-2,3-dihydro-1H-purin-7(6H)-yl) propanoate Intermediate was prepared using Mitsunobu reaction conditions as described. $^1$H-NMR (400 MHz; DMSO-d$_6$) δ (ppm): 7.76 (s, 1H), 5.62 (q, J=7.6 Hz, 1H), 4.25 (q, J=6.8 Hz, 2H), 3.61 (s, 3H), 3.39 (s, 311), 1.85 (d, J=7.6 Hz, 3H), 1.29 (d, J=7.2 Hz, 3H). MS (ESI): m/z 281 [M+H]+. LC-MS: m/z 281 (M+H) with a purity of 48%.

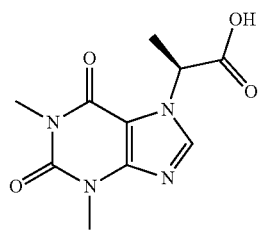 [SMILES: C[C@@H](C(=O)O)n1cnc2c1c(=O)n(C)c(=O)n2C]

Step 2: Preparation of (S)-2-(1,3-dimethyl-2,6-dioxo-2,3-dihydro-1H-purin-7(6H)-yl)propanoic acid Intermediate was prepared using hydrolysis reaction conditions as described. $^1$H-NMR (400 MHz; DMSO-d$_6$) δ (ppm): 13.28 (brs, 1H), 8.21 (s, 1H), 5.47 (q, J=7.6 Hz, 1H), 3.44 (s, 3H), 3.21 (s, 3H), 1.75 (d, J=7.6 Hz, 3H). MS (ESI): m/z 253.3 [M+H]+. LC-MS: Purity of 99%

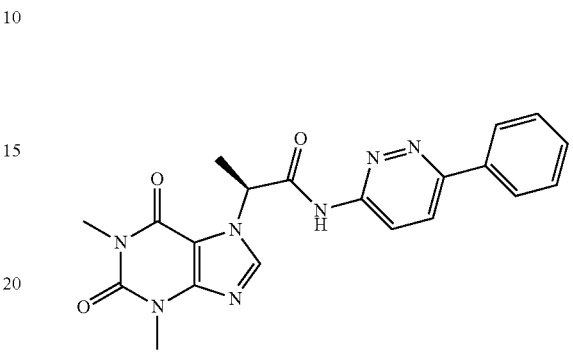

Step 3: Preparation of (S)-2-(1,3-dimethyl-2,6-dioxo-2,3-dihydro-1H-purin-7(6H)-yl)-N-(6-phenylpyridazin-3-yl)propanamide Product was prepared using amide coupling method A reaction conditions as described. $^1$H-NMR (400 MHz; DMSO-d$_6$) δ (ppm): 11.78 (s, 1H), 8.35 (s, 1H), 8.27 (dd, J=9.2 Hz, J=9.2 Hz, 2H), 8.1 (d, J=6.4 Hz, 2H), 7.57-7.51 (m, 3H), 5.84 (d, J=7.6 Hz, 1H), 3.46 (s, 3H), 3.19 (s, 3H), 1.9 (d, J=7.6 Hz, 3H). MS (ESI): m/z 406.21 [M+H]+. LC-MS: Purity of 97%.

Compound 80: (R)-2-(1,3-dimethyl-2,6-dioxo-2,3-dihydro-1H-purin-7(6H)-yl)-N-(4-(thiophen-3-yl)phenyl)propanamide

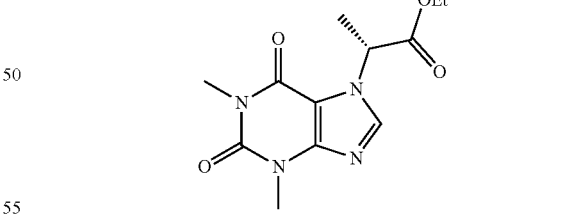

Step 1: Preparation of (R)-ethyl 2-(1,3-dimethyl-2,6-dioxo-2,3-dihydro-1H-purin-7(6H)-yl) propanoate Intermediate was prepared using Mitsunobu reaction conditions as described. $^1$H-NMR (400 MHz; DMSO-d$_6$) δ (ppm): 7.76 (s, 1H), 5.62 (q, J=7.6 Hz, 1H), 4.25 (q, J=6.8 Hz, 2H), 3.61 (s, 3H), 3.39 (s, 3H), 1.85 (d, J=7.6 Hz, 3H), 1.29 (d, J=7.2 Hz, 3H). MS (ESI): m/z 281 [M+H]+. LC-MS: m/z 281 (M+H) with a purity of 48%.

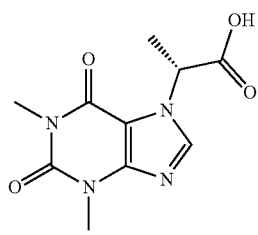 [SMILES: C[C@H](C(=O)O)n1cnc2c1c(=O)n(C)c(=O)n2C]

Step 2: Preparation of (R)-2-(1,3-dimethyl-2,6-dioxo-2,3-dihydro-1H-purin-7(6H)-yl) propanoic acid Intermediate prepared using hydrolysis reaction conditions as described. $^1$H-NMR (400 MHz; DMSO-d$_6$) δ (ppm): 13.28 (brs, 1H), 8.21 (s, 1H), 5.47 (q, J=7.6 Hz, 1H), 3.44 (s, 3H), 3.21 (s, 3H), 1.75 (d, J=7.6 Hz, 3H). MS (ESI): m/z 253.3 [M+H]+. LC-MS: Purity of 99%

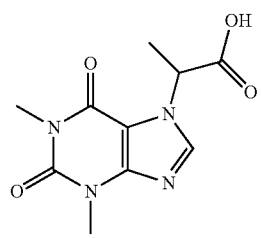

Step 3: Preparation of (R)-2-(1,3-dimethyl-2,6-dioxo-2,3-dihydro-1H-purin-7(6H)-yl)-N-(6-phenylpyridazin-3-yl)propanamide Product was prepared using amide coupling method A reaction conditions as described. $^1$H-NMR (400 MHz; CDCl$_3$) δ (ppm): 10.61 (s, 1H), 8.47 (d, J=9.6 Hz, 1H), 8.01 (dd, J=2.4 Hz, J=5.6 Hz, 2H), 7.89 (s, 1H), 7.86 (s, 1H), 7.49 (d, J=6.8 Hz, 3H), 5.98 (d, J=6.8 Hz, 1H), 3.61 (s, 3H), 3.43 (s, 3H), 1.96 (d, J=7.6 Hz, 3H). MS (ESI): m/z 406.21 [M+H]+. LC-MS: Purity of 97%.

Compound 81: 2-(1,3-dimethyl-2,6-dioxo-2,3-dihydro-1H-purin-7(6H)-yl)-N-(4-(thiazol-2-yl) phenyl)propanamide

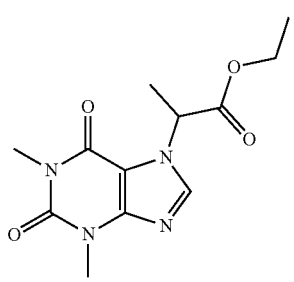

Step 1: Preparation of ethyl 2-(1,3-dimethyl-2,6-dioxo-2,3-dihydro-1H-purin-7(6H)-yl) propanoate Intermediate was prepared using alkylation method A reaction conditions as described. $^1$H NMR (400 MHz, DMSO-d$_6$) δ (ppm): 8.20 (s, 1H), 5.55 (q, J=7.2 Hz, 1H), 4.14 (q, J=7.2 Hz, 2H), 3.45 (s, 3H), 3.21 (s, 3H), 1.75 (d, J=7.2 Hz, 3H), 1.17 (t, J=7.2 Hz, 3H). LC-MS: m/z 281 (M+H)

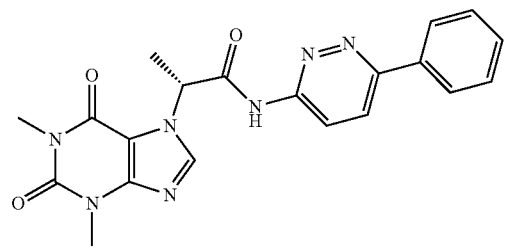 [SMILES: C[C@H](C(=O)Nc1ccc(-c2ccccc2)nn1)n1cnc2c1c(=O)n(C)c(=O)n2C]

Step 2: Preparation of 2-(1,3-dimethyl-2,6-dioxo-2,3-dihydro-1H-purin-7(6H)-yl)propanoic acid Intermediate was prepared using hydrolysis reaction conditions as described. $^1$H NMR (400 MHz, DMSO-d$_6$) δ (ppm): 8.20 (s, 1H), 5.47 (q, J=7.2 Hz, 1H), 3.44 (s, 3H), 3.21 (s, 3H), 1.75 (d, J=7.2 Hz, 3H). LC-MS: m/z 253 (M+H)

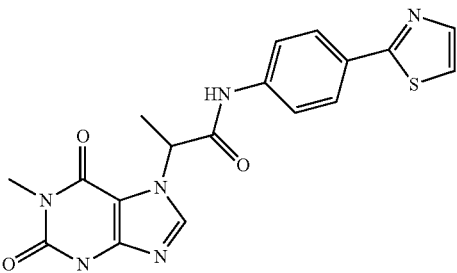

Step 3: Preparation of 2-(1,3-dimethyl-2,6-dioxo-2,3-dihydro-1H-purin-7(6H)-yl)-N-(4-(thiazol-2-yl) phenyl)propanamide Product was prepared using amide coupling method D reaction conditions as described. $^1$H NMR (400 MHz, DMSO-d$_6$) δ (ppm): 10.65 (s, 1H), 8.33 (s, 1H), 7.93-7.91 (m, 2H), 7.88 (d, J=3.2 Hz., 1H), 7.73-7.72 (m, 2H), 7.70 (m, 1H), 5.73-5.68 (q, J=7.2 Hz, 1H), 3.46 (s, 3H), 3.20 (s, 3H), 1.85 (d, J=7.2 Hz, 3H). LC-MS: m/z 411 (M+H) with a purity of 99%.

Compound 82: 2-(1,3-dimethyl-2,6-dioxo-2,3-di-hydro-1H-purin-7(6H)-yl)-N-(6-(thiazol-2-yl) pyridin-3-yl)propanamide

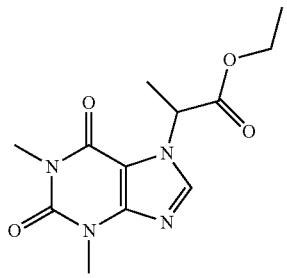 [SMILES: CCOC(=O)C(C)n1cnc2c1c(=O)n(C)c(=O)n2C]

Step 1: Preparation of ethyl 2-(1,3-dimethyl-2,6-dioxo-2,3-dihydro-1H-purin-7(6H)-yl) propanoate Intermediate was prepared using alkylation method A reaction conditions as described. $^1$H NMR (400 MHz, CDCl$_3$) δ (ppm): 7.97 (s, 1H), 5.59 (q, J=7.60 Hz, 1H), 4.24 (q, J=7.20 Hz, 2H), 3.58 (s, 3H), 3.36 (s, 3H), 1.83 (d, J=7.60 Hz, 3H), 1.28 (t, J=7.20 Hz, 3H). LC-MS: m/z 281 (M+H).

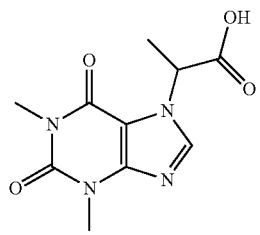 [SMILES: CC(C(=O)O)n1cnc2c1c(=O)n(C)c(=O)n2C]

Step 2: Preparation of 2-(1,3-dimethyl-2,6-dioxo-2,3-dihydro-1H-purin-7(6H)-yl)propanoic acid Intermediate was prepared using hydrolysis reaction conditions as described. $^1$H NMR (400 MHz, DMSO-d$_6$) δ (ppm): 8.19 (s, 1H), 5.46 (q, J=7.20 Hz, 1H), 3.44 (s, 3H), 3.21 (s, 3H), 1.74 (d, J=7.20 Hz, 3H). LC-MS: m/z 253 (M+H).

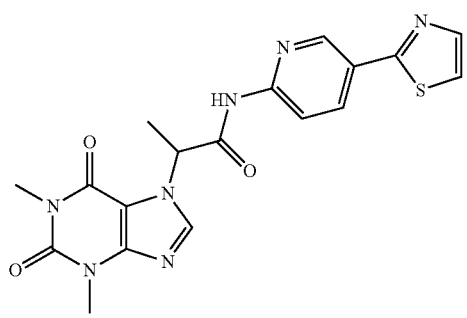 [SMILES: CC(C(=O)Nc1ccc(-c2nccs2)cn1)n1cnc2c1c(=O)n(C)c(=O)n2C]

Step 3: Preparation of 2-(1,3-dimethyl-2,6-dioxo-2,3-dihydro-1H-purin-7(6H)-yl)-N-(6-(thiazol-2-yl)pyridin-3-yl)propanamide Product was prepared using amide coupling method E reaction conditions as described. $^1$H NMR (400 MHz, DMSO-d$_6$) δ (ppm): 11.30 (s, 1H), 8.93 (s, 1H), 8.30-8.32 (m, 2H), 8.09-8.11 (m, 1H), 7.95 (d, J=2.00 Hz, 1H), 7.82 (d, J=2.00 Hz, 1H), 5.80 (q, J=7.20 Hz, 3H), 3.46 (s, 3H), 3.19 (s, 3H), 1.86 (d, J=7.20 Hz, 3H). LC-MS: m/z 412 (M+H) with a purity of 97%.

Compound 83: (R)-2-(1,3-dimethyl-2,6-dioxo-1,2,3,6-tetrahydro-7H-purin-7-yl)-N-(5-(thiazol-2-yl)pyridin-2-yl)propanamide

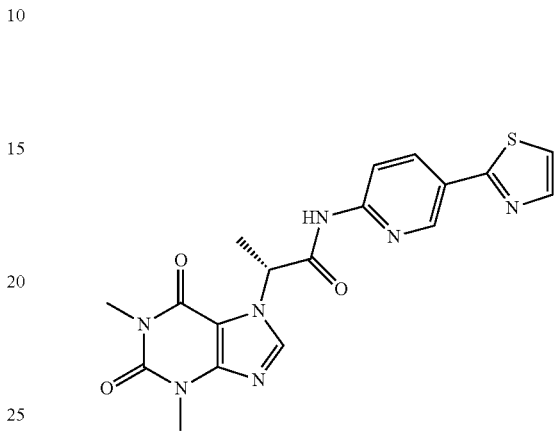

Product was prepared using chiral separation of the racemate. $^1$H NMR (400 MHz, DMSO-d$_6$) (ppm): 11.30 (s, 1H), 8.93 (s, 1H), 8.30-8.32 (m, 2H), 8.09-8.11 (m, 1H), 7.95 (d, J=2.00 Hz, 1H), 7.82 (d, J=2.00 Hz, 1H), 5.80 (q, J=7.20 Hz, 3H), 3.46 (s, 3H), 3.19 (s, 3H), 1.86 (d, J=7.20 Hz, 3H).

Compound 84: (S)-2-(1,3-dimethyl-2,6-dioxo-1,2,3,6-tetrahydro-7H-purin-7-yl)-N-(5-(thiazol-2-yl)pyridin-2-yl)propanamide

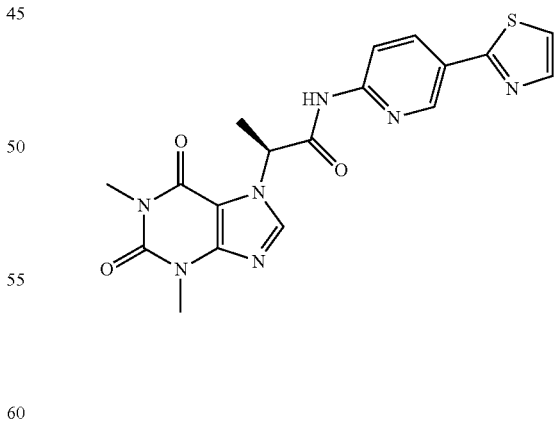

Product was prepared using chiral separation of the racemate. $^1$H NMR (400 MHz, DMSO-d$_6$) δ (ppm): 11.30 (s, 1H), 8.93 (s, 1H), 8.30-8.32 (m, 2H), 8.09-8.11 (m, 1H), 7.95 (d, J=2.00 Hz, 1H), 7.82 (d, J=2.00 Hz, 1H), 5.80 (q, J=7.20 Hz, 3H), 3.46 (s, 3H), 3.19 (s, 3H), 1.86 (d, J=7.20 Hz, 3H).

Compound 85: (R)-2-(1,3-dimethyl-2,6-dioxo-2,3-dihydro-1H-purin-7(6H)-yl)-N-(5-(2-methyl thiazol-4-yl)pyridin-2-yl)propanamide

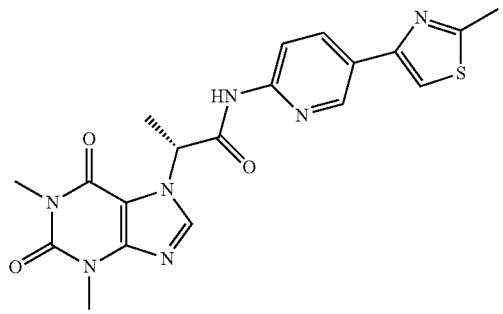

Product was prepared using amide coupling method A reaction conditions as described. The isomers were separated by chiral preparative HPLC to give (R)-2-(1,3-dimethyl-2,6-dioxo-2,3-dihydro-1H-purin-7(6H)-yl)-N-(5-(2-methylthiazol-4-yl)pyridin-2-yl)propanamide, $^1$H NMR (400 MHz, DMSO-$d_6$) δ (ppm): 11.18 (1H, s), 8.94-8.93 (1H, d, J=2.4 Hz), 8.33 (1H, s), 8.30-8.27 (1H, dd, J1=2.4 Hz, J2=6.4 Hz), 8.05-8.03 (1H, d, J=8.8 Hz), 8.01 (1H, s), 5.80-5.78 (1H, m) 3.45 (3H, s), 3.19 (3H, s), 2.72 (3H, s), 1.86-1.84 (3H, d, J=7.6 Hz). LC-MS: m/z 426.12 (M+H) with a purity of 97.84%. HPLC: At 254 nm with a purity of 97%. Chiral HPLC: 99%. Specific Rotation: +137 deg

Compound 86: (S)-2-(1,3-dimethyl-2,6-dioxo-2,3-dihydro-1H-purin-7(6H)-yl)-N-(5-(2-methylthiazol-4-yl)pyridin-2-yl)propanamide

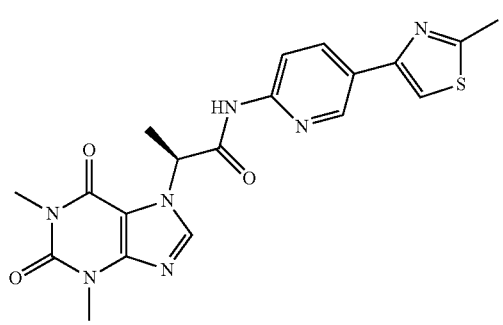

Product was prepared using amide coupling method A reaction conditions as described. The isomers were separated by chiral preparative HPLC to give 100 mg of (S)-2-(1,3-dimethyl-2,6-dioxo-2,3-dihydro-1H-purin-7(6H)-yl)-N-(5-(2-methylthiazol-4-yl)pyridin-2-yl)propanamide. $^1$H NMR (400 MHz, DMSO-$d_6$) δ (ppm): 11.18 (s, 1H), 8.94-8.93 (d, J=2.4 Hz, 1H), 8.33 (s, 1H), 8.30-8.27 (dd, J1=2.4 Hz, J2=6.4 Hz, 1H), 8.05-8.03 (d, J=8.8 Hz, 1H), 8.01 (s, 1H), 5.80-5.78 (q, J=7.5 Hz, 1H) 3.45 (s, 3H), 3.19 (s, 3H), 2.72 (s, 3H), 1.86-1.84 (d, J=7.6 Hz, 3H). LC-MS: m/z 426.12 (M+H) with a purity of 98.38%. HPLC: At 254 nm with a purity of 97%. Chiral HPLC: 99%. Specific Rotation: −127 deg

Compound 87: 3-(1,3-dimethyl-2,6-dioxo-1,2,3,6-tetrahydro-7H-purin-7-yl)-N-(4-(thiophen-3-yl)phenyl)propanamide

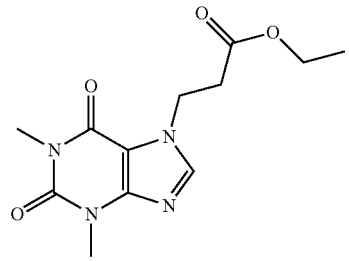 [SMILES: CCOC(=O)CCn1cnc2c1c(=O)n(C)c(=O)n2C]

Step 1: Preparation of ethyl 3-(1,3-dimethyl-2,6-dioxo-1,2,3,6-tetrahydro-7H-purin-7-yl)propanoate The intermediate was prepared using alkylation conditions. $^1$H NMR (400 MHz, DMSO-$d_6$): 8.03 (s, 1H), 4.46 (t, J=6.8 Hz, 2H), 4.05 (q, t=6.6 Hz, 2H), 3.42 (s, 3H), 3.24 (s, 3H), 2.93 (t, J=6.6 Hz, 2H), 1.15 (t, J=6.8 Hz, 3H). LC-MS: m/z 281 (M+H).

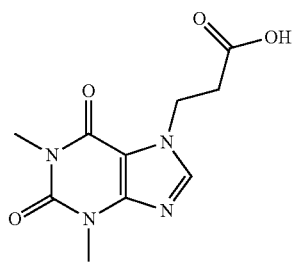 [SMILES: Cn1c(=O)c2c(ncn2CCC(=O)O)n(C)c1=O]

Step 2: Preparation of 3-(1,3-dimethyl-2,6-dioxo-1,2,3,6-tetrahydro-7H-purin-7-yl)propanoic acid $^1$H NMR (400 MHz, DMSO-$d_6$): 8.01 (s, 1H), 4.43 (t, J=6.8 Hz, 2H), 3.42 (s, 3H), 3.24 (s, 3H), 2.84 (t, J=6.8 Hz, 2H). LC-MS: m/z 253 (M+H)

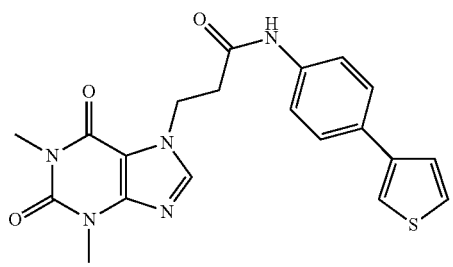 [SMILES: Cn1c(=O)c2c(ncn2CCC(=O)Nc2ccc(-c3ccsc3)cc2)n(C)c1=O]

Step 3: Preparation of 3-(1,3-dimethyl-2,6-dioxo-1,2,3,6-tetrahydro-7H-purin-7-yl)-N-(4-(thiophen-3-yl)phenyl)propanamide $^1$H NMR (400 MHz, DMSO-$d_6$): 9.99 (s, 1H), 8.00 (s, 1H), 7.75 (br s, 1H), 7.64-7.55 (m, 5H), 7.51-7.49 (d, J=5.2

Hz, 1H), 4.54 (t, J=6.4 Hz, 2H), 3.42 (s, 3H), 2.96 (t, J=6.4 Hz, 2H). LC-MS: m/z 410 (M+H) with a purity of 99%.

Compound 88: 4-(1,3-dimethyl-2,6-dioxo-1,2,3,6-tetrahydro-7H-purin-7-yl)-N-(4-(thiophen-3-yl)phenyl)butanamide

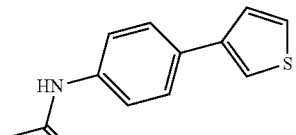

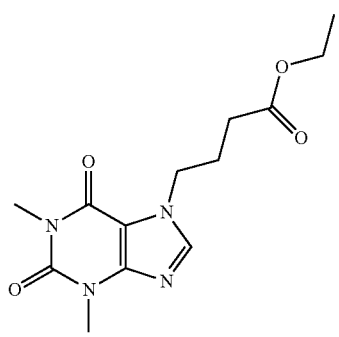 [SMILES: CCOC(=O)CCCn1cnc2c1c(=O)n(C)c(=O)n2C]

Step 1: Preparation of ethyl 4-(1,3-dimethyl-2,6-dioxo-1,2,3,6-tetrahydro-7H-purin-7-yl)butanoate The intermediate was prepared using alkylation conditions. ¹H NMR (400 MHz, CDCl₃-d) δ 7.55 (s, 1H), 4.37 (t, J=6.80 Hz, 2H), 4.13 (q, J=7.20 Hz, 2H), 3.59 (s, 3H), 3.41 (s, 3H), 2.32 (t, J=6.80 Hz, 2H), 2.21 (p, J=6.80 Hz, 2H), 1.25 (q, J=7.20 Hz, 3H). LC-MS: m/z 295 (M+H) with a purity of 98%.

Step 3: Preparation of 4-(1,3-dimethyl-2,6-dioxo-1,2,3,6-tetrahydro-7H-purin-7-yl)-N-(4-(thiophen-3-yl)phenyl)butanamide The final product is prepared using amide coupling method A reaction conditions. ¹H NMR (Methanol-d₄) δ 7.92 (s, 1H), 7.53-7.57 (m, 3H), 7.47-7.50 (m, 2H), 7.43-7.45 (m, 1H), 7.40-7.41 (m, 1H), 4.45 (t, J=6.80 Hz, 2H), 3.45 (s, 3H), 3.33 (s, 3H), 2.43 (t, J=6.80 Hz, 2H), 2.31 (p, J=6.80 Hz, 2H). LCMS (ESI) m/z 424 (MH+) with a purity of 97%.

Compound 89: 2-(1,3-dimethyl-2,6-dioxo-1,2,3,6-tetrahydro-7H-purin-7-yl)-N-(4-(thiophen-2-yl)phenyl)acetamide

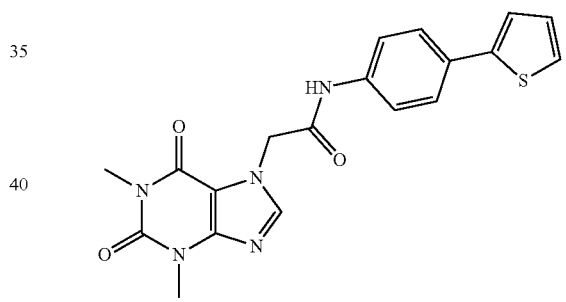

¹H NMR (400 MHz, DMSO-d₆): 10.48 (s, 1H), 8.07 (s, 1H), 7.62 (s, 4H), 7.49 (d, J=5.2 Hz, 1H), 7.43 (d, J=3.6 Hz, 1H), 7.11 (m, 1H), 5.22 (s, 2H), 3.47 (s, 3H), 3.21 (s, 3H). LC-MS: m/z 396 (M+H) with a purity of 97%.

Compound 90: 3-(1,3-dimethyl-2,6-dioxo-1,2,3,6-tetrahydro-7H-purin-7-yl)-N-(4-(thiophen-2-yl)phenyl)propanamide

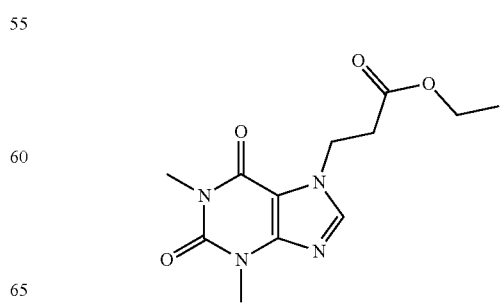

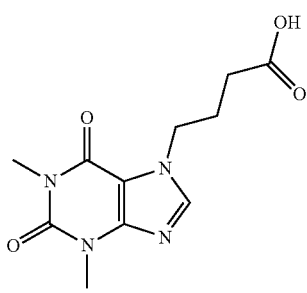 [SMILES: Cn1c(=O)c2c(ncn2CCCC(=O)O)n(C)c1=O]

Step 2: Preparation of 4-(1,3-dimethyl-2,6-dioxo-1,2,3,6-tetrahydro-7H-purin-7-yl)butanoic acid The intermediate was prepared using hydrolysis conditions. ¹H NMR (400 MHz, DMSO-d₆) δ 8.05 (s, 1H), 4.26 (t, J=7.20 Hz, 2H), 3.42 (s, 3H), 3.22 (s, 3H), 2.19 (t, J=7.20 Hz, 2H), 2.01 (q, J=7.20 Hz, 2H). LC-MS: m/z 267 (M+H).

$^1$H NMR (400 MHz, DMSO-d$_6$): 10.05 (s, 1H), 8.00 (s, 1H), 7.57 (s, 4H), 7.47 (d, J=5.2 Hz, 1H), 7.40 (d, J=3.6 Hz, 1H), 7.10 (t, J=4.2 Hz, 1H), 4.54 (t, J=6.4 Hz, 2H), 3.42 (s, 3H), 3.26 (s, 3H), 2.96 (t, J=6.4 Hz, 2H). LC-MS: m/z 410 (M+H) with a purity of 97%.

Compound 91: 4-(1,3-dimethyl-2,6-dioxo-1,2,3,6-tetrahydro-7H-purin-7-yl)-N-(4-(thiophen-2-yl)phenyl)butanamide 1p;2p

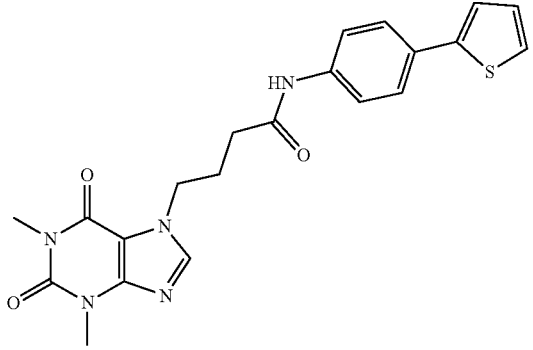 [SMILES: Cn1c(=O)c2c(ncn2CCCC(=O)Nc2ccc(-c3cccs3)cc2)n(C)c1=O]

$^1$H NMR (Methanol-d$_4$) δ 7.92 (s, 1H), 7.47-7.55 (m, 4H), 7.30-7.32 (m, 2H), 7.06 (t, J=4.40 Hz, 1H), 4.45 (t, J=6.80 Hz, 2H), 3.45 (s, 3H), 3.33 (s, 3H), 2.43 (t, J=6.80 Hz, 2H), 2.30 (p, J=6.80 Hz, 2H). LCMS (ESI) m/z 424 (MH+). LCMS (ESI) m/z 424 (MH+) with a purity of 98%.

Compound 92: 3-(1,3-dimethyl-2,6-dioxo-1,2,3,6-tetrahydro-7H-purin-7-yl)-N-(4-(2-methylthiazol-4-yl)phenyl)propanamide

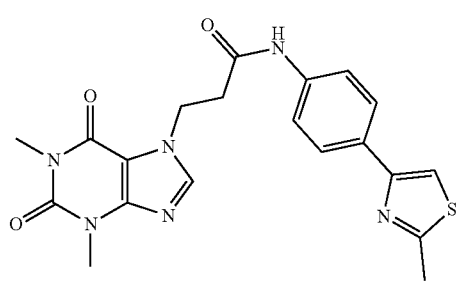 [SMILES: Cc1nc(-c2ccc(NC(=O)CCn3cnc4c3c(=O)n(C)c(=O)n4C)cc2)cs1]

$^1$H NMR (400 MHz, Methanol-d$_4$) δ 7.92 (s, 1H), 7.78-7.80 (m, 2H), 7.54-7.55 (m, 3H), 4.67 (t, J=6.00 Hz, 2H), 4.55 (bs, 1H), 3.52 (s, 3H), 3.37 (s, 3H), 3.01 (t, J=6.00 Hz, 2H), 2.73 (s, 3H). LC-MS: m/z 425 (M+H) with a purity of 99%.

Compound 93: 3-(1,3-dimethyl-2,6-dioxo-1,2,3,6-tetrahydro-7H-purin-7-yl)-N-(4-(thiazol-2-yl)phenyl)propanamide

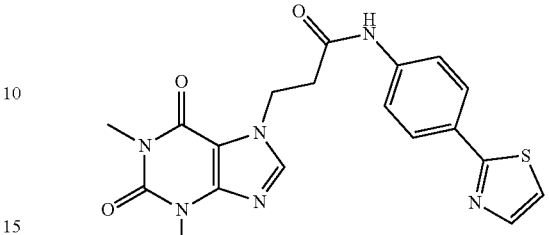

$^1$H NMR (400 MHz, DMSO-do) δ 10.17 (s, 1H), 8.00 (s, 1H), 7.85-7.88 (m, 3H), 7.65-7.70 (m, 3H), 4.54 (t, J=6.40 Hz, 2H), 3.42 (s, 3H), 2.99 (t, J=6.40 Hz, 2H). LC-MS: m/z 411 (M+H) with a purity of 99%.

Compound 94: 4-(1,3-dimethyl-2,6-dioxo-1,2,3,6-tetrahydro-7H-purin-7-yl)-N-(4-(thiazol-2-yl)phenyl)butanamide

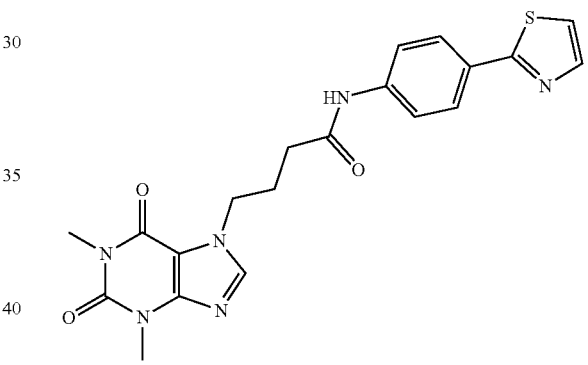

$^1$H NMR (400 MHz, Methanol-d$_4$) δ 7.95 (s, 1H), 7.86 (d, J=8.80 Hz, 2H), 7.82 (d, J=3.20 Hz, 1H), 7.61 (d, J=8.80 Hz, 2H), 7.55 (d, J=3.20 Hz, 1H), 4.45 (t, J=6.80 Hz, 2H), 3.45 (s, 3H), 3.33 (s, 3H), 2.45 (t, J=6.80 Hz, 2H), 2.31 (p, J=6.80 Hz, 2H). LC-MS: m/z 425 (M+H) with a purity of 96%.

Application Example 1

Materials and Methods:
Cell Lines and Culture Conditions:
HEK293-STF cell line was modified from Human embryonic kidney cell line HEK293 transfected with the STF reporter. HEK293-STF3A cell line was further modified from HEK293-STF cell line to express Wnt3A. This cell line was used to identify compounds that regulate either early or late signalling components of the Wnt pathway. L-Wnt3A (ATCC, #CRL-2647) cell line was used for providing Wnt3A conditioned media. The three cell lines were grown in DMEM (Dulbecco's Modified Eagle Medium) with 10% FBS (fetal bovine serum) incubated in 37° C. with 5% CO$_2$.
Cell Viability Assay:
5000 cells in 75 μl culture media were seeded in each well of black 96 well plates (Greiner #655090) and incubated overnight at 37° C. 25 μl of serially diluted compound was added to the cells giving final concentration of 50 µM to 1.5 nM. After 1 day of treatment, 100 µl of CellTiter-Glo® Luminescent Cell Viability Assay reagent (#G7571, Promega) was added to each well and incubated for 10 minutes at room temperature. Luminescence was measured using Tecan Safire2® microplate reader.

STF3A Assay:

2×10⁴ HEK293-STF3A cells in 75 µl culture media were seeded in each well of white 96 well plates (Greiner #655098) and incubated overnight at 37° C. 25 µl serially diluted compound was added to the cells to give final concentration of 50 µM to 1.5 nM. After 1 day of treatment, 100 µl of Steady-Glo® Luciferase Assay reagent (#E2520, Promega) was added to each well and incubated for 10 minutes at room temperature. Luminescence was measured using Tecan Safire2® plate reader.

STF/WNT3A Conditioned Medium (STF/WNT3A CM) Assay:

L-Wnt3A cells were cultured in three T-175 flasks at 3×10⁴ cells/ml in 30 ml culture medium per flask. After 4 days of incubation, the Wnt3A conditioned media were harvested and then centrifuged at 2000 rpm for 10 minutes to remove the debris. The Wnt3A conditioned media were stored at −20° C. if not used immediately.

2×104 HEK293-STF cells in 25 µl culture media were added in each well of white 96 well plates (Greiner #655098). 25 µl serially diluted compound was added to the cells. After 4 hours of incubation, 100 µl Wnt-3A conditioned medium was added to the cells. The final concentration of compound ranged from 33 µM to 1 nM. After incubation for 1 day at 37° C., 100 µl of Steady-Glo® Luciferase Assay reagent (#E2520, Promega) was added to each well and incubated for 10 minutes at room temperature. Luminescence was measured using Tecan Safire2® microplate reader.

Results:

| Compound | STF3A IC50 µM |
| --- | --- |
| 1 | <0.1 |
| 2 | <0.1 |
| 3 | <1 |
| 4 | <1 |
| 5 | <0.1 |
| 6 | <1 |
| 7 | >10 |
| 8 | <5 |
| 9 | <0.1 |
| 10 | <1 |
| 11 | <0.1 |
| 12 | <5 |
| 13 | >10 |
| 14 | <1 |
| 15 | <0.1 |
| 16 | <1 |
| 17 | >10 |
| 18 | <0.1 |
| 19 | <0.1 |
| 20 | <0.1 |
| 21 | <0.1 |
| 22 | <0.1 |
| 23 | <0.1 |
| 24 | <1 |
| 25 | <0.1 |
| 26 | <0.1 |
| 27 | >10 |
| 28 | >10 |
| 29 | <0.1 |
| 30 | <0.1 |
| 31 | <5 |
| 32 | <0.1 |
| 33 | <0.1 |
| 34 | <0.1 |
| 35 | <0.1 |
| 36 | <0.1 |
| 37 | <0.1 |
| 38 | <0.1 |
| 39 | >10 |
| 40 | <1 |
| 41 | <0.1 |
| 42 | >10 |
| 43 | >10 |
| 44 | >10 |
| 45 | <0.1 |
| 46 | <1 |
| 47 | <1 |
| 48 | <1 |
| 49 | <1 |
| 50 | <1 |
| 51 | <1 |
| 52 | <1 |
| 53 | <0.1 |
| 54 | <0.1 |
| 55 | <5 |
| 56 | <1 |
| 57 | <0.1 |
| 58 | >10 |
| 59 | <0.1 |
| 60 | <1 |
| 61 | <0.1 |
| 62 | <0.1 |
| 63 | <1 |
| 64 | <0.1 |
| 65 | >10 |
| 66 | <0.1 |
| 67 | <1 |
| 68 | <0.1 |
| 69 | <0.1 |
| 70 | <0.1 |
| 71 | >10 |
| 72 | <0.1 |
| 73 | <0.1 |
| 74 | <1 |
| 75 | <1 |
| 76 | <0.1 |
| 77 | <0.1 |
| 78 | <1 |
| 79 | <0.1 |
| 80 | >10 |
| 81 | <0.1 |
| 82 | <0.1 |
| 83 | <10 |
| 84 | <0.1 |
| 85 | <5 |
| 86 | <0.1 |
| 87 | <0.1 |
| 88 | <0.1 |
| 89 | <0.1 |
| 90 | <0.1 |
| 91 | <0.1 |
| 92 | <1 |
| 93 | <1 |
| 94 | <1 |

Figure 1A:
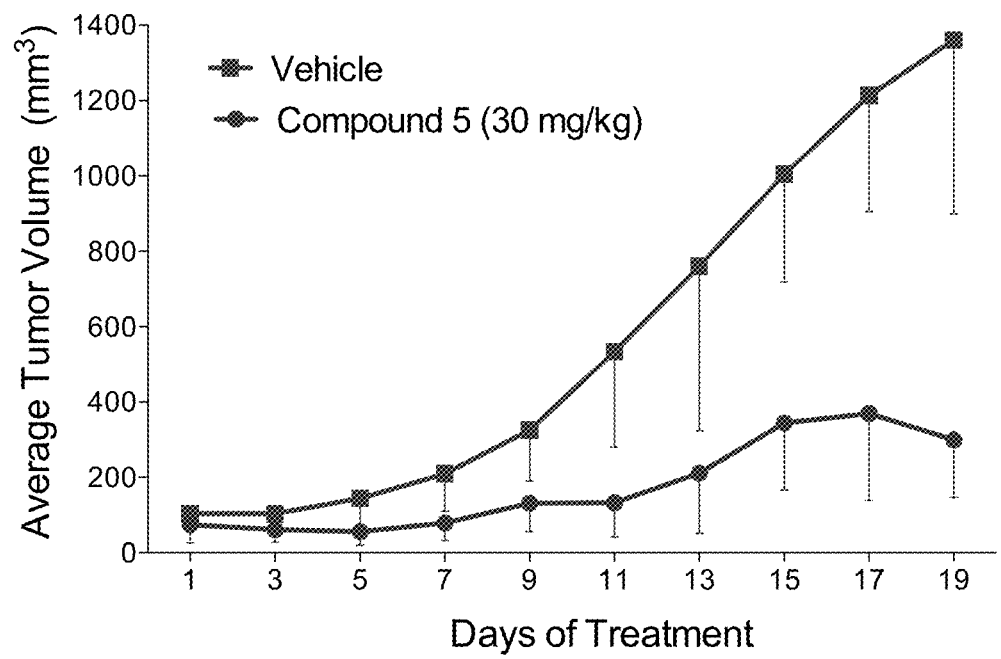
FIGS. 1A-1B show tumour weights (FIG. 1B) and volumes (FIG. 1A) in mice treated with Compound 5.
Figure 1B:
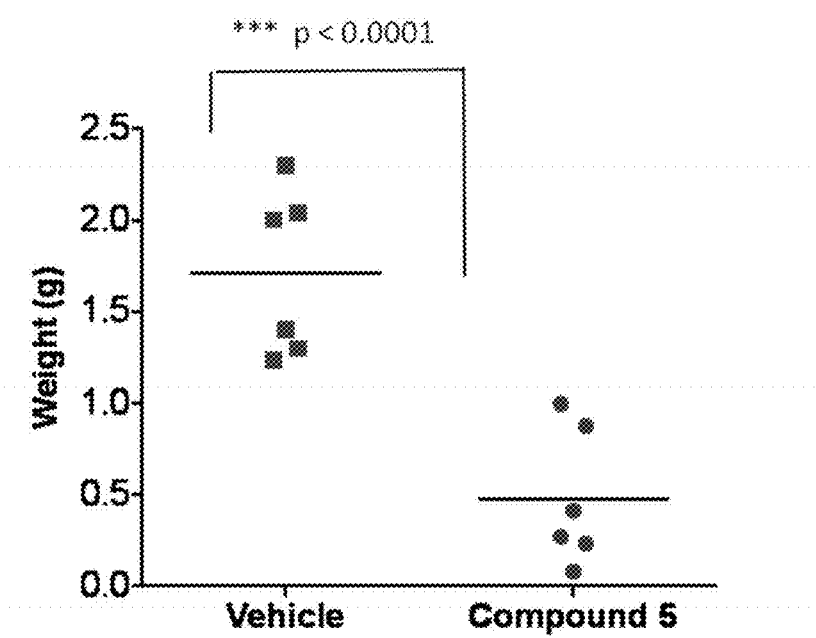

MMTV-WNT1 Tumor Model:

To test the in vivo efficacy of Compound 5 to prevent the growth of Wnt driven tumors, fragments from two independent MMTV-WNT1 tumors were orthotopically transplanted into female nude mice. The mice were treated with either vehicle or Compound 5, 30 mg/kg once daily for 19 days. Tumor volumes were measured on alternate days. Treatment with Compound 5 decreased tumor growth in all the treated mice. A significant decrease in tumor weights collected at sacrifice was also observed. Results are shown in FIG. 1.

Cytoplasmic and Nuclear β-Catenin Experiment

Result: Compound 5 decreased cytoplasmic and nuclear β-catenin in tumors. Staining the tumor sections for β-catenin showed that vehicle treated tumors had abundant β-catenin in cytoplasm and nucleus. Two representative samples from each treatment arm are shown in FIG. 2.

Phospho-LRP6 Assay as a Target Efficacy Marker for Compound 5

Palmitoylation of Wnts is essential for Wnt/β-Catenin signaling. Once Wnts are palmitoylated by the O-acyl transferase porcupine they are secreted and subsequently bind to the receptor complex, consisting of Frizzled (cognate receptors) and the co-receptor LRP5 or LRP6 (Cadigan and Peifer, 2009). LRP5 and LRP6 are highly homologous single-pass transmembrane proteins of the low-density lipoprotein receptor (LDLR)-related protein family. Upon Wnt binding LRP is phosphorylated on multiple sites (including Thr 1479, Ser 1490 and Thr1493) by kinases such as Casein Kinase 1 (CK1), Glycogen Synthase Kinase 3 (GSK3) or MEK1 (Cervenka et al., 2011; Tamai et al., 2004; Zeng et al., 2005). Phosphorylated LRP then recruits axin to the membrane and subsequently activates β-Catenin signalling.

The present target efficacy biomarker assay measures a decrease in levels of p-LRP6 (i.e. phosphorylated LRP-6) (Ser1490) upon treatment with a porcupine inhibitor (Compound 5). Cells treated with 2 μM of the test compound in vitro showed a greater than 50% reduction in p-LRP6 from 4 h onwards, with no decrease observed in total LRP levels (FIG. 3). The inhibitory effect remains up to 72 h (data not shown) in the presence of the compound and up to 12 h after the compound has been removed (data not shown).

While 2 μM led to 50-60% inhibition after 6 h of in vitro treatment, 3.3 nM of Compound 5 still inhibited p-LRP6 (Ser1490) by about 20% in this assay (FIG. 4). Concentrations lower than 3.3 nM did not inhibit p-LRP6 in HPAF-II pancreatic adenocarcinoma cells (data not shown).

The inventors have validated that this assay works alike for cancer cells and tumour tissue (data not shown).

REFERENCES

Cadigan, K. M., and Peifer, M. (2009). Wnt signaling from development to disease: insights from model systems. Cold Spring Harbor perspectives in biology 1, a002881.

Cervenka, I., Wolf, J., Masek, J., Krejci, P., Wilcox, W. R., Kozubik, A., Schulte, G., Gutkind, J. S., and Bryja, V. (2011). Mitogen-activated protein kinases promote WNT/beta-catenin signaling via phosphorylation of LRP6. Molecular and cellular biology 31, 179-189.

Tamai, K., Zeng, X., Liu, C., Zhang, X., Harada, Y., Chang, Z., and He, X. (2004). A mechanism for Wnt coreceptor activation. Molecular cell 13, 149-156.

Zeng, X., Tamai, K., Doble, B., Li, S., Huang, H., Habas, R., Okamura, H., Woodgett, J., and He, X. (2005). A dual-kinase mechanism for Wnt co-receptor phosphorylation and activation. Nature 438, 873-877.

The invention claimed is:

1. A pharmaceutical composition for oral administration to a subject in need thereof, comprising a Wnt secretion modulating compound having structure (I)

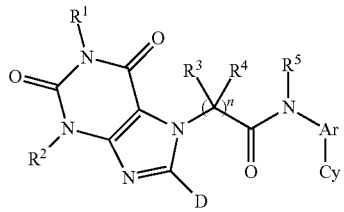

wherein:
$R^1$, $R^2$, $R^3$, $R^4$ and $R^5$ are each, independently, H or an alkyl group;
D is selected from the group consisting of H, halogen, alkyl, cycloalkyl, aryl, and dialkylamino, each (other than H and halogen) being optionally substituted;
Ar is a 6-membered heteroaryl ring having 1 or 2 nitrogen atoms having no substituents other than Cy and the amide nitrogen atom depicted in structure (I), these being in a 1,4-relationship on the ring; and
Cy is an aryl, heteroaryl or a saturated ring containing at least one heteroatom, each being optionally substituted; and
n is an integer from 1 to 2;
or an enantiomer, diastereomer or salt thereof;
together with one or more pharmaceutically acceptable carriers, diluents or adjuvants.

2. The pharmaceutical composition according to claim 1, wherein the adjuvants are selected from emollients, emulsifiers, thickening agents, preservatives, bactericides, buffering agents, and combinations thereof.

3. The pharmaceutical composition according to claim 1, wherein the one or more pharmaceutically acceptable carriers, diluents or adjuvants is independently selected from peanut oil, liquid paraffin, sodium carboxymethylcellulose, methylcellulose, sodium alginate, gum acacia, gum tragacanth, dextrose, sucrose, sorbitol, mannitol, gelatin, lecithin, and combinations thereof.

4. The pharmaceutical composition according to claim 1, further comprising a coloring agent.

5. The pharmaceutical composition according to claim 1, further comprising a binder selected from gum acacia, gelatin, corn starch, gum tragacanth, sodium alginate, carboxymethylcellulose, polyethylene glycol, and combinations thereof.

6. The pharmaceutical composition according to claim 1, further comprising a sweetener selected from sucrose, lactose, glucose, aspartame, saccharine, and combinations thereof.

7. The pharmaceutical composition according to claim 1, further comprising a disintegrating agent selected from corn starch, methylcellulose, polyvinylpyrrolidone, guar gum, xanthan gum, bentonite, alginic acid, agar, and combinations thereof.

8. The pharmaceutical composition according to claim 1, wherein the diluents are selected from lactose, sorbitol, mannitol, dextrose, kaolin, cellulose, calcium carbonate, calcium silicate, dicalcium phosphate, and combinations thereof.

9. The pharmaceutical composition according to claim 1, further comprising a flavoring agent selected from peppermint oil, oil of wintergreen, cherry flavoring, orange flavoring, raspberry flavoring, and combinations thereof.

10. The pharmaceutical composition according to claim 1, further comprising a coating agent selected from a polymer or copolymer of acrylic acid and/or methacrylic acid and/or their esters, waxes, fatty alcohols, zein, shellac, gluten, and combinations thereof.

11. The pharmaceutical composition according to claim 1, further comprising a preservative selected from sodium benzoate, vitamin E, alpha-tocopherol, ascorbic acid, methyl paraben, propyl paraben, sodium bisulphite, and combination s thereof.

12. The pharmaceutical composition according to claim 1, further comprising a lubricant selected from magnesium stearate, stearic acid, sodium oleate, sodium chloride, talc, and combinations thereof.

13. The pharmaceutical composition according to claim 1, further comprising a time delay agent selected from glyceryl monostearate, glyceryl distearate, and combinations thereof.

14. The pharmaceutical composition according to claim 1, further comprising a liquid carrier selected from water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides, and combinations thereof.

15. The pharmaceutical composition according to claim 1, further comprising a dispersing agent selected from lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate, and combinations thereof.

16. The pharmaceutical composition according to claim 1, further comprising a suspending agent selected from sodium carboxymethylcellulose, methylcellulose, hydroxypropylmethyl-cellulose, poly-vinyl-pyrrolidone, sodium alginate, acetyl alcohol, and combinations thereof.

17. The pharmaceutical composition according to claim 1, further comprising an emulsifying agent selected from lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate, natural gums such as guar gum, gum acacia, gum tragacanth, and combinations thereof.

18. The pharmaceutical composition according to claim 1, wherein the composition is provided in a form suitable for oral ingestion selected from capsules, tablets, caplets, and elixirs, or in an aerosol form suitable for oral inhalation.

* * * * *